United States Patent [19]
Demuth, Jr. et al.

[11] Patent Number: 5,491,139
[45] Date of Patent: Feb. 13, 1996

[54] ANTIMICROBIAL QUINOLONYL LACTAMS

[75] Inventors: Thomas P. Demuth, Jr., Norwich; Ronald E. White, South Plymouth, both of N.Y.

[73] Assignee: The Procter & Gamble Company, Cincinnati, Ohio

[21] Appl. No.: 224,120

[22] Filed: Apr. 6, 1994

Related U.S. Application Data

[63] Continuation of Ser. No. 672,150, Mar. 19, 1991, abandoned, which is a continuation of Ser. No. 416,646, Oct. 10, 1989, abandoned, which is a continuation-in-part of Ser. No. 261,767, Oct. 24, 1988, abandoned.

[51] Int. Cl.$^6$ .................... C07D 499/00; A61K 31/43
[52] U.S. Cl. .................... 514/192; 514/195; 540/310; 540/312
[58] Field of Search ................... 540/310, 312; 514/192, 195

[56] References Cited

U.S. PATENT DOCUMENTS

| | | | |
|---|---|---|---|
| 4,146,719 | 3/1979 | Irikura | 544/363 |
| 4,620,007 | 10/1986 | Grohe et al. | 546/156 |
| 4,631,150 | 12/1986 | Battistini et al. | 540/310 |
| 4,670,444 | 6/1987 | Grohe et al. | 514/300 |
| 4,742,053 | 5/1988 | Nakagawa et al. | 514/202 |
| 4,904,647 | 2/1990 | Kulcsar et al. | 514/154 |
| 5,013,730 | 5/1991 | Arnould et al. | 514/202 |
| 5,013,731 | 5/1991 | Arnould et al. | 514/202 |
| 5,180,719 | 1/1993 | White et al. | 514/192 |

FOREIGN PATENT DOCUMENTS

| | | |
|---|---|---|
| 8775009 | 1/1988 | Australia . |
| 8827554 | 6/1989 | Australia . |
| 53816 | 6/1982 | European Pat. Off. . |
| 62328 | 10/1982 | European Pat. Off. . |
| 203559 | 12/1986 | European Pat. Off. . |
| 0304158A1 | 2/1989 | European Pat. Off. . |
| 335297 | 10/1989 | European Pat. Off. . |
| 341990 | 11/1989 | European Pat. Off. . |
| 0366643A2 | 5/1990 | European Pat. Off. . |
| 0366641A2 | 5/1990 | European Pat. Off. . |
| 0366189A2 | 5/1990 | European Pat. Off. . |
| 0366640A2 | 5/1990 | European Pat. Off. . |
| 0453952A2 | 10/1991 | European Pat. Off. . |
| 0453924A1 | 10/1991 | European Pat. Off. . |
| 0451764A1 | 10/1991 | European Pat. Off. . |
| 2191556 | 3/1974 | France . |
| 2243940 | 4/1975 | France . |
| 1940511 | 3/1970 | Germany . |
| 2322750 | 11/1972 | Germany . |
| 2448966 | 4/1975 | Germany . |
| 2514322 | 10/1975 | Germany . |
| 2947948 | 6/1980 | Germany . |
| 3345093 | 6/1984 | Germany . |
| 47-11237 | 4/1972 | Japan . |
| 49-35392 | 4/1974 | Japan . |
| 50-23037 | 8/1975 | Japan . |
| 50-23036 | 8/1975 | Japan . |
| 57-32290 | 2/1982 | Japan . |
| 57-46990 | 3/1982 | Japan . |
| 57-46988 | 3/1982 | Japan . |
| 60-06617 | 1/1985 | Japan . |
| 1258684 | 10/1989 | Japan . |
| 8705297 | 9/1987 | WIPO . |
| WO91/16310 | 10/1991 | WIPO . |
| WO91/16327 | 10/1991 | WIPO . |

OTHER PUBLICATIONS

Perrone, E. et al., "Dual Action Penems" Abstract #825; *Abstracts of these 1991 ICAAC* (Abstract only).

Albrecht, H. A., "Dual–Action Cephalosporins Incorporating 3'–Tertiary Amine–Linked Quinolones", *31st Interscience Conference on Antibacterial Agents and Chemotherapy*, Chicago, Illinois; Poster Session: Oct. 2, 1991 (Abs. & Poster).

Corraz, A. J. et al., "Dual–Action Penems and Carbapenems", Abstract #826, Poster #73, *31st Interscience Conference on Antimicrobial Agents and Chemotherapy* (Chicago, Illinois), Oct. 1, 1991 (Abstract & Poster).

Schaeffer, F. F. et al., "The Role of AMPC β–Lactamase in the Mechanism of Action of Ester–Linked Dual–Action Cephalosporins", Abstract #953, *31st Interscience Conference on Antimicrobial Agents and Chemotherapy*, Poster Session, Oct. 1, 1991 (Abstract & Poster).

Bartkovitz, D., et al., "The Synthesis and Biological Properties of 2α–Methyl Substituted Penicillins", Abstract #824, *31st Interscience Conference on Antibacterial Agents and Chemotherapy* (Chicago, Illinois), Oct. 1, 1991 (Abstract & Poster).

(List continued on next page.)

Primary Examiner—Nicholas Rizzo
Attorney, Agent, or Firm—William J. Winter; Karen F. Clark; David L. Suter

[57] ABSTRACT

Antimicrobial quinolonyl lactam compounds comprising a lactam-containing moiety linked, by a non-ester linking moiety, to the 3-carboxy group of a quinolone moiety. These compounds are of the formula:

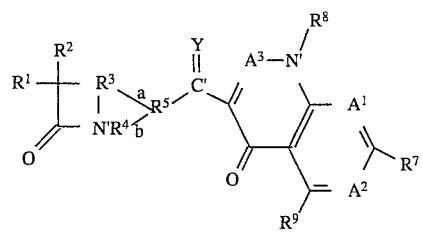

wherein
(1) $R^3$, $R^4$, and $R^5$, together with bonds "a" and "b", form any of a variety of lactam-containing moieties similar to those known in the art to have antimicrobial activity;
(2) A, $R^6$, $R^7$, and $R^8$ form any of a variety of quinolone or naphthyridine structures similar to those known in the art to have antimicrobial activity; and
(3) Y, together with $R^5$, form a variety of non-ester linking moieties between the lactam-containing moiety and the quinolone moiety.

35 Claims, No Drawings

OTHER PUBLICATIONS

Demuth, T. P., et al., "Synthesis and Antibacterial Activity of New C-10 Quinolonyl–Cephem Esters", *The Journal of Antibiotics*, vol. 44, No. 2, pp. 200–209, Feb. 1991.

Uglesic et al., "New Semisynthetic Penicillins", *Advan. Antimicrob. Antineoplastic Chemother., Proc. Int. Congr. Chemother., 7th, Meeting Date* 1971, vol. 1, 997 (1972) (Chemical Abstracts 79:61968).

O'Callaghan, et al., "A New Cephalosporin with a Dual Mode of Action", 10 *Antimicrobial Agents and Chemotherapy* 245 (1976).

Greenwood et al., "Dual–Action Cephalosporin Utilizing a Novel Therapeutic Principle", 10 *Antimicrobial Agents and Chemotherapy* 249 (1976).

Yamada et al., "New Broad–Spectrum Cephalosporins with Antipseudomonal Activity", 36 *J. Antibiotics* 532 (1983) (*Chemical Abstracts* 99:87869).

Hirose et al., "Desulfurization of 7–Aminodeacetoxycephalosporanic Acid", 104 *Yakugaku Zasshi* 302 (1984) (*Chemical Abstract* 101:110596).

Cimarusti et al., "Monocyclic β–Lactam Antibiotics", 4 *Medicinal Research Reviews* 1 (1984).

Dürckheimer et al., "Recent Developments in the Field of β–Lactam Antibiotics", 24 *Angew. Chem. Int. Ed. Engl.* 180 (1985).

Wolfson et al., "Minireview—The Fluoroquinolones: Structures, Mechanisms of Action and Resistance, and Spectra of Activity In Vitro", 28 *Antimicrobial Agents and Chemotherapy* 581 (1985).

Mobashery et al., "Conscripting β–Lactamase for Use in Drug Delivery. Synthesis and Biological Activity of a Cephalosporin $C_{10}$–Ester of an Antibiotic Dipeptide", 108 *J. American Chemical Society* 1685 (1986).

Mobashery et al., "Reactions of *Escherichia coli* TEM β–Lactamase with Cephalothin and with $C_{10}$–Dipeptidyl Cephalosporin Esters", 261 *J. Biological Chemistry* 7879 (1986).

Rolinson, "β–Lactam antibiotics", 17 *J. Antimicrobial Chemotherapy* 5 (1986).

Wise, "MINIREVIEW—In Vitro and Pharmacokinetic Properties of the Carbapenems", 30 *Antimicrobial Agents and Chemotherapy* 343 (1986).

Mobashery et al., "Inactivation of Alanine Racemase by β–Chloro–L–alanine Released Enzymatically from Amino Acid and Peptide $C_{10}$ Esters of Deacetylcephalothin", 26 *Biochemistry* 5878 (1987).

Thabaut et al., "Beta–lactam Antibiotic—New Quinolone Combinations", 16 *Presse Med.* 2167 (1987) (*Chemical Abstracts* 108:147028).

Le Noc et al., "Activite Antibacterienne in vitro du Cefpirome en Association Avec Quatre Aminoglycosides et Deux Fluoroquinolones", 36 *Path. Biol.* 762 (1988).

McCombie et al., "Synthesis and In Vitro Activity of the Penem Antibiotics", 8 *Medicinal Research Reviews* 393 (1988).

Albrecht et al., "Dual–Action Cephalosporins: An Idea Whose Time Has Come", *Program and Abstracts of the Twenty–Eighth Interscience Conference on Antimicrobial Agents and Chemotherapy* 186 (American Society for Microbiology, 1988).

Georgopapadakou et al., "Cephalosporin–Quinolone Esters: Biological Properties", *Program and Abstracts of the Twenty–Eighth Interscience Conference on Antimicrobial Agents and Chemotherapy* 186 (American Society for Microbiology, 1988).

Christenson et al., "Hydrolysis of Ro 23–9424 by β–Lactamases", *Program and Abstracts of the Twenty–Eighth Interscience Conference on Antimicrobial Agents and Chemotherapy* 187 (American Society for Microbiology, 1988).

Christenson et al., "Mode of Action of Ro 23–9424, a Dual–Action Cephalosporin", *Program and Abstracts of the Twenty–Eighth Interscience Conference on Antimicrobial Agents and Chemotherapy* 187 (American Society for Microbiology, 1988).

Georgopapadakou et al., "Mode of Action of the Dual–Action Cephalosporin Ro 23–9424", *Program and Abstracts of the Twenty–Eighth Interscience Conference on Antimicrobial Agents and Chemotherapy* 187 (American Society for Microbiology, 1988).

Jones et al., "Antimicrobial Activity of Ro 23–9424, A Novel Ester Fusion of Fleroxacin and Desacetyl–Cefotaxime", *Program and Abstracts of the Twenty–Eighth Interscience Conference on Antimicrobial Agents and Chemotherapy* 187 (American Society for Microbiology, 1988).

Beskid et al., "In Vitro Antibacterial Activity of Dual–Action Cephalosporin Ro 23–9424 and Comparative Agents", *Program and Abstracts of the Twenty–Eighth Interscience Conference on Antimicrobial Agents and Chemotherapy* 187 (American Society for Microbiology, 1988).

Beskid et al., "In Vivo Antibacterial Activity of Dual–Action Cephalosporin Ro 23–9424 Compared to Cefotaxime and Fleroxacin", *Program and Abstracts of the Twenty–Eighth Interscience Conference on Antimicrobial Agents and Chemotherapy* 187 (American Society for Microbiology, 1988).

Christenson et al., "Pharmacokinetcis of Ro 23–9424, a Dual–Action Cephalosporin in Animals", *Program and Abstracts of the Twenty–Eighth Interscience Conference on Antimicrobial Agents and Chemotherapy* 188 (American Society for Microbiology, 1988).

Christenson et al., "Mode of Action of Ro 23–5068, a Dual–Action Cephalosporin", *Program and Abstracts of the Twenty–Eighth Interscience Conference on Antimicrobial Agents and Chemotherapy* 188 (American Society for Microbiology, 1988).

Albrecht et al., "Dual–Action Cephalosporins: An Idea Whose Time Has Come", Poster Session: 28th Interscience Conference on Antimicrobial Agents and Chemotherapy (Oct. 24, 1988).

Georgopapadakou et al., "Cephalosporin–Quinolone Esters: Biological Properties", Poster Session: 28th Interscience Conference on Antimicrobial Agents and Chemotherapy (Oct. 24, 1988).

Christenson et al., "Hydrolysis of Ro 23–9424 by β–Lactamases", Poster Session: 28th Interscience Conference on Antimicrobial Agents and Chemotherapy (Oct. 24, 1988).

Christenson et al., "Mode of Action of Ro 23–9424, A 'Dual–Action' Cephalosporin", Poster Session: 28th Interscience Conference on Antimicrobial Agents and Chemotherapy (Oct. 24, 1988).

Georgopapadakou et al., "Mode of Action of the Dual–Action Cephalosporin Ro 23–9424", Poster Session: 28th interscience Conference on Antimicrobial Agents and Chemotherapy (Oct. 24, 1988).

Beskid et al., "In Vitro Antibacterial Activity of Dual–Action Cephalosporin Ro 23–9424 and Comparative Agents", Poster Session: 28th Interscience Conference on Antimicrobial Agents and Chemotherapy (Oct. 24, 1988).

Beskid et al., "In Vivo Antibacterial Activity of Dual-Action Cephalosporin Ro 23-9424 Compared to Cefotaxime and Fleroxacin", Poster Session: 28th Interscience Conference on Antimicrobial Agents and Chemotherapy (Oct. 24, 1988).

Christenson et al., "Pharmacokinetics of Ro 23-9424, a Dual-Action Cephalosporin, in Animals", Poster Session: 28th Interscience Conference on Antimicrobial Agents and Chemotherapy (Oct. 24, 1988).

Christenson et al., "Mode of Action of Ro 23-5068, a Dual-Action Cephalosporin", Poster Session: 28th Interscience Conference on Antimicrobial Agents and Chemotherapy (Oct. 24, 1988).

Georgopapadakou et al., "Mode of Action of the Dual-Action Cephalosporin Ro 23-9424", 33 *Antimicrobial Agents and Chemotherapy* 1067 (1989).

Cleeland et al., "Dual-Action Antibacterials: A Concept Newly Recognized for Antibacterial Chemotherapy", 6 *Antimicrobic Newsletter* 61 (1989).

Albrecht et al., "Dual-Action Cephalosporins: Cephalosporin-3'-Quaternary Quinolones", *Program and Abstracts of the Twenty-Ninth Interscience Conference on Antimicrobial Agents and Chemotherapy* (American Society for *Microbiology*, 1989).

ANTIMICROBIAL QUINOLONYL LACTAMS

This is a continuation of application Ser. No. 07/672,150 filed Mar. 19, 1991, now abandoned, which is a continuation of application Ser. No. 07/416,646, filed Oct. 10, 1989, abandoned, which is a continuation-in-part of application Ser. No. 07/261,797, filed Oct. 24, 1988, abandoned.

BACKGROUND OF THE INVENTION

This invention relates to novel antimicrobial compounds and compositions. The compounds of this invention contain, as integral substituents, a quinolone moiety and a lactam-containing moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The development of microbial resistance is one factor in the selection of an appropriate antimicrobial (particularly antibacterials), which is of increasing concern in medical science. This "resistance" can be defined as existance of organisms, within a population of a given microbial species, that are less susceptible to the action of a given antimicrobial agent. Such resistant strains may subvert the mechanism of action of a particular antimicrobial, or chemically degrade the antimicrobial before it can act. For example, bacterial resistance to beta-lactam antibacterials has arisen through development of bacterial strains that produce beta-lactamase enzymes, which degrade the antibacterial.

In part as a result of the intense use of antibacterials over extended periods of time, many highly resistant strains of bacteria have evolved. This is of particular concern in environments such as hospitals and nursing homes, which are characterized by relatively high rates of infection and intense use of antibacterials. See, e.g., W. Sanders, Jr. et al., "Inductible Beta-lactamases: Clinical and Epidemiologic Implications for Use of Newer Cephalosporins", 10 *Reviews of Infectious Diseases* 830 (1988). Indeed, the development of resistant bacterial strains has led to a concern that pathogenic bacteria may be produced that are essentially resistant to even the newest developed antibacterial agents.

The literature describes many attempts to enhance the efficacy of antimicrobials, and to overcome the development of microbial resistance. Many such attempts involve the combination of antimicrobials. For example, Thabaut et al., 16 *Presse Med.* 2167 (1987) describes combinations of pefloxacin (a quinolone) with the beta-lactams cefotaxime and cefsulodin. Lenoc et al., 36 *Path. Biol.* 762 (1988), describes combined use of cephems with aminoglycosides, and with quinolones. Japanese Patent Publication 60/06,617, published Jan. 14, 1985, also describes compositions containing beta-lactams and quinolones. O'Callaghan et al., 10 *Antimicrobial Agents and Chemotherapy* 245 (1976), describes a mercapto pyridine-substituted cephem, which is said to liberate an active antimicrobial agent when the cephalosporin is hydrolyzed by beta-lactamase. Mobashery et al., 108 *J. American Chemical Society* 1684 (1986), presents a theory of employing bacterial beta-lactamase in situ to release an antibacterially-active leaving group from the 10-position of a cephem.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology.

SUMMARY OF THE INVENTION

The present invention provides compounds of the formula:

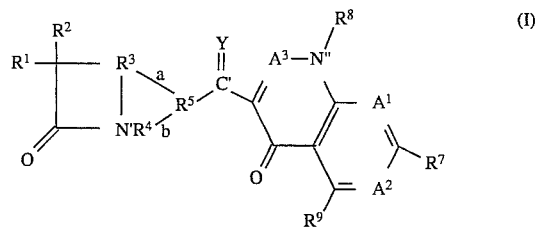

wherein (A) $R^1$ is hydrogen, halogen, alkyl, alkenyl, heteroalkyl, a carbocyclic ring, a heterocyclic ring, $R^{10a}$—O—, $R^{10a}$CH=N—, $(R^{10})(R^{11})$N—, $R^{12}$—C(=CHR$^{15}$)—C(=O)NH—, $R^{12}$—C(=NO—R$^{14}$)—C(=O)NH—, or $R^{13}$—(CH$_2$)$_m$—C(=O)NH—; where (1) m is an integer from 0 to 9;

(2) $R^{10}$ and $R^{11}$ are, independently, $R^{10a}$ where $R^{10a}$ is hydrogen, alkyl, alkenyl, a carbocyclic ring, or a heterocyclic ring substituent; or $R^{10}$ and $R^{11}$ together comprise a heterocyclic ring including the nitrogen to which they are bonded;

(3) $R^{12}$ is hydrogen, alkyl, alkenyl, heteroalkyl, heteroalkenyl, a carbocyclic ring, or a heterocyclic ring;

(4) $R^{13}$ is $R^{12}$, —$Z^1$, or —CH($Z^2$)($R^{12}$);

(5) $R^{14}$ is $R^{12}$, arylalkyl, heteroarylalkyl, —C($R^{17}$)($R^{18}$)COOH, —C(=O)O—$R^{12}$, or —C(=O)NH—$R^{12}$, where $R^{17}$ and $R^{18}$ are, independently, $R^{12}$ or together comprise a carbocyclic ring or a heterocyclic ring including the carbon atom to which $R^{17}$ and $R^{18}$ are bonded;

(6) $R^{15}$ is $R^{14}$, halogen, —$Z^1$, or —CH($Z^2$)($R^{12}$);

(7) $Z^1$ is —C(=O)O$R^{16}$, —C(=O)$R^{16}$, —N($R^{19}$)$R^{16}$, —S(O)$_p$$R^{24}$, or —O$R^{24}$; and $Z^2$ is $Z^1$ or —OH, —SH, or —SO$_3$H;

(a) p is an integer from 0 to 2;

(b) $R^{19}$ is hydrogen; alkyl; alkenyl; heteroalkyl; heteroalkenyl; a carbocyclic ring; a heterocyclic ring; —SO$_3$H; —C(=O)$R^{20}$; or, when $R^{13}$ is —CH($Z^2$)($R^{12}$) and $Z^2$ is —N($R^{19}$)$R^{16}$, $R^{19}$ may comprise a moiety bonded to $R^{16}$ to form a heterocyclic ring; and (c) $R^{20}$ is $R^{12}$, NH($R^{12}$), N($R^{12}$)($R^{21}$), O($R^{21}$), or S($R^{21}$); where $R^{21}$ is alkyl, alkenyl, a carbocyclic ring, a heterocyclic ring, or when $R^{20}$ is N($R^{12}$)($R^{21}$) $R^{21}$ may be a moiety bonded to $R^{12}$ to form a heterocyclic ring; and (8) $R^{16}$ is $R^{24}$ or hydrogen; where $R^{24}$ is alkyl; alkenyl; arylalkyl; heteroalkyl; heteroalkenyl; heteroarylalkyl; a carbocyclic ring; a heterocyclic ring; or, when $Z^1$ is N($R^{19}$)$R^{16}$ and $R^{16}$ is $R^{24}$, $R^{16}$ and $R^{19}$ may together comprise a heterocyclic ring including the nitrogen atom to which $R^{19}$ is bonded;

(B) $R^2$ is hydrogen, halogen, alkoxy, or $R^{22}$C(=O)NH—, where $R^{22}$ is hydrogen or alkyl;

(C) bond "a" is a single bond or is nil; and bond "b" is a single bond, a double bond, or is nil; except bond "a" and bond "b" are not both nil;

(D) $R^3$ is —C($R^{10a}$)—, or —CH$_2$—$R^{23}$—; where $R^{23}$ is —C($R^{10a}$), —O—, or —N—, and $R^{23}$ is directly bonded to N' in Formula (I) to form a 5-membered ring; except, if bond "a" is nil, then $R^3$ is (1) —C($R^{10a}$)($Z^3$)—, where (i) $Z^3$ is —$R^{16}$, —O$R^{25}$; —S(O)$_r$$R^{25}$; where r is an integer from 0 to 2; —OC(=O)$R^{25}$; or —N($R^{25}$)$R^{26}$;

(ii) $R^{25}$ and $R^{26}$ are, independently, alkyl, alkenyl, carbocyclic ring or heterocyclic ring substituents; or $R^{25}$ and $R^{26}$ together comprise a heterocyclic ring including the nitrogen atom to which $R^{25}$ and $R^{26}$ are bonded; or (2) —CH$_2$—$R^{27}$—; where $R^{27}$ is —C($R^{10a}$)($R^{16}$), —O—, or —N$R^{10}$, and $R^{27}$ is directly bonded to N' in Formula (I) to form a 5-membered ring;

(E) (1) if bond "b" is a single bond, $R^4$ is —CH($R^{28}$)—; or, if bond "a" is nil; —C(O)NHSO$_2$—; —C*($R^{28}$)—; if $R^5$ contains an $R^{32}$ moiety; where $R^{28}$ is hydrogen or COOH, and C* is linked to $R^{32}$ to form a 3-membered ring;

(2) if bond "b" is a double bond, $R^4$ is —C($R^{28}$)=; or (3) if bond "b" is nil, $R^4$ is hydrogen, —SO$_3$H, —PO(O$R^{29}$)OH, —C(O)NHSO$_2$N($R^{29}$)($R^{30}$), —OSO$_3$H, —CH($R^{30}$)COOH, or —OCH($R^{29}$)COOH; where $R^{29}$ is hydrogen, alkyl, alkenyl, a carbocyclic ring, or a heterocyclic ring; and $R^{30}$ is hydrogen, alkyl, alkenyl, or —NH$R^{10a}$; or, if $R^4$ is —C(O)NHSO$_2$N($R^{29}$)($R^{30}$), $R^{29}$ and $R^{30}$ may together comprise a heterocyclic ring including the nitrogen to which $R^{29}$ and $R^{30}$ are bonded; and (F) (1) if bond "a" or bond "b" is nil, then $R^5$ is X;

(2) if bond "a" and "b" are single bonds, $R^5$ is —W—C'''=C($R^{10a}$)—$R^{31}$—X—, or —W—C'''($R^{32}$)—$R^{31}$—X—; or (3) if bond "a" is a single bond and bond "b" is a double bond, $R^5$ is —C($R^{10a}$)($R^{33}$)—W—C'''—$R^{31}$—X—; —W—C($R^{10a}$)($R^{33}$)—C'''—$R^{31}$—X—; or —W—C'''—$R^{31}$—X—; where (a) W is O; S(O)$_s$, where s is an integer from 0 to 2; or C($R^{33}$), where $R^{33}$ is hydrogen, alkyl or alkoxy;

(b) $R^{31}$ is nil, alkyl, alkenyl, a carbocyclic ring, or a heterocyclic ring;

(c) $R^{32}$ is hydrogen; alkyl; alkenyl; —COOH; or, if $R^4$ is —C*($R^{28}$), $R^{32}$ may be linked to C* to form a 3-membered carbocyclic ring;

(d) X is X' or $Z^4$—$R^{34}$—X', where (1) $Z^4$ is —O—; —S(O)$_t$—, where t is an integer of 0 to 2; or —N$R^{36}$—;

(2) X' is oxygen, sulfur, or $R^{35}$—N$R^{36}$;

(3) $R^{34}$ is alkyl, alkenyl, heteroalkyl, heteroalkenyl, a carbocyclic ring, or a heterocyclic ring;

(4) $R^{35}$ is nil, N($R^{36}$), or oxygen;

(5) $R^{36}$ is hydrogen, alkyl, alkenyl, a carbocyclic ring, or a heterocyclic ring;

(e) C''' is bonded to $R^4$ to form a 5- or 6-membered ring;

(G) (1) if X' is sulfur or $R^{35}$—N$R^{36}$, Y is oxygen or Y'; or (2) if X' is oxygen, Y is Y'; where Y' is sulfur or —N$R^{39}$; where $R^{39}$ is hydrogen, alkyl, oxygen, sulfur, or N($R^{10a}$), or if $A^3$ is C($R^{41}$), then $R^{39}$ and $R^{41}$ may together comprise a heterocyclic ring;

(H) (1) $A^1$ is N or C($R^{40}$); where $R^{40}$ is hydrogen, hydroxy, alkoxy, nitro, cyano, halogen, alkyl, or N($R^{10}$)($R^{11}$);

(2) $A^2$ is N or C($R^6$); where $R^6$ is hydrogen or halogen;

(3) $A^3$ is N or C($R^{41}$); where $R^{41}$ is hydrogen;

(4) $R^8$ is hydrogen, alkyl, a carbocyclic ring, a heterocyclic ring, alkoxy, hydroxy, alkenyl, arylalkyl, or N($R^{10}$)($R^{11}$);

(5) $R^7$ is hydrogen, halogen, alkyl, a carbocyclic ring, or a heterocyclic ring; and (7) $R^9$ is hydrogen, halogen, nitro, or N($R^{10}$)($R^{11}$);

(I) except that (1) when $A^1$ is C($R^{40}$), $R^8$ and $R^{40}$ may together comprise a heterocyclic ring including N" and $A^1$;

(2) when $A^2$ is C($R^6$), $R^6$ and $R^7$ may together comprise —O—(CH$_2$)$_n$—O—, where n is an integer from 1 to 4; and (3) when $A^3$ is C($R^{41}$), $R^8$ and $R^{41}$ may together comprise a heterocyclic ring including N" and the adjacent carbon to which $R^{41}$ is bonded;

and pharmaceutically-acceptable salts and biohydrolyzable esters thereof, and hydrates thereof.

DESCRIPTION OF THE INVENTION

The present invention encompasses certain novel quinolonyl lactams, methods for their manufacture, dosage forms, and methods of administering the quinolonyl lactams to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

Quinolonyl Lactams

The compounds of this invention, herein referred to as "quinolonyl lactams", encompass any of a variety of lactam-containing moieties linked, by a non-ester linking moiety, to the 3-carboxy group of a quinolone moiety. These compounds include those of the formula:

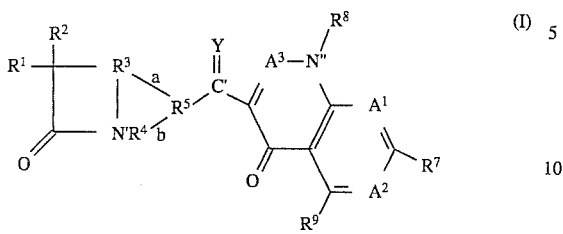

wherein
(a) $R^1$ is hydrogen, halogen, alkyl, alkenyl, heteroalkyl, a carbocyclic ring, a heterocyclic ring, $R^{10a}$—O—, $R^{10a}$CH=N—, $(R^{10}(R^{11})N$—, $R^{12}$—C(=CHR$^{15}$)—C(=O)NH—, or (preferably) $R^{12}$—C(=NO—R$^{14}$)—C(=O)NH—, or $R^{13}$—(CH$_2$)$_m$—C(=O)NH—; where
  (1) m is an integer from 0 to 9 (preferably 0 to 3);
  (2) $R^{10}$ and $R^{11}$ are, independently, $R^{10a}$ where $R^{10a}$ is hydrogen, alkyl, alkenyl, carbocyclic ring, or heterocyclic ring substituents; or $R^{10}$ and $R^{11}$ together comprise a heterocyclic ring including the nitrogen to which they are bonded;
  (3) $R^{12}$ is hydrogen, alkyl, alkenyl, heteroalkyl, heteroalkenyl, a carbocyclic ring, or a heterocyclic ring (preferably alkyl, a carbocyclic ring, or a heterocyclic ring);
  (4) $R^{13}$ is $R^{12}$, —$Z^1$; or —CH($Z^2$)($R^{12}$);
  (5) $R^{14}$ is $R^{12}$, arylalkyl, heteroarylalkyl, —C($R^{17}$)($R^{18}$)COOH, —C(=O)O—$R^{12}$, or —C(=O)NH—$R^{12}$, where $R^{17}$ and $R^{18}$ are, independently, $R^{12}$ or together comprise a carbocyclic ring or a heterocyclic ring including the carbon atom to which $R^{17}$ and $R^{18}$ are bonded (preferably $R^{12}$ or —C($R^{17}$)($R^{18}$)COOH);
  (6) $R^{15}$ is $R^{14}$, halogen, —$Z^1$, or —CH($Z^2$)($R^{12}$) (preferably $R^{14}$ or halogen);
  (7) $Z^1$ is —C(=O)O$R^{16}$, —C(=O)$R^{16}$, —N($R^{19}$)$R^{16}$, —S(O)$_p$$R^{24}$, or —O$R^{24}$; and $Z^2$ is $Z^1$ or —OH, —SH, or —SO$_3$H;
    (a) p is an integer from 0 to 2 (preferably 0);
    (b) $R^{19}$ is hydrogen; alkyl; alkenyl; heteroalkyl; heteroalkenyl; a carbocyclic ring; a heterocyclic ring; —SO$_3$H; —C(=O)$R^{20}$; or, when $R^{13}$ is —CH($Z^2$)($R^{12}$) and $Z^2$ is —N($R^{19}$)$R^{16}$, $R^{19}$ may comprise a moiety bonded to $R^{16}$ to form a heterocyclic ring; and
    (c) $R^{20}$ is $R^{12}$, NH($R^{12}$), N($R^{12}$)($R^{21}$), O($R^{21}$), or S($R^{21}$) (preferably $R^{12}$, NH($R^{12}$), N($R^{12}$)($R^{21}$)); where $R^{21}$ is alkyl, alkenyl, a carbocyclic ring, a heterocyclic ring, or (preferably) when $R^{20}$ is N($R^{12}$)($R^{21}$) $R^{21}$ may be a moiety bonded to $R^{12}$ to form a heterocyclic ring; and
  (8) $R^{16}$ is $R^{24}$ or hydrogen; where $R^{24}$ is alkyl; alkenyl; arylalkyl; heteroalkyl; heteroalkenyl; heteroarylalkyl; a carbocyclic ring; a heterocyclic ring; or, when $Z^1$ is N($R^{19}$)$R^{16}$ and $R^{16}$ is $R^{24}$, $R^{16}$ and $R^{19}$ may together comprise a heterocyclic ring including the nitrogen atom to which $R^{19}$ is bonded (preferably hydrogen, alkyl, a carbocyclic ring or a heterocyclic ring);
(B) $R^2$ is hydrogen, halogen, alkoxy, or $R^{22}$C(=O)NH— (preferably hydrogen or alkoxy), where $R^{22}$ is hydrogen or alkyl (preferably hydrogen);

(C) bond "a" is a single bond or is nil; and bond "b" is a single bond, a double bond, or is nil; except bond "a" and bond "b" are not both nil;
(D) $R^3$ is —C($R^{10a}$)—, or —CH$_2$—$R^{23}$— (preferably —C($R^{10a}$)—); where $R^{23}$ is —C($R^{10a}$), —O—, or —N—, and $R^{23}$ is directly bonded to N' in Formula (I) to form a 5-membered ring; except, if bond "a" is nil, then $R^3$ is
  (1) (preferably) —C($R^{10a}$)($Z^3$)—, where
    (i) $Z^3$ is —$R^{16}$; —O$R^{25}$; —S(O)$_r$$R^{25}$, where r is an integer from 0 to 2 (preferably 0); —OC(=O)$R^{25}$; or —N($R^{25}$)$R^{26}$;
    (ii) $R^{25}$ and $R^{26}$ are, independently, alkyl, alkenyl, carbocyclic ring or heterocyclic ring substituents; or $R^{25}$ and $R^{26}$ together comprise a heterocyclic ring including the nitrogen atom to which $R^{25}$ and $R^{26}$ are bonded; or
  (2) —CH$_2$—$R^{27}$—; where $R^{27}$ is —C($R^{10a}$)($R^{16}$), —O—, or —NR$^{10}$, and $R^{27}$ is directly bonded to N' in Formula (I) to form a 5-membered ring;
(E) (1) if bond "b" is a single bond, $R^4$ is (preferably) —CH($R^{28}$)—; or, if bond "a" is nil; —C(O)NHSO$_2$—; or —C*($R^{28}$)—; if $R^5$ contains a $R^{32}$ moiety; where $R^{28}$ is hydrogen or (preferably) COOH, and C* is linked to $R^{32}$ to form a 3-membered ring;
  (2) if bond "b" is a double bond, $R^4$ is —C($R^{28}$)=; or
  (3) if bond "b" is nil, $R^4$ is hydrogen, —SO$_3$H, —PO(O$R^{29}$)OH, —C(O)NHSO$_2$N($R^{29}$)($R^{30}$), —OSO$_3$H, —CH($R^{30}$)COOH, or —OCH($R^{29}$)COOH (preferably —SO$_3$H or —C(O)NHSO$_2$N($R^{29}$)($R^{30}$)); where $R^{29}$ is hydrogen, alkyl, alkenyl, a carbocyclic ring, or a heterocyclic ring; and $R^{30}$ is hydrogen, alkyl, alkenyl, or —NHR$^{10a}$; or (preferably), if $R^4$ is —C(O)NHSO$_2$N($R^{29}$)($R^{30}$), $R^{29}$ and $R^{30}$ may together comprise a heterocyclic ring including the nitrogen to which $R^{29}$ and $R^{30}$ are bonded; and
(F) (1) if bond "a" or bond "b" is nil, then $R^5$ is X;
  (2) if bond "a" and "b" are single bonds, $R^5$ is —W—C'''=C($R^{10a}$)—$R^{31}$—X—, or —W—C'''($R^{32}$)—$R^{31}$—X—; or
  (3) if (preferably) bond "a" is a single bond and bond "b" is a double bond, $R^5$ is —C($R^{10a}$)($R^{33}$)—W—C'''—$R^{31}$—X—; or (preferably) —W—C($R^{10a}$)($R^{33}$)—C'''—$R^{31}$—X—; or —W—C'''—$R^{31}$—X—; where
    (a) W is O; S(O)$_s$, where s is an integer from 0 to 2 (preferably 0); or C($R^{33}$), where $R^{33}$ is hydrogen, alkyl or alkoxy;
    (b) $R^{31}$ is nil, alkyl, alkenyl, a carbocyclic ring, or a heterocyclic ring;
    (c) $R^{32}$ is hydrogen; alkyl; alkenyl; —COOH; or, if $R^4$ is —C*($R^{28}$), $R^{32}$ may be linked to C* to form a 3-membered carbocyclic ring;
    (d) X is X' or $Z^4$—$R^{34}$—X', where
      (1) $Z^4$ is —O—; —S(O)$_t$—, where t is an integer of 0 to 2 (preferably 0); or —NR$^{36}$—;
      (2) X' is oxygen, sulfur, or $R^{35}$—NR$^{36}$;
      (3) $R^{34}$ is alkyl, alkenyl, heteroalkyl, heteroalkenyl, a carbocyclic ring, or a heterocyclic ring (preferably alkyl or alkenyl);
      (4) $R^{35}$ is nil, N($R^{36}$), or oxygen;
      (5) $R^{36}$ is hydrogen, alkyl, alkenyl, a carbocyclic ring, or a heterocyclic ring;
    (e) C''' is bonded to $R^4$ to form a 5- or 6-membered ring;

(G) (1) if X' is sulfur or $R^{35}$—$NR^{36}$, Y is Y' or (preferably) oxygen; or
(2) if X' is oxygen, Y is Y'; where Y' is sulfur or (preferably) —$NR^{39}$; where $R^{39}$ is hydrogen, alkyl, oxygen, sulfur, or $N(R^{10a})$, or if $A^3$ is $C(R^{41})$, then $R^{39}$ and $R^{41}$ may together comprise a heterocyclic ring;
(H) (1) $A^1$ is N or $C(R^{40})$; where $R^{40}$ is hydrogen, hydroxy, alkoxy, nitro, cyano, halogen, alkyl, or $N(R^{10})(R^{11})$ (preferably hydrogen or halogen);
(2) $A^2$ is N or (preferably) $C(R^6)$; where $R^6$ is hydrogen or halogen;
(3) $A^3$ is N or (preferably) $C(R^{41})$; where $R^{41}$ is hydrogen;
(4) $R^8$ is hydrogen, alkyl, a carbocyclic ring, a heterocyclic ring, alkoxy, hydroxy, alkenyl, arylalkyl, or $N(R^{10})(R^{11})$ (preferably alkyl or a carbocyclic ring);
(5) $R^7$ is hydrogen, halogen, alkyl, a carbocyclic ring, or a heterocyclic ring (preferably a heterocyclic ring); and
(7) $R^9$ is hydrogen, halogen, nitro, or $N(R^{10})(R^{11})$ (preferably hydrogen);
(I) except that
(1) when $A^1$ is $C(R^{40})$, $R^8$ and $R^{40}$ may together comprise a heterocyclic ring including N" and $A^1$;
(2) when $A^2$ is $C(R^6)$, $R^6$ and $R^7$ may together comprise —O—$(CH_2)_n$—O—, where n is an integer from 1 to 4; and
(3) when $A^3$ is $C(R^{41})$, $R^8$ and $R^{41}$ may together comprise a heterocyclic ring including N" and the adjacent carbon to which $R^{41}$ is bonded;
and pharmaceutically-acceptable salts and biohydrolyzable esters thereof, and hydrates thereof.

Definitions and Usage of Terms

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolonyl, and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred aryl alkyl sgroups include benzyl and phenylehtyl.

"Arylamino" is an amine radical substituted with an aryl group (i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkyl acyl groups include (for example) acetyl, formyl, and propionyl.

"Acyloxy" is an oxygen radical having an acyl substituent (i.e., —O—acyl ); for example, —OC(=O)—alkyl.

"Acylamino" is an amino radical having an acyl substituent (i.e., —N—acyl ); for example, —NH—C(=O)—alkyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as choride salts).

A "biohydrolyzable ester" is an ester of a quinolonyl lactam that does not essentially interfere with the antimicrobial activity of the compounds, or that are readily metabolized by a human or lower animal subject to yield an antimicrobially-active quinolonyl lactam. Such esters include those that do not interfere with the biological activity of quinolone antimicrobials or beta-lactam antimicrobials (cephems, for example). Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^{10a}$ substituent is defined as a potential substituent of $R^{10a}$ but is also incorporated into the definition of other substituents (such as $R^3$, $R^8$, and $R^9$). As used herein, such a radical is independently selected each time it is used (e.g., $R^{10a}$ need not be alkyl in all occurrences in defining a given compound of this invention).

Lactam-containing Moieties

Groups $R^3$, $R^4$, and $R^5$, together with bonds "a" and "b", form any of a variety of lactam-containing moieties known in the art to have antimicrobial activity. Such moieties wherein either bond "a" or bond "b" are nil (i.e., do not exist) are monocyclic; if both bonds exist, the structures are bicyclic.

Preferred lactam moieties include the cephems, oxacephems, and carbacephems of the representative formula:

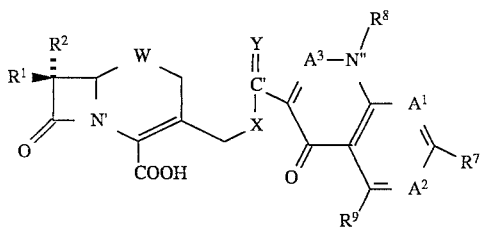

wherein bond "a" is a single bond; bond "b" is a double bond; $R^3$ is —C($R^{10a}$)—, where $R^{10a}$ is hydrogen; $R^4$ is —CH($R^{28}$), where $R^{28}$ is COOH; and $R^5$ is —W—C($R^{10a}$)($R^{33}$)—C'''$R^{31}$—X—, where $R^{10a}$ and $R^{33}$ are hydrogen, $R^{31}$ is methylene, and W is S (for cephems), O (for oxacephems), or C($R^{33}$) (for carbacephems).

Other preferred lactam moieties include the isocephems and iso-oxacephems of the representative formula:

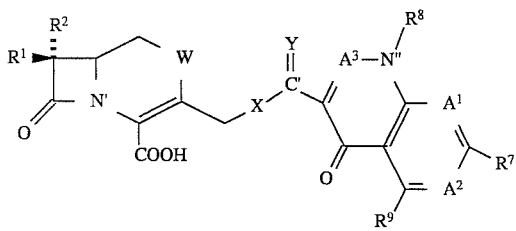

wherein bond "a" is a single bond; bond "b" is a double bond; $R^3$ is —C($R^{10a}$) where $R^{10a}$ is hydrogen; $R^4$ is —C($R^{28}$), where $R^{28}$ is COOH; and $R^5$ is —C($R^{10a}$)($R^{33}$)— W—C'''—$R^{31}$—X— where $R^{10a}$ and $R^{33}$ are each hydrogen, $R^{31}$ is methylene, and W is S (for isocephems) or O (for iso-oxacephems).

Other preferred lactam-containing moieties include the penems, carbapenems and clavems, of the representative formula:

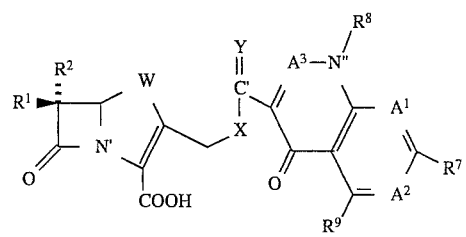

wherein bond "a" is a single bond; bond "b" is a double bond; $R^3$ is —C($R^{10a}$), where $R^{10a}$ is hydrogen; $R^4$ is —C($R^{28}$)=, where $R^{28}$ is COOH; and $R^5$ is —W—C'''— $R^{31}$—X—, where $R^{31}$ is methylene, and W is S (for penems), C($R^{33}$) (for carbapenems), or O (for clavems). Such lactam moieties are described in the following articles, all incorporated by reference herein: R. Wise, "In Vitro and Pharmacokinetic Properties of the Carbapenems", 30 *Antimicrobial Agents and* Chemotherapy 343 (1986); and S. McCombie et al., "Synthesis and In Vitro Activity of the Penem Antibiotics", 8 *Medicinal Researth Reviews* 393 (1988).

Other preferred lactam-containing moieties of this invention include the penicillins of the representative formula:

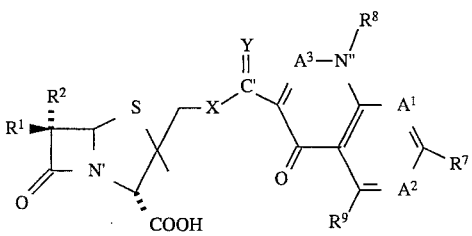

wherein bond "a" is a single bond, bond "b" is a single bond; $R^3$ is —C($R^{10a}$)—, where $R^{10a}$ is hydrogen; $R^4$ is —CH($R^{28}$)— where $R^{28}$ is COOH; and $R^5$ is —W—C'''($R^{32}$)—$R^{31}$—X— where $R^{32}$ is methyl, $R^{31}$ is methylene, and W is S.

Other preferred lactam-containing moieties include the monocyclic beta-lactams, of the representative formula:

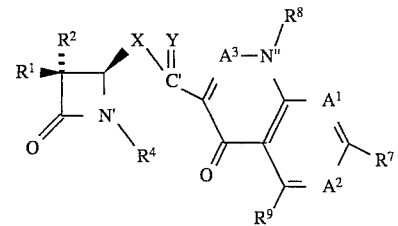

wherein bond "a" is a single bond; bond "b" is nil; $R^3$ is —C($R^{10a}$)—, where $R^{10a}$ is hydrogen; $R^5$ is X; and $R^4$ is —SO$_3$H (for a monobactam), —PO(OR$^{34}$)OH (for a monophospham); —C(O)NHSO$_2$N($R^{34}$)($R^{35}$) (for a monocarbam), —OSO$_3$H (for a monosulfactam), —CH($R^{35}$)COOH (for nocardicins), or —OCH($R^{34}$)COOH. Such lactam moieties are described in C. Cimarusti et al., "Monocyclic 8-lactam Antibiotics", 4 *Medicinal Research Reviews* 1 (1984), incorporated by reference herein.

Other preferred lactam moieties include the monocyclic beta-lactams of the representative formula:

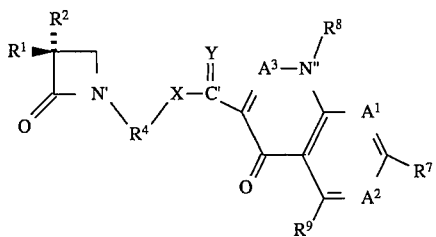

wherein bond "a" is nil, bond "b" is a single bond; $R^3$ is —$C(R^{10a})(R^{29})$— where both $R^{10a}$ and $R^{29}$ are hydrogen; and $R^5$ is X.

Other preferred lactam moieties include the clavams of the representative formula:

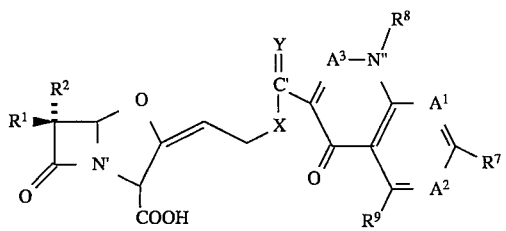

wherein bond "a" is a single bond; bond "b" is a single bond; $R^3$ is —$C(R^{10a})$—, where $R^{10a}$ is hydrogen; $R^4$ is —$CH(R^{28})$—, where $R^{28}$ is COOH; and $R^5$ is W—C'''=C—$(R^{10a})$—$R^{31}$—X—, where $R^{10a}$ is hydrogen and $R^{31}$ is methylene, and W is O.

Other preferred lactam moieties include the 2,3-methylenopenams and -carbapenams of the representative formula:

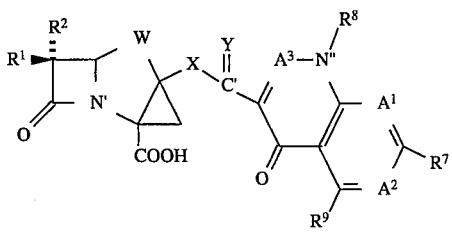

wherein bond "a" is a single bond; bond "b" is a single bond; $R^3$ is —$C(R^{10a})$—, where $R^{10a}$ is hydrogen; $R^4$ is —$C^*(R^{28})$, where $R^{28}$ is COOH; and $R^5$ is W—C'''$(R^{32})$—$R^{31}$—X—, where $R^{31}$ is nil, $R^{32}$ is linked to C* to form a 3-membered carbocyclic ring, and W is $C(R^{33})$ or sulfur.

Lactam moieties of this invention also include the lactivicin analogs of the representative formula:

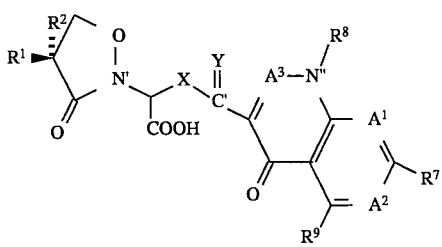

wherein bond "a" is nil; bond "b" is a single bond; $R^3$ is —$CH_2$—$R^{32}$, where $R^{32}$ is O; $R^4$ is —$CH(R^{28})$—, where $R^{28}$ is COOH; and $R^5$ is X.

Other lactam moieties include the pyrazolidinones of the representative formula:

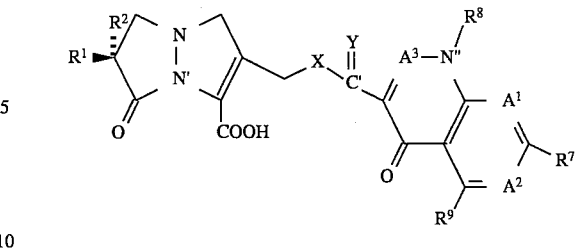

wherein bond "a" is a single bond; bond "b" is a double bond; $R^3$ is —$CH_2$—$R^{28}$—, where $R^{28}$ is —N—; $R^4$ is —$C(R^{28})$—, where $R^{28}$ is COOH; and $R^5$ is W—C'''—$R^{31}$—X—, where $R^{31}$ is methylene, and W is $C(R^{33})$.

Other lactam moieties include the gamma-lactams of the representative formula:

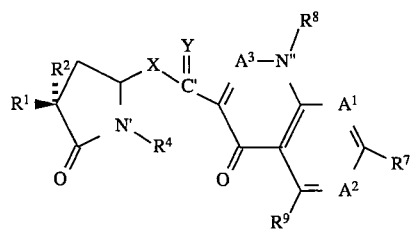

wherein bond "a" is a single bond; bond "b" is nil; $R^3$ is —$CH_2$—$R^{28}$—, where $R^{28}$ is —$C(R^{10a})$ and $R^{10a}$ is hydrogen; $R^4$ is —$SO_3H$, —$PO(OR^{34})OH$, —$C(O)NHSO_2N(R^{34})(R^{35})$, —$OSO_3H$, —$CH(R^{35})COOH$, or —$OCH(R^{34})COOH$; and $R^5$ is X.

Preferred lactam-containing moieties include cephems, isocephems, iso-oxacephems, oxacephems, carbacephems, penicillins, penems, carbapenems, and monocyclic beta-lactams. Particularly preferred are cephems, penems, carbapenems and monocyclic beta-lactams.

$R^1$ is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams.

Appropriate $R^1$ groups will be apparent to one of ordinary skill in the art. Many such $R^1$ groups are known in the art, as described in the following documents (all of which are incorporated by reference herein): *Cephalosporins and Penicillins: Chemistry and Biology* (E. Flynn, editor, 1972); *Chemistry and Biology of b-Lactam Antibiotics* (R. Morin et al., editors, 1987); "The Cephalosporin Antibiotics: Seminar-in-Print", 34 *Drugs* (Supp. 2) 1 (J. Williams, editor, 1987); *New Beta-Lactam Antibiotics: A Review from Chemistry of Clinical Efficacy of the New Cephalosporins* (H. Neu, editor, 1982); M. Sassiver et al., in *Structure Activity Relationships among the Semi-synthetic Antibiotics* (D. Perlman, editor, 1977). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavams, $R^1$ is preferably lower alkyl, or hydroxy-substituted lower alkyl. Particularly preferred $R^1$ groups include hydrogen, hydroxymethyl, ethyl, [1(R)-hydroxyethyl], [1(R)-[(hydroxysulfonyl)oxyethyl]], and [1-methyl-1-hydroxyethyl].

Except for penems, carbapenems, clavems and clavams, preferred R¹ groups are amides, such as: acetylamino, preferably substituted with aryl, heteroaryl, aryloxy, heteroarylthio and lower alkylthio substituents; arylglycylamino, preferably N-substituted with heteroarylcarbonyl and cycloheteroalkyl carbonyl substituents; aryl carbonyl amino; heteroarylcarbonyl amino; and lower alkoxyiminoacetylamino, preferably substituted with aryl and heteroaryl substituents. Particularly preferred R¹ groups include amides of the general formula R¹³—(CH₂)ₘ—C(=O)NH— and R¹³ is R¹². Examples of such preferred R¹ groups include:

[(2-amino-5-halo-4-thiazolyl)acetyl]amino;
[(4-aminopyridin-2-yl)acetyl]amino;
[[(3,5-dichloro-4-oxo-1(4H)-pyridinyl)acetyl]amino];
[[[2-(aminomethyl)phenyl]acetyl]amino];
[(1H-tetrazol-1-ylacetyl)amino];
[(cyanoacetyl)amino];
[(2-thienylacetyl)amino];
[[(2-amino-4-thiazoyl)acetyl]amino]; and
sydnone, 3-[-2-amino]-2-oxoethyl.

The following are other such preferred R¹ groups.

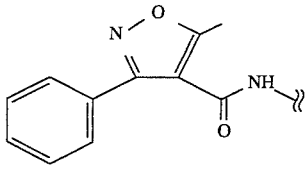

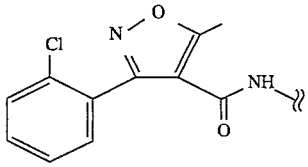

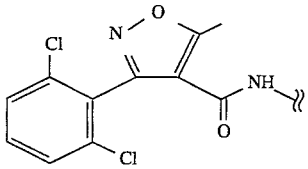

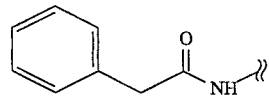

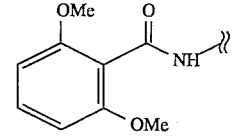

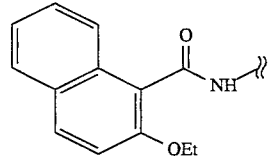

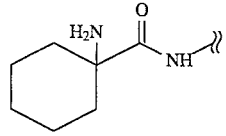

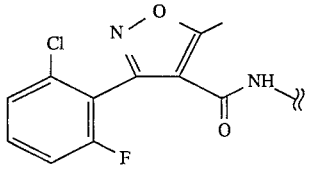

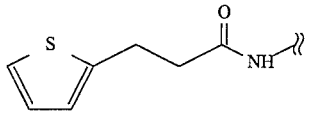

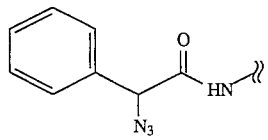

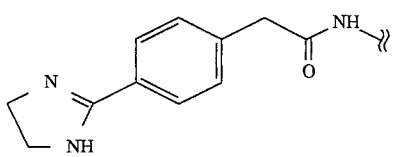

When R¹ is R¹³—(CH₂)ₘ—C(C=O)NH—, and R¹³ is —Z¹, preferred R¹ groups include the following:
[sulfamoylphenylacetyl]amino;
[[(4-pyridinylthio)acetyl]amino];
[[[(cyanomethyl)thio]acetyl]amino];
(S)-[[[(2-amino-2-carboxyethyl)thio]acetyl]amino];
[[[(trifluoromethyl)thio]acetyl]amino]; and
(E)-[[[(2-aminocarbonyl-2-fluoroethenyl)thio]acetyl]amino].

The following are other such preferred R¹ groups.

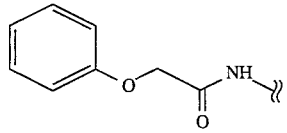

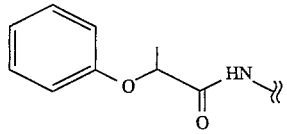

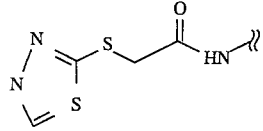

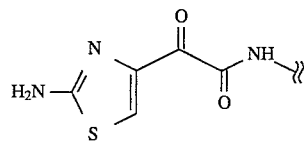

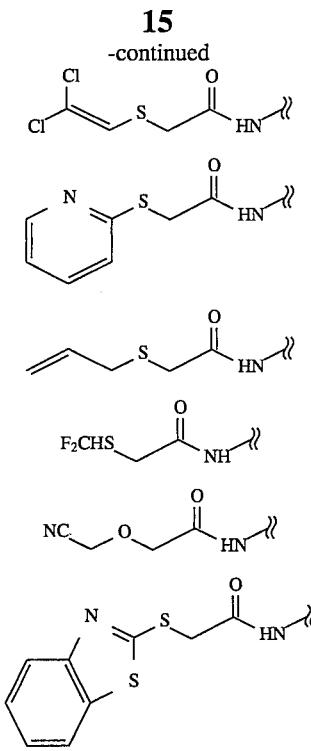

When R$^1$ is R$^{13}$—(CH$_2$)$_m$—C(=O)NH—, and R$^{13}$ is —CH(Z$^2$)(R$^{12}$), preferred R$^1$ groups include the following:

[carboxyphenylacetyl]amino;
[(phenoxycarbonyl)phenylacetyl]amino;
[4-methyl-2,3-dioxo-1-piperazinecarbonyl-D-phenylglycyl]amino;
[[[3-(2-furylmethyleneamino)-2-oxo-1-imidazolidinyl]carbonyl]amino]phenyl]acetyl]amino;
(R)-[(aminophenylacetyl)amino];
(R)-[[amino(4-hydroxyphenyl)acetyl]amino];
(R)-[(amino-1,4-cyclohexadien-1-ylacetyl)amino];
[(hydroxyphenylacetyl)amino];
(R)-[[[[(4-ethyl-2,3-dioxo-1-piperazinyl)carbonyl]amino](4-hydroxyphenyl)acetyl]amino];
(R)-[[[[(5-carboxy-2H-imidazol-4-yl)carbonyl]amino]phenylacetyl]amino];
(R)-[[[[(4-hydroxy-6-methyl-3-pyridinyl)carbonyl]amino](4-hydroxyphenyl)acetyl]amino];
(R)-[(phenylsulfoacetyl)amino];
(2R,3S)-[[2-[[(4-ethyl-2,3-dioxo-1-piperazinyl)carbonyl]amino]-3-hydroxy-1-oxobutyl]amino];
[[carboxy(4-hydroxyphenyl)acetyl]amino];
(R)-[[amino[3-[(ethylsulfonyl)amino]phenyl]acetyl]amino];
(R)-[[amino(benzo[b]thien-3-yl)acetyl]amino];
(R)-[[amino(2-naphthyl)acetyl]amino];
(R)-[[amino(2-amino-4-thiazolyl)acetyl]amino];
[[[[(6,7-dihydroxy-4-oxo-4H-1-benzopyran-3-yl)carbonyl]amino](4-hydroxyphenyl)acetyl]amino];
(R,R)-[[2-[4-[2-amino-2-carboxyethyloxycarbonyl]aminophenyl] -2- hydroxyacetyl]amino]; and
(S)-[[(5-hydroxy-4-oxo-1(4H)-pyridin-2-yl)carbonylamino(2-amino-4-thiazolyl)acetyl]amino].

The following are other such preferred R$^1$ groups.

17
-continued
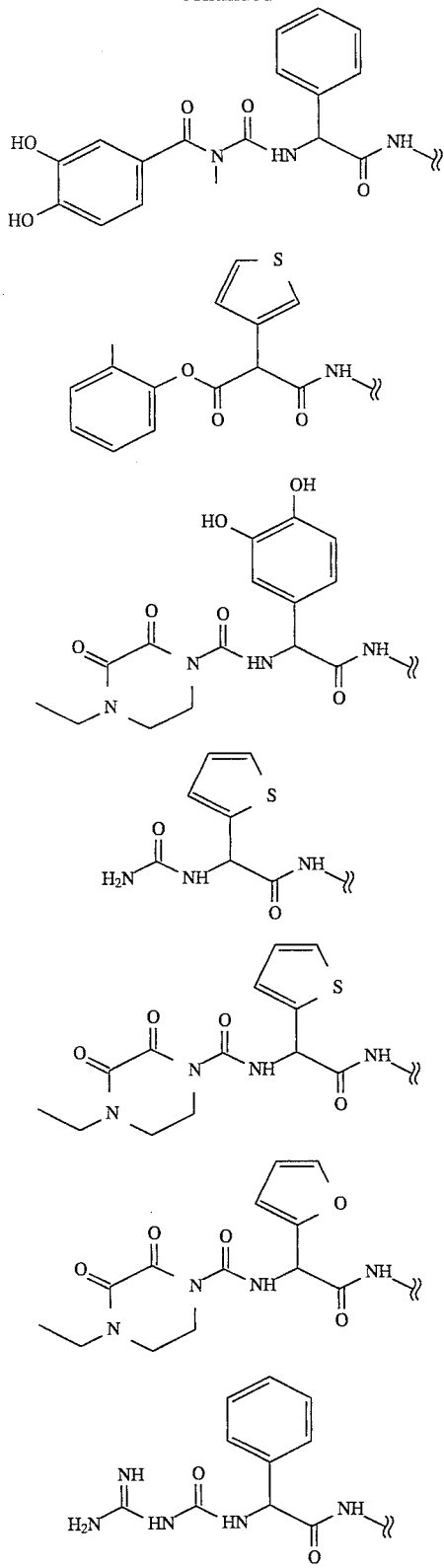
18
-continued
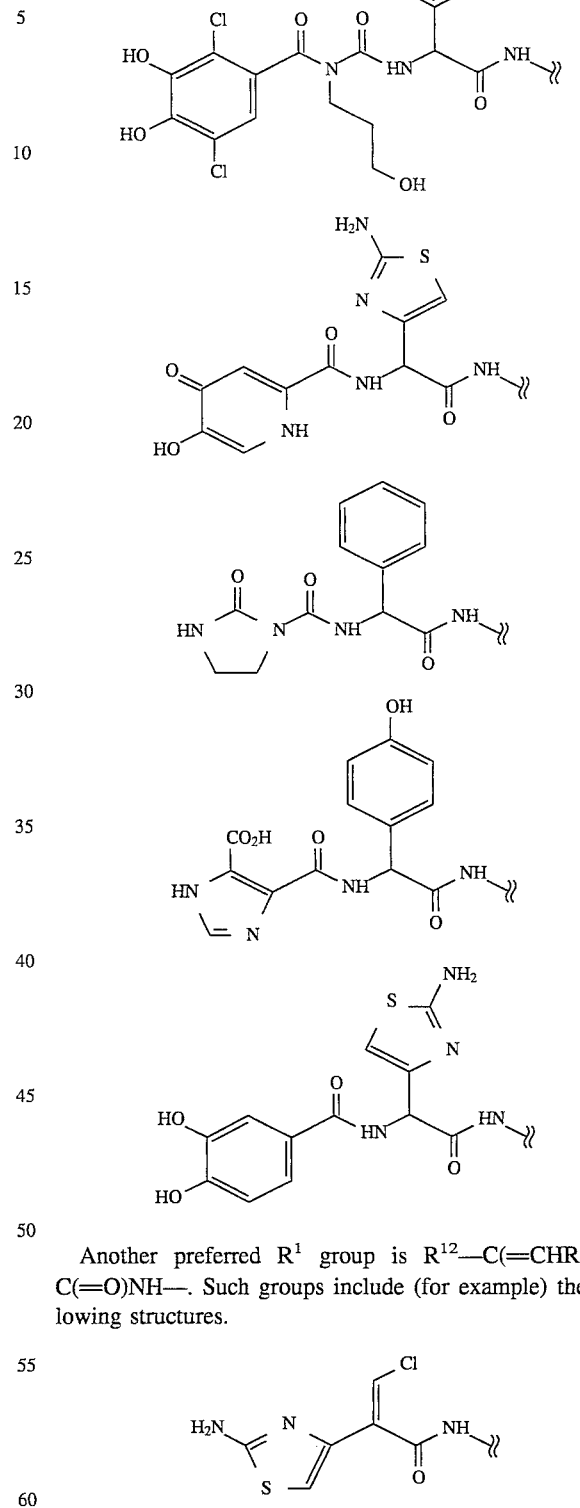
Another preferred $R^1$ group is $R^{12}$—C(=CHR$^{15}$)—C(=O)NH—. Such groups include (for example) the following structures.

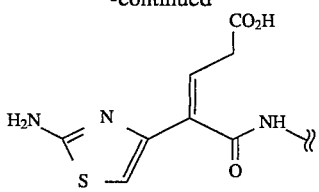

Another class of preferred $R^1$ groups (for lactam-containing moieties other than penems, carbapenems, clavems and clavams) include those of the formula:

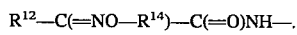

Examples of this preferred class of $R^1$ groups include:
2-phenyl-2-hydroxyiminoacetyl;
2-thienyl-2-methoxyiminoacetyl; and
2-]4-(gamma-D-glutamyloxy)phenyl]-2-hydroxyiminoacetyl.
(Z)[[(2-amino-4-thiazolyl)(methoxyimino)acetyl]amino];
[[(2-furanyl(methoxyimino)acetyl]amino];
(Z)-[[(2-amino-4-thiazolyl )][(1-carboxy-1-methyl)ethoxyimino]acetyl]amino];
(Z)-[[(2-amino-4-thiazolyl)(1-carboxymethoxyimino)acetyl]amino];
[[(2-amino-4-thiazolyl)[(1H-imidazol-4-ylmethoxy)imino] acetyl]amino];
(Z)-[[(2-amino-4-thiazolyl-3-oxide)(methoxyimino)acetyl] amino]; and
(S,Z)-[[(2-amino-4-thiazolyl)[carboxy(3,4-dihydroxyphenyl)methoxyimino]acetyl]amino].

Other preferred $R^1$ groups include the following structures.

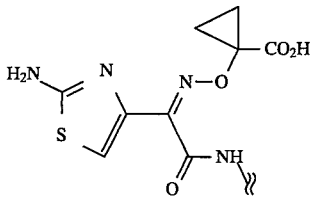

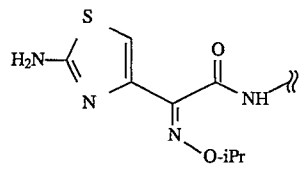

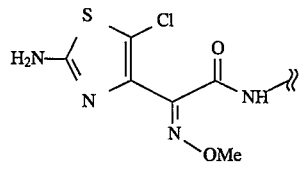

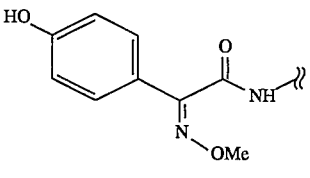

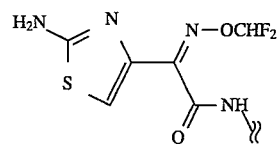

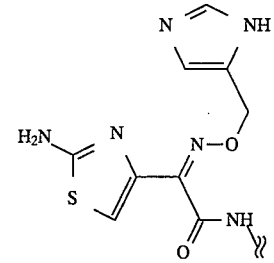

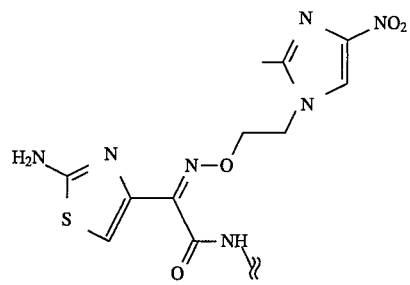

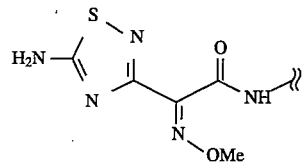

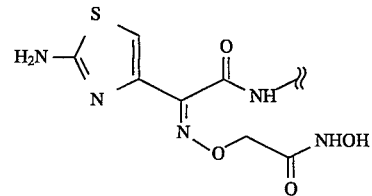

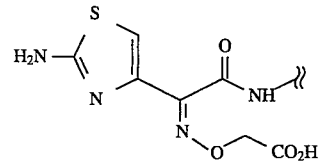

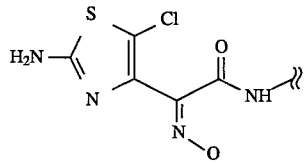

-continued

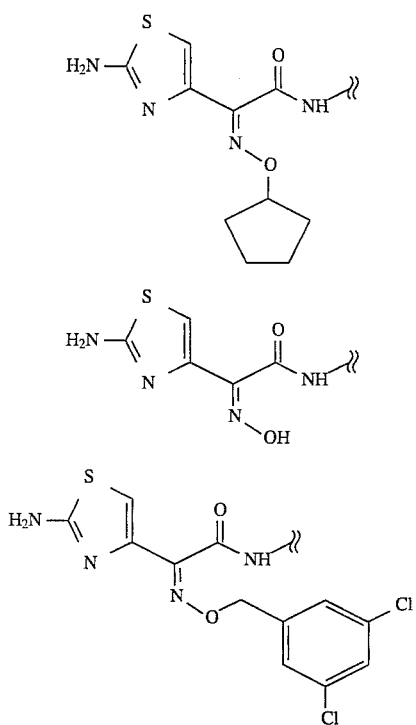

The following are other preferred R¹ groups.

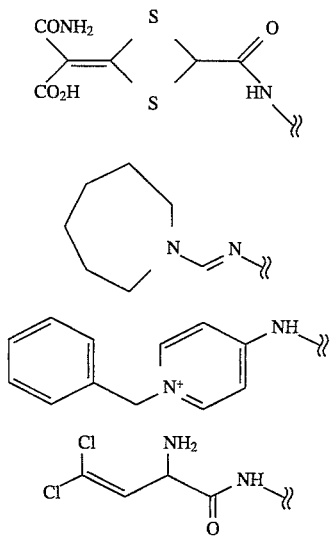

Suitable R² groups are among those well-known in the art, including those defined in the following documents (all incorporated by reference herein). W. Durckheimer et al., "Recent Developments in the Field of Beta-Lactam Antibiotics", 24 Angew. Chem. Int. Ed. Engl. 180 (1985); G. Rolinson, "Beta-Lactam Antibiotics", 17 J. Antimicrobial Chemotherapy 5 (1986); and European Patent Publication 187,456, Jung, published Jul. 16, 1986. Preferred R² groups include hydrogen, methoxy, ethoxy, propoxy, thiomethyl, halogen, cyano, formyl and formylamino. Particularly preferred R² groups include hydrogen, methoxy, halogen, and formylamino.

Quinolone Moieties

Groups $A^1$, $A^2$, $A^3$, $R^8$, $R^7$, and $R^9$ form any of a variety of quinolone, naphthyridine or related heterocyclic moieties known in the art to have antimicrobial activity. Such moieties are well known in the art, as described in the following articles, all incorporated by reference herein: J. Wolfson et al., "The Fluoroquinolones: Structures, Mechanisms of Action and Resistance, and Spectra of Activity In Vitro", 28 Antimicrobial Agents and Chemotherapy 581 (1985); and T. Rosen et al., 31 J. Med Chem. 1586 (1988); T. Rosen et al., 31 J. Med. Chem. 1598 (1988); G. Klopman et al., 31 Antimicrob. Agents Chemother. 1831 (1987); 31:1831–1840; J.P. Sanchez et al., 31 J. Med. Chem. 983 (1988); J. M. Domagala et al., 31 J. Med. Chem. 991 (1988); M. P. Wentland et al., in 20 Ann. Rep. Med. Chem. 145 (D. M. Baily, editor, 1986); J. B. Cornett et al., in 21 Ann. Rep. Med. Chem. 139 (D. M. Bailey, editor, 1986); P. B. Fernandes et al., in 22 Ann. Rep. Med. Chem. 117 (D. M. Bailey, editor, 1987); R. Albrecht, 21 Prog. Drug Research 9 (1977); and P. B. Fernandes et al., in 23 Ann. Rep. Med. Chem. (R. C. Allen, editor, 1987).

Preferred quinolone moieties include those where $A^1$ is $C(R^{40})$, $A^2$ is $C(R^6)$, and $A^3$ is $C(R^{41})$ (i.e., quinolones); $A^1$ is nitrogen, $A^2$ is $C(R^6)$, and $A^3$ is $C(R^{41})$ (i.e., naphthyridines); $A^1$ is $C(R^{40})$, $A^2$ is $C(R^6)$, and $A^3$ is nitrogen (i.e., cinnoline acid derivatives); and where $A^1$ is nitrogen, $A^2$ is nitrogen, and $A^3$ is $C(R^{41})$ (i.e., pyridopyrimidine derivatives). More preferred quinolone moeities are those where $A^1$ is $C(R^{40})$, $A^2$ is $C(R^6)$, and $A^3$ is $C(R^{41})$ (i.e., quinolones); and where $A^1$ is nitrogen, $A^2$ is $C(R^6)$, and $A^3$ is $C(R^{41})$ (i.e., naphthyridines). Particularly preferred quinolone moieties are where $A^1$ is $C(R^{40})$, $A^2$ is $C(R^6)$, and $A^3$ is $C(R^{41})$ (i.e., quinolones).

$R^8$ is preferably alkyl, aryl, cycloalkyl and alkylamino. More preferably, $R^8$ is ethyl, 2-fluoroethyl, 2-hydroxyethyl, t-butyl, 4-fluorophenyl, 2,4-difluorophenyl, methylamino and cyclopropyl. Cyclopropyl is a particularly preferred $R^8$ group. Preferred quinolone moieties also include those where $A^1$ is $C(R^{40})$ and $R^8$ and $R^{40}$ together comprise a 6-membered heterocyclic ring containing an oxygen or sulfur atom.

$R^6$ is preferably hydrogen or halo. More preferably $R^6$ is chlorine or fluorine. Fluorine is a particularly preferred $R^6$ group.

Preferred $R^7$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^7$ groups include unsubstituted or substituted pyridine, piperidine, morpholine, diazabicyclo[3.1.1]heptane, diazabicyclo[2.2.1]heptane, diazabicyclo[3.2.1]octane, diazabicyclo[2.2.2] octane, thiazolidine, imidazolidine, pyrrole and thiamorpholine, as well as the following particularly preferred $R^7$ groups include piperazine, 3-methylpiperazine, 3-aminopyrrolidine, 3-aminomethylpyrrolidine, N,N-dimethyhlaminomethylpyrrolidine, N-methylaminomethylpyrrolidine, N-ethylaminomethylpyrrolidine, pyridine, N-methylpiperazine, and 3,5-dimethylpiperazine.

Preferred quinolonyl lactams include those having a 6-fluoroquinolone moiety or an 8-halo-6-fluoroquinolone moiety, of formula:

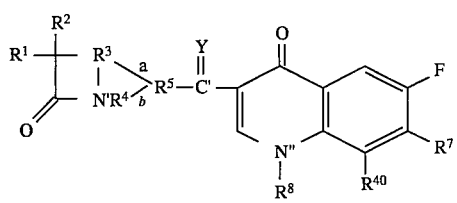

wherein $A^2$ is $C(R^6)$ and $R^6$ is F; $A^3$ is $C(R^{41})$; and $A^1$ is $C(R^{40})$ where $R^{40}$ is hydrogen, fluorine or chlorine. Preferred examples of such quinolone moieties include:

1-cyclopropyl-6-fluoro-1,4-dihydro-4-oxo-7-(1-piperazinyl)-3-quinolinecarboxylic acid;
7-(3-aminopyrrolidinyl)-1-cyclopropyl-6-fluoro-1,4-dihydro-4-oxo-3-quinolinecarboxylic acid;
7-[(3-aminomethyl)pyrrolidinyl]-1-cyclopropyl-6-fluoro-1, 4-dihydro- 4-oxo-3-quinolinecarboxylic acid;
7-(3-aminopyrrolidinyl)-8-chloro-1-cyclopropyl-6-fluoro-1, 4-dihydro- 4-oxo-3-quinolinecarboxylic acid;
7-(3-aminopyrrolidinyl)-1-cyclopropyl-6,8-difluoro-1,4-dihydro-4-oxo-3-quinolinecarboxylic acid;
7-[(3-aminomethyl)pyrrolidinyl]-1-cyclopropyl-6,8-difluoro-1,4 -dihydro-4-oxo-3-quinolinecarboxylic acid;
6,8-difluoro-1-(2-fluoroethyl)-1,4-dihydro-7-(4-methyl-1-piperazinyl)- 4-oxo-3-quinolinecarboxylic acid;
1-ethyl-6-fluoro-1,4-dihydro-4-oxo-1-(1-piperazinyl)-3-quinolinecarboxylic acid;
1-ethyl-6-fluoro-1,4-dihydro-7-(4-methyl-1-piperazinyl)-4 -oxo-3-quinolinecarboxylic acid;
6-fluoro-1,4-dihydro-1-methylamino-7-(4-methyl-1 -piperazinyl)-4-oxo-3-quinolinecarboxylic acid; and
1-cyclopropyl-7-[3-(dimethylaminomethyl)-1-pyrrolidinyl] -6,8 -difluoro-1,4-dihydro-4-oxo-3-quinolinecarboxylic acid.

The following are other examples of such preferred quinolone moieties.

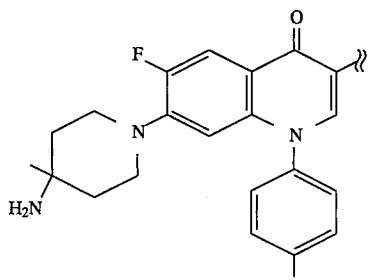

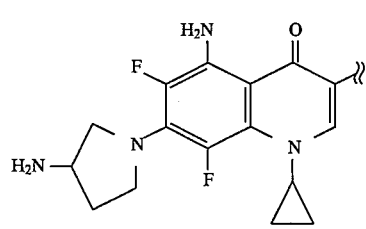

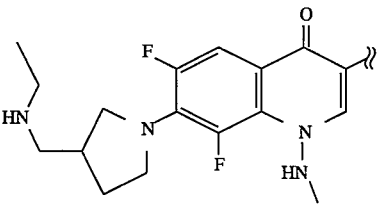

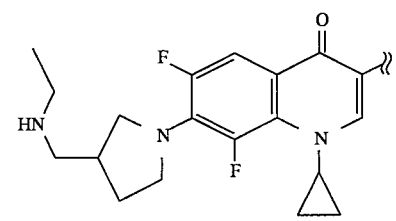

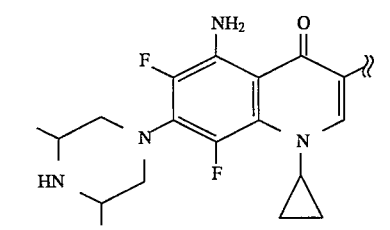

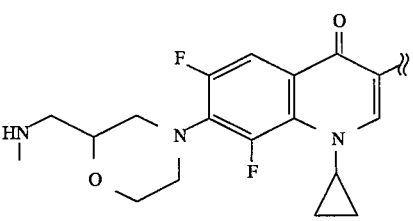

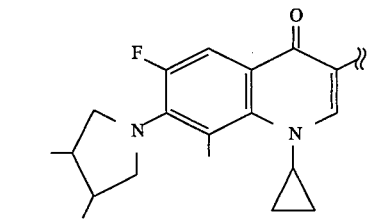

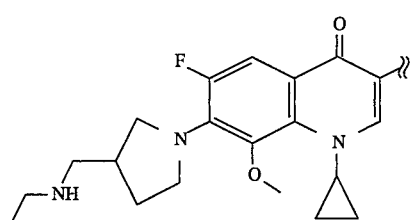

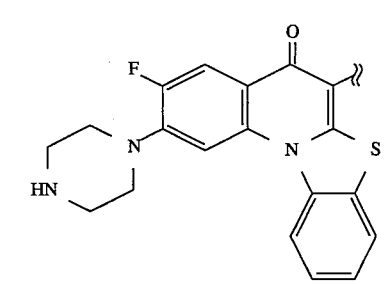

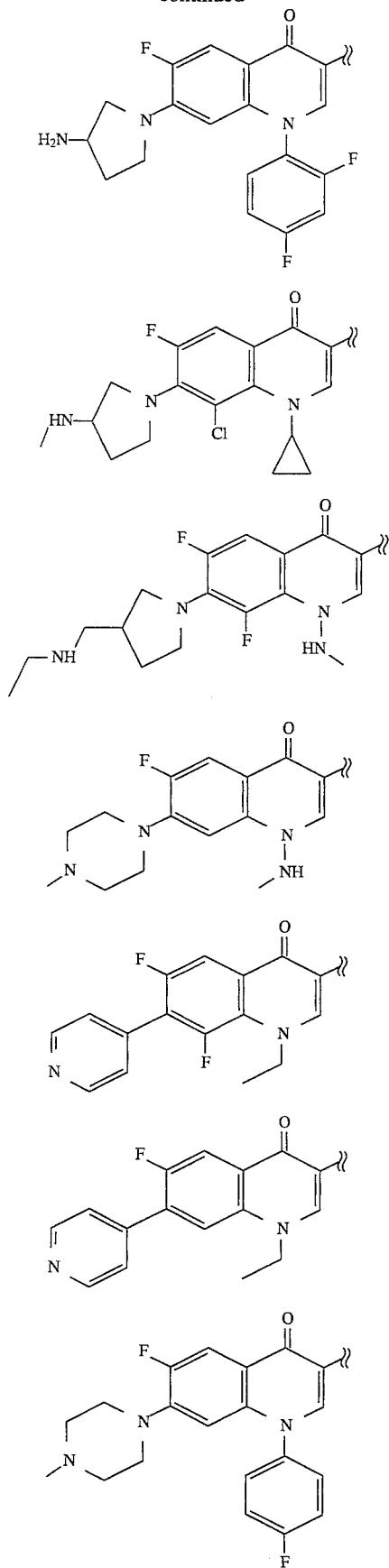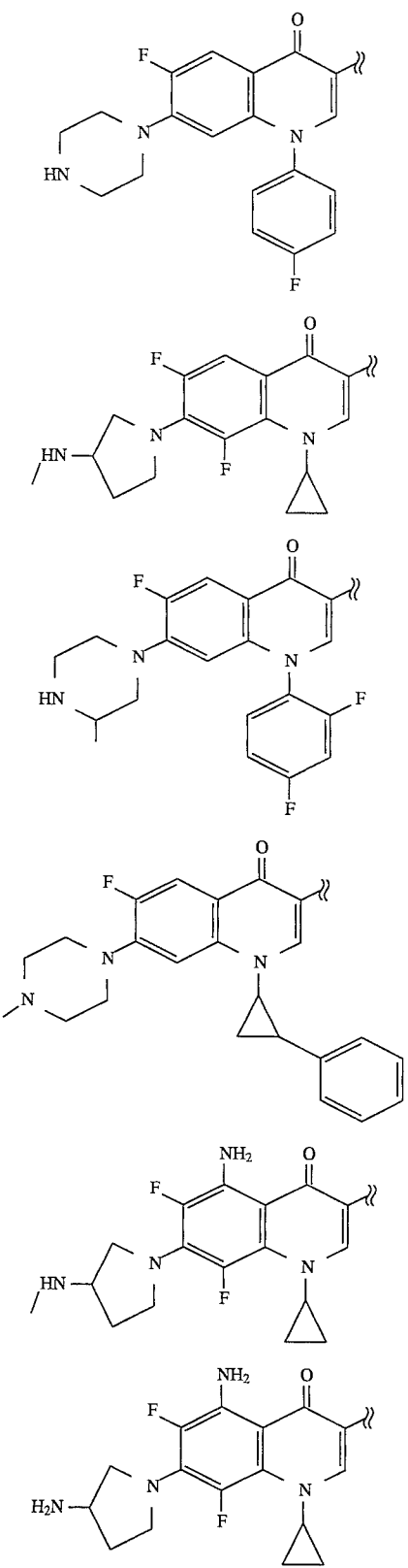

27
-continued
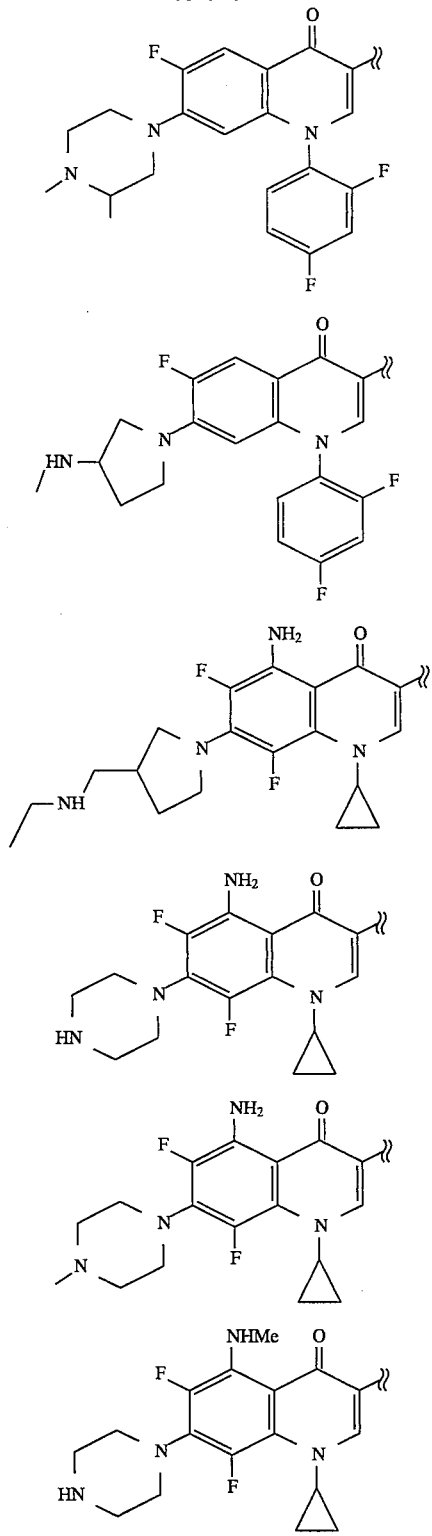
28
-continued
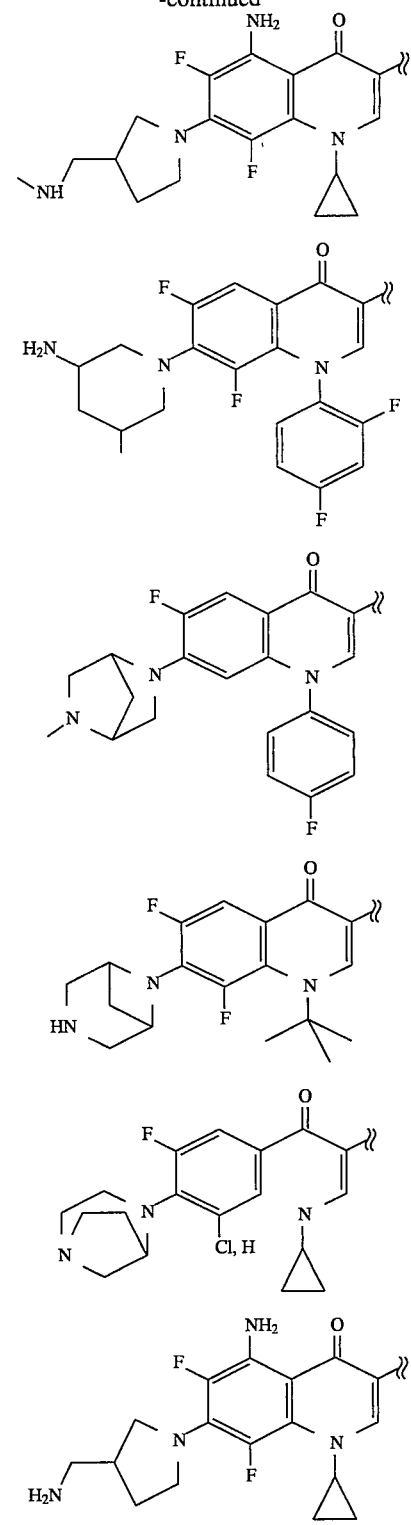
Also preferred are quinolonyl lactams having a 1,8-naphthyridine moiety, of formula:

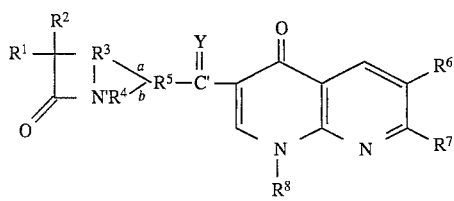
wherein $A^1$ is N; $A^2$ is $C(R^6)$ and $A^3$ is $C(R^{41})$. Preferred examples of such quinolone moieties include:
7-(3-aminopyrrolidinyl)-1-(2,4-difluorophenyl)-6-fluoro-1,4-dihydro-4-oxo-1,8-naphthyridine-3-carboxylic acid; and
1-ethyl-6-fluoro-1,4-dihydro-4-oxo-7-(1-piperazinyl)-1,8-naphthyridine-3-carboxylic acid.
The following are other examples of such preferred quinolone moieties.
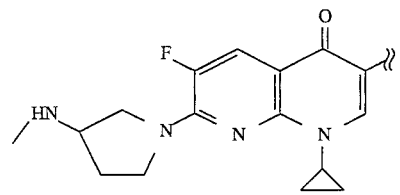
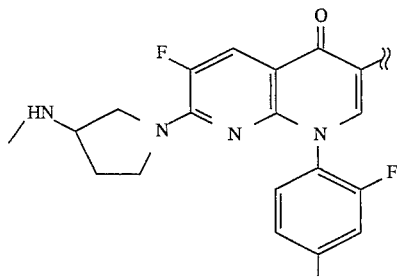
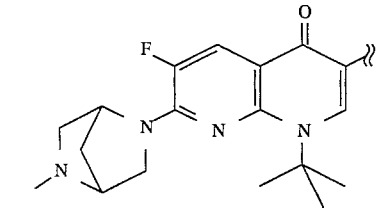
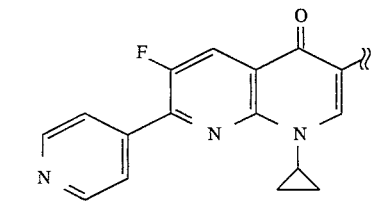
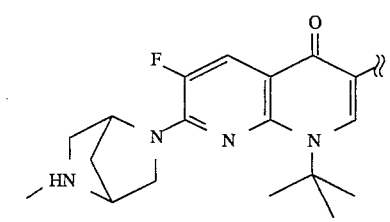
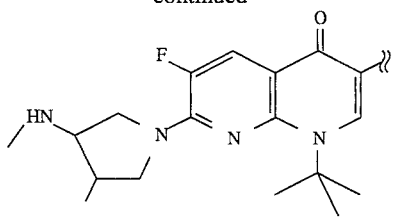
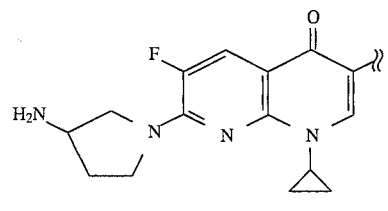
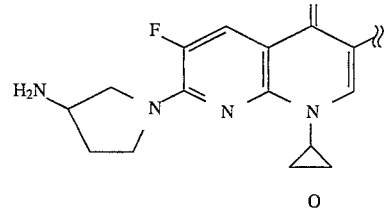
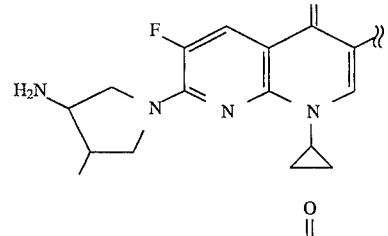
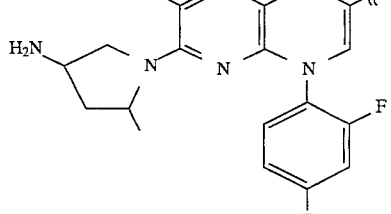
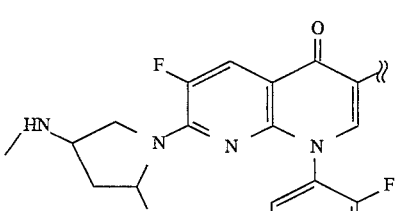

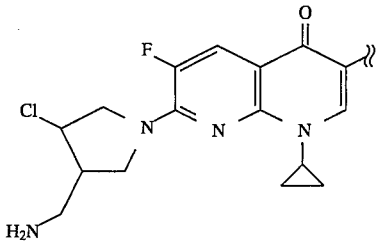

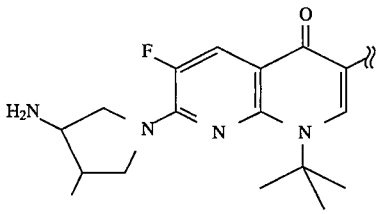

Also preferred are quinolonyl lactams having a pyridobenzoxazine or pyridobenzthiazine moiety, of formula:

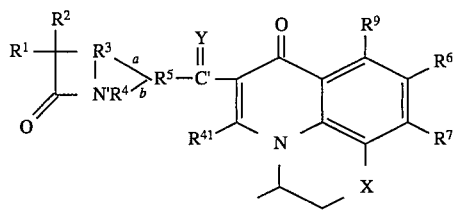

wherein $A^1$ is $C(R^{40})$; $A^2$ is $C(R^6)$; $A^3$ is $C(R^{41})$; and $R^{40}$ and $R^8$ together comprise a linking moiety between N' and A to form a 6-membered, oxygen-containing, heterocyclic ring where X (in this formula) is oxygen or sulfur. Preferred examples of such quinolone moieties include 9-fluoro-4,7-dihydro-3-methyl-10 -(4-methyl-1-piperazinyl)-7-oxo-2H-pyrido[1,2,3-de]-1,4 -benzoxazine-6-carboxylic acid; and the following structures.

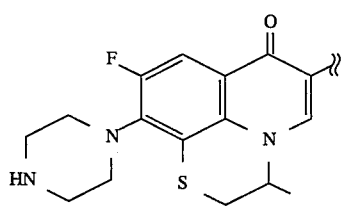

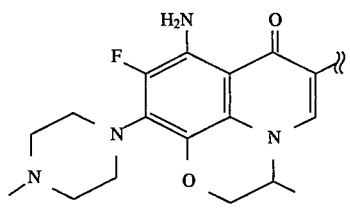

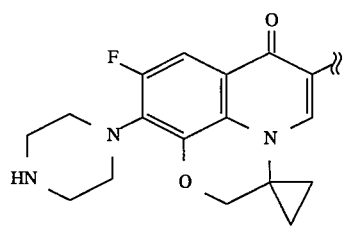

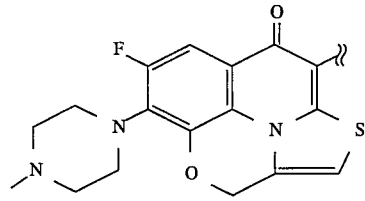

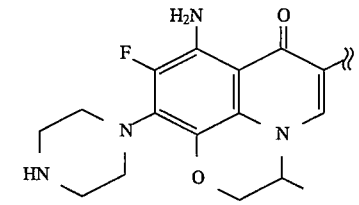

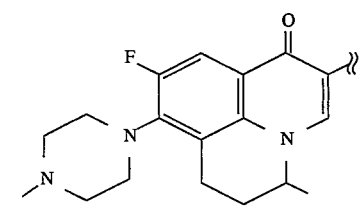

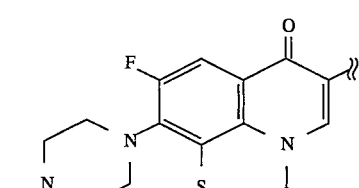

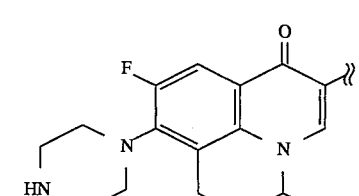

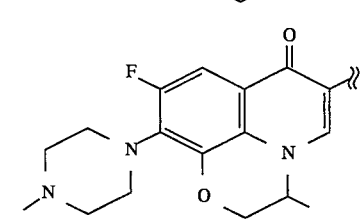

Also preferred are quinolonyl lactams having an isothiazoloquinolinedione or isoxazoloquinolinedione moiety, of formula:

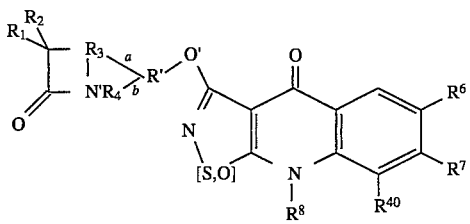

wherein $R^5$ is depicted as $R^1$ and $O^1$ in this formula; $A^1$ is $C(R^{40})$; $A^2$ is $C(R^6)$; $A^3$ is $C(R^{41})$; Y is $NR^{39}$, and $R^{39}$ and $R^{41}$ together comprise a moiety forming a 5-membered, substituted, heterocyclic ring.

Preferred examples of such quinolone moieties include 9-cyclopropyl-6-fluoro-2,3,4,9-tetrahydro-7-(1-piperazinyl)isothiazolo[5,4-b]quinoline-3,4-dione; and:

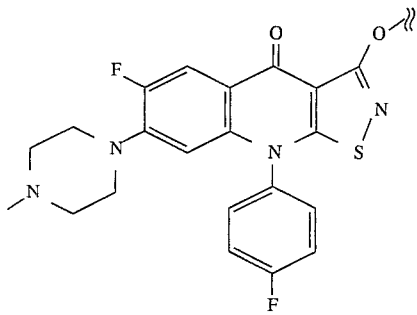

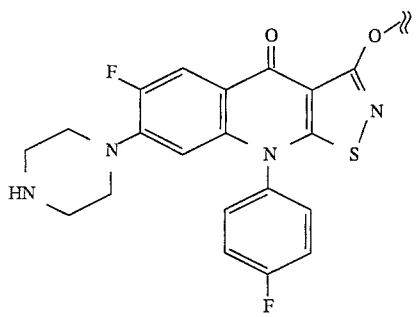

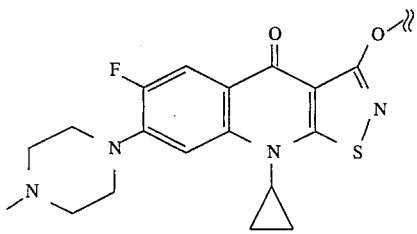

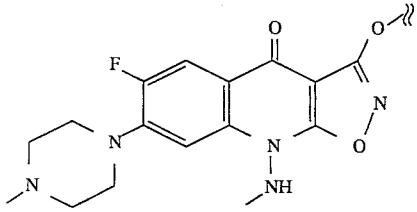

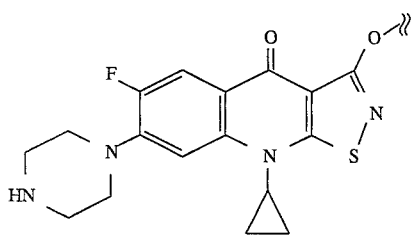

Linking Moieties

Group Y, together with the X substituent of Group $R^5$ and C', form a variety of linking moieties between the lactam-containing structure and the quinolone structure of the quinolonyl lactams. Representative structures for linking groups are set forth below. (In these structures, $R^3$, $R^4$, $R^5$, and bonds "a" and "b" comprise a cephem or penem structure, for purposes of exemplification only. The linking moieties depicted may be used with any of the lactam-containing moieties of this invention.)

Thioester linking moiety:

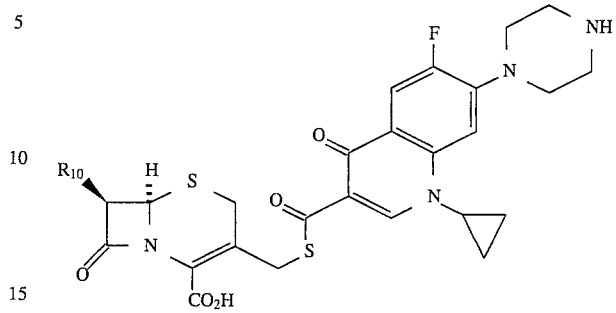

where in X is S, and Y is oxygen.

Another thioester linking moiety is exemplified by the following structure:

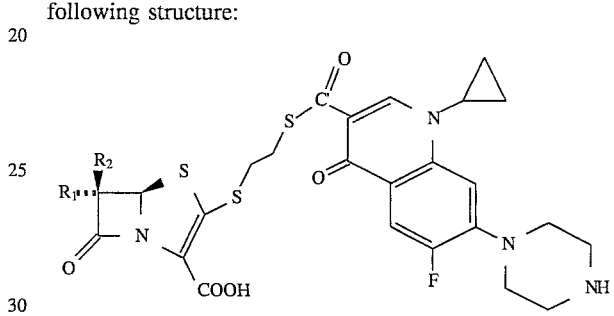

wherein X is $Z^4$—$R^{34}$—$X^1$; $Z^4$ is S, $R^{34}$ is ethyl, $X^1$ is S, and Y is O.

Imidate, linking moiety:

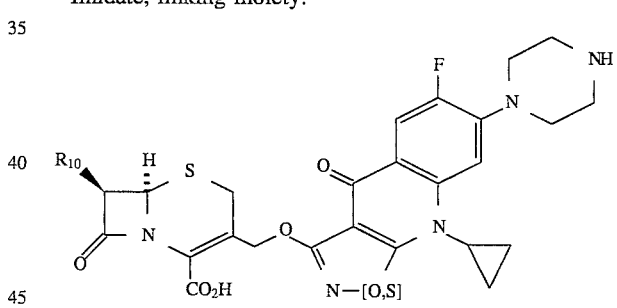

wherein X is O, and Y is $NR^{39}$, $A^3$ is $C(R^{41})$, and $R^{39}$ and $R^{41}$ together comprise a heterocyclic ring.

Amide linking moiety:

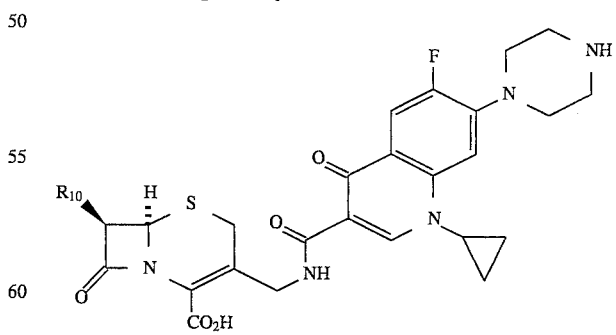

wherein X is $R^{35}$—$N(R^{36})$, $R^{35}$ is nil, and $R^{36}$ is hydrogen; and Y is oxygen.

Hydrazide linking moiety:

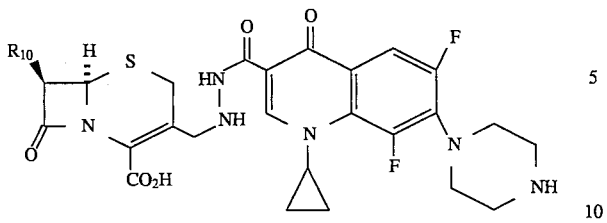

wherein X is $R^{35}$—$N(R^{36})$, $R^{35}$ is $N(R^{36})$, and $R^{36}$ is hydrogen in both occurrences, and Y is oxygen.

Preferred linking moieties include thioester and amide containing moieties.

The specific physical, chemical, and pharmacological properties of the quinolonyl lactams of this invention may depend upon the particular combination of the integral lactam-containing moiety, quinolone moiety and linking moiety comprising the compound. For example, selection of particular integral moieties may affect the relative susceptibility of the quinolonyl lactam to bacterial resistance mechanisms (e.g., beta-lactamase activity).

Preferred quinolonyl lactams include compounds wherein (A) (1) if bond "a" or bond "b" is nil, then $R^5$ is X;

(2) if bond "a" and "b" are single bonds, $R^5$ is —W—C'''=C($R^{10a}$)—$R^{31}$—X—, or —W—C'''($R^{32}$)—$R^{31}$—X—; or (3) if bond "a" is a single bond and bond "b" is a double bond, $R^5$ is —C($R^{10a}$)($R^{33}$)—W—C'''—$R^{31}$—X—; —W—C($R^{10a}$)($R^{33}$)—C'''—$R^{31}$—X''—; —W'—C($R^{10a}$)($R^{33}$)—C'''—$R^{31}$—X—; W'''—C($R^{10a}$)($R^{33}$)—C'''—$R^{31}$—S—; or —W—C'''—$R^{31}$—X—; where W' is O, or C($R^{33}$); W'' is sulfur, and X'' is oxygen or $R^{35}$—$NR^{36}$; and (B) (1) if $R^5$ is —C($R^{10a}$)($R^{33}$)—W—C'''—$R^{31}$—X—; —W—C($R^{10a}$)($R^{33}$)—C'''—$R^{31}$—X''—;; or —W—C'''—$R^{31}$—X—, Y is oxygen or N—$R^{39}$; or (2) if $R^5$ is —W''—C($R^{10a}$)($R^{33}$)—C'''—$R^{31}$—S—, Y is N—$R^{39}$.

Other preferred quinolonyl lactams include compounds having the following specific combinations of lactam-containing moieties, quinolone moieties and linking moieties.

1) Amide-linked cephem quinolones, such as compounds of the following classes.

a) where
the lactam-containing moiety is a cephem, wherein bond "a" is a single bond; bond "b" is a double bond; $R^3$ is —CH—; $R^4$ is —C($CO_2H$)—; $R^5$ is —S—$CH_2$—C'''—$CH_2$—NH—;
the quinolone moiety is a structure, wherein $A^2$ is —CF—; $A^3$ is —CH—; and $R^7$ is a heterocyclic ring; and
Y is oxygen b) where
the lactam-containing moiety is a cephem, wherein bond "a" is a single bond; bond "b" is a double bond; $R^3$ is —CH—; $R^4$ is —C($CO_2H$)—; $R^5$ is —S—$CH_2$—C'''—$CH_2$—NH—;
the quinolone moiety is a 6-fluoroquinolone, wherein $A^1$ is —C($R^{40}$)—; $A^2$ is —CF—; $A^3$ is —CH—; and $R^7$ is a heterocyclic ring; and
Y is oxygen c) where
the lactam-containing moiety is a cephem, wherein bond "a" is a single bond; bond "b" is a double bond; $R^3$ is —CH—; $R^4$ is —C($CO_2H$)—; $R^5$ is —S—$CH_2$—C'''—$CH_2$—NH—;
the quinolone moiety is a naphthyridinone, wherein $A^1$ is —N—; $A^2$ is —CF—; $A^3$ is —CH—; and $R^7$ is a heterocyclic ring; and
Y is oxygen d) where
the lactam-containing moiety is a cephem, wherein bond "a" is a single bond; bond "b" is a double bond; $R^2$ is —H or —OMe; $R^3$ is —CH—; $R^4$ is —C($CO_2H$)—; $R^5$ is —S—$CH_2$—C'''—$CH_2$—NH—; and $R^1$ is [[(2-thienyl)acetyl]amino], [[(2-amino-4-thiazolyl)(methoxyimino)acetyl]amino], [[(4-pyridylthio)acetyl]amino], [(phenoxy)acetyl]amino], [[(2-amino-4-thiazolyl)acetyl]amino], [[(2-amino-4-thiazolyl)[[(3,4-dihydroxyphenyl)carbonyl]amino]acetyl]amino];
the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and
Y is oxygen Amide-linked cephera quinolones of the classes (b), (c) and (d) are preferred; compounds of class (d) are particularly preferred.

(2) Amide-linked penem quinolones, such as compounds of the following classes.

a) where
the lactam-containing moiety is a penem, wherein bond "a" is a single bond; bond "b" is a double bond; $R^3$ is —CH—; $R^4$ is —C($CO_2H$)—; $R^5$ is —S—C'''—$CH_2$—NH—;
the quinolone moiety is a structure, wherein $A^2$ is —CF—; $A^3$ is —CH—; and $R^7$ is a heterocyclic ring; and
Y is oxygen b) where
the lactam-containing moiety is a penem, wherein bond "a" is a single bond; bond "b" is a double bond; $R^1$ is (1-hydroxyethyl); $R^2$ is —H; $R^3$ is —CH—; $R^4$ is —C($CO_2H$)—; $R^5$ is —S—C'''—$CH_2$—NH—;
the quinolone moiety is a 6-fluoroquinolone, wherein $A^1$ is —C($R^{40}$)—; $A^2$ is —CF—; $A^3$ is —CH—; and $R^7$ is a heterocyclic ring; and
Y is oxygen c) where
the lactam-containing moiety is a penem, wherein bond "a" is a single bond; bond "b" is a double bond; $R^3$ is —CH—; $R^4$ is —C($CO_2H$)—; $R^5$ is —S—C'''—$CH_2$—NH—;
quinolone moiety is a naphthyridinone, wherein $A^1$ is —N—; $A^2$ is —CF—; $A^3$ is —CH—; and $R^7$ is a heterocyclic ring; and
Y is oxygen d) where
the lactam-containing moiety is a penem, wherein bond "a" is a single bond; bond "b" is a double bond; $R^3$ is —CH—; $R^4$ is —C($CO_2H$)—; $R^5$ is —S—C'''—$CH_2$—NH—;
the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Amide-linked penem quinolones of the classes (b), (c) and (d) are preferred; compounds of class (d) are particularly preferred.

3) Amide-linked penem quinolones, such as compounds of the following classes.

a) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—NH—;

the quinolone moiety is a structure, wherein $A^2$ is —CF—; $A^3$ is —CH—; and $R^7$ is a heterocyclic ring; and Y is oxygen b) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—NH—;

the quinolone moiety is a 6-fluoroquinolone, wherein $A^1$ is —C($R^{40}$)—; $A^2$ is —CF—; $A^3$ is —CH—; and $R^7$ is a heterocyclic ring; and Y is oxygen c) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—NH—;

the quinolone moiety is a naphthyridinone, wherein $A^1$ is —N—; $A^2$ is —CF—; $A^3$ is —CH—; and $R^7$ is a heterocyclic ring; and Y is oxygen d) where the lactam-containing moiety is a penem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —S—C'''—S—CH$_2$CH$_2$—NH—;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Amide-linked penem quinolones of the classes (b), (c) and (d) are preferred; compounds of class (d) are particularly preferred.

4) Amide-linked carbapenem quinolones, such as compounds of the following classes.

a) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—NH—;

the quinolone moiety is a structure, wherein $A^2$ is —CF—; $A^3$ is —CH—; and $R^7$ is a heterocyclic ring; and Y is oxygen b) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—NH—;

the quinolone moiety is a 6-fluoroquinolone, wherein $A^1$ is —C($R^{40}$)—; $A^2$ is —CF—; $A^3$ is —CH—; and $R^7$ is a heterocyclic ring; and Y is oxygen c) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—CH$_2$—NH—;

the quinolone moiety is a naphthyridinone, wherein $A^1$ is —N—; $A^2$ is —CF—; $A^3$ is —CH—; and $R^7$ is a heterocyclic ring; and Y is oxygen d) where the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —CH($R^{33}$)—C'''—CH$_2$—NH—; $R^{33}$ is —H or —Me;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Amide-linked carbapenem quinolones of the classes (b), (c) and (d) are preferred; compounds of class (d) are particularly preferred.

5) Amide-linked carbapenem quinolones, such as compounds of the following classes.

a) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—S—CH$_2$CH$_2$—NH—;

the quinolone moiety is a structure, wherein $A^2$ is —CF—; $A^3$ is —CH—; and $R^7$ is a heterocyclic ring; and Y is oxygen b) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—S—CH$_2$CH$_2$—NH—;

the quinolone moiety is a 6-fluoroquinolone, wherein $A^1$ is —C($R^{40}$)—; $A^2$ is —CF—; $A^3$ is —CH—; and $R^7$ is a heterocyclic ring; and Y is oxygen c) where the lactam-containing moiety is a carbapenem, wherein bond "a" is a single bond; bond "b" is a double bond; $R^3$ is —CH—; $R^4$ is —C(CO$_2$H)—; $R^5$ is —CH($R^{33}$)—C'''—S—CH$_2$CH$_2$—NH—;

the quinolone moiety is a naphthyridinone, wherein $A^1$ is —N—; $A^2$ is —CF—; $A^3$ is —CH—; and $R^7$ is a heterocyclic ring; and Y is oxygen d) where
the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —CH($R^{33}$)—C'''—S—CH$_2$CH$_2$—NH—; $R^{33}$ is —H or —Me;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Amide-linked penem quinolones of the classes (b), (c) and (d) are preferred; compounds of class (d) are particularly preferred.

6) Amide-linked oxacephem quinolones, such as compounds of the class where the lactam-containing moiety is a oxacephem, wherein bond "a" is a single bond; bond "b" is a double bond; $R^3$ is —CH—; $R^4$ is —C(CO$_2$H)—; $R^5$ is —O—CH$_2$—C'''—CH$_2$—NH—;

the quinolone moiety is a structure, wherein $A^2$ is —CF—; $A^3$ is —CH—; and $R^7$ is a heterocyclic ring; and Y is oxygen 7) Amide-linked isocephem quinolones, such as compounds of the class where the lactam-containing moiety is a isocephem, wherein bond "a" is a single bond; bond "b" is a double bond; $R^3$ is —CH—; $R^4$ is —C(CO$_2$H)—; $R^5$ is —CH$_2$—S—C''' —CH$_2$—NH—;

the quinolone moiety is a structure, wherein $A^2$ is —CF—; $A^3$ is —CH—; and $R^7$ is a heterocyclic ring; and Y is oxygen 8) Amide-linked iso-oxacephem quinolones, such as compounds of the class where the lactam-containing moiety is a iso-oxacephem, wherein bond "a" is a single bond; bond "b" is a double bond; $R^3$ is —CH—; $R^4$ is —C(CO$_2$H)—; $R^5$ is —CH$_2$—O—C'''—CH$_2$—NH—;

the quinolone moiety is a structure, wherein $A^2$ is —CF—; $A^3$ is —CH—; and $R^7$ is a heterocyclic ring; and Y is oxygen 9) Amide-linked carbacephem quinolones, such as compounds of the class where the lactam-containing moiety is a carbacephem, wherein bond "a" is a single bond; bond "b" is a double bond; $R^3$ is —CH—; $R^4$ is —C(CO$_2$H)—; $R^5$ is —CH$_2$—CH$_2$—C'''—CH$_2$—NH—;

the quinolone moiety is a structure, wherein $A^2$ is —CF—; $A^3$ is —CH—; and $R^7$ is a heterocyclic ring; and Y is oxygen 10) Amide-linked monobactam quinolones, such as compounds of the class where the lactam-containing moiety is a monobactam, wherein bond "a" is a single bond; bond "b" is nil; $R^3$ is —CH— and is bonded directly to X; $R^5$ is nil; X is —CH$_2$NH—;

the quinolone moiety is a structure, wherein $A^2$ is —CF—; $A^3$ is —CH—; and $R^7$ is a heterocyclic ring; and Y is oxygen 11) Thioester-linked cephem quinolones, such as compounds of the following classes.

a) where
the lactam-containing moiety is a cephem, wherein bond "a" is a single bond; bond "b" is a double bond; $R^3$ is —CH—; $R^4$ is —C(CO$_2$H)—; $R^5$ is —S—CH$_2$—C'''—CH$_2$—S—;

the quinolone moiety is a structure, wherein $A^2$ is —CF—; $A^3$ is —CH—; and $R^7$ is a heterocyclic ring; and Y is oxygen b) where
the lactam-containing moiety is a cephem, wherein bond "a" is a single bond; bond "b" is a double bond; $R^3$ is —CH—; $R^4$ is —C(CO$_2$H)—; $R^5$ is —S—CH$_2$—C''' —CH$_2$—S—;

the quinolone moiety is a 6-fluoroquinolone, wherein $A^1$ is —C($R^{40}$)—; $A^2$ is —CF—; $A^3$ is —CH—; and $R^7$ is a heterocyclic ring; and Y is oxygen c) where
the lactam-containing moiety is a cephem, wherein bond "a" is a single bond; bond "b" is a double bond; $R^3$ is —CH—; $R^4$ is —C(CO$_2$H)—; $R^5$ is —S—CH$_2$—C'''—CH$_2$—S—;

the quinolone moiety is a naphthyridinone, wherein $A^1$ is —N—; $A^2$ is —CF—; $A^3$ is —CH—; and $R^7$ is a heterocyclic ring; and Y is oxygen d) where
the lactam-containing moiety is a cephem, wherein bond "a" is a single bond; bond "b" is a double bond; $R^2$ is —H or —OMe; $R^3$ is —CH—; $R^4$ is —C(CO$_2$H)—; $R^5$ is —S—CH$_2$—C'''—CH$_2$—S—; and, $R^1$ is [[(2-thienyl)acetyl]amino], [[(2-amino-4-thiazolyl)(methoxyimino)acetyl]amino], [[(4-pyridylthio)acetyl]amino], [(phenoxy)acetyl]amino], [[(2-amino-4-thiazolyl)acetyl]amino], [[(2-amino-4-thiazolyl)[[(3,4-dihydroxyphenyl)carbonyl]amino]acetyl]amino];

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Thioester-linked cephem quinolones of the classes (b), (c) and (d) are preferred; compounds of class (d) are particularly preferred.

12) Thioester-linked penem quinolones, such as compounds of the following classes.

a) where
the lactam-containing moiety is a penem, wherein bond "a" is a single bond; bond "b" is a double bond; $R^3$ is —CH—; $R^4$ is —C(CO$_2$H)—; $R^5$ is —S—C'''—CH$_2$—S—;

the quinolone moiety is a structure, wherein $A^2$ is —CF—; $A^3$ is —CH—; and $R^7$ is a heterocyclic ring; and Y is oxygen b) where
the lactam-containing moiety is a penem, wherein bond "a" is a single bond; bond "b" is a double bond; $R^3$ is —CH—; $R^4$ is —C(CO$_2$H)—; $R^5$ is —S—C'''—CH$_2$—S—;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Thioester-linked penem quinolones of the class (b) are preferred.

13) Thioester-linked penem quinolones, such as compounds of the following classes.

a) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—S—;

the quinolone moiety is a structure, wherein $A^2$ is —CF—; $A^3$ is —CH—; and $R^7$ is a heterocyclic ring; and Y is oxygen b) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—S—;

the quinolone moiety is a 6-fluoroquinolone, wherein $A^1$ is —C(R$^{40}$)—; $A^2$ is —CF—; $A^3$ is —CH—; and $R^7$ is a heterocyclic ring; and Y is oxygen c) where the lactam-containing moiety is a penem, wherein bond "a" is a single bond; bond "b" is a double bond; $R^3$ is —CH—; $R^4$ is —C(CO$_2$H)—; $R^5$ is —S—C'''—S—CH$_2$CH$_2$—S—;

the quinolone moiety is a naphthyridinone, wherein $A^1$ is —N—; $A^2$ is —CF—; $A^3$ is —CH—; and $R^7$ is a heterocyclic ring; and Y is oxygen d) where the lactam-containing moiety is a penem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —S—C'''—S—CH$_2$CH$_2$—S—;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Thioester-linked penem quinolones of the classes (b), (c) and (d) are preferred; compounds of class (d) are particularly preferred.

14) Thioester-linked carbapenem quinolones, such as compounds of the following classes.

a) where the lactam-containing moiety is a carbapenem, wherein bond "a" is a single bond; bond "b" is a double bond; $R^3$ is —CH—; $R^4$ is —C(CO$_2$H)—; $R^5$ is —CH(R$^{33}$)—C'''—CH$_2$—S—;

the quinolone moiety is a structure, wherein $A^2$ is —CF—; $A^3$ is —CH—; and $R^7$ is a heterocyclic ring; and Y is oxygen b) where the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —CH(R$^{33}$)—C'''—CH$_2$—S—; $R^{33}$ is —H or —Me; and, the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Thioester-linked carbapenem quinolones of the class (b) are preferred.

15) Thioester-linked carbapenem quinolones, such as compounds of the following classes.

a) where the lactam-containing moiety is a carbapenem, wherein bond "a" is a single bond; bond "b" is a double bond; $R^3$ is —CH—; $R^4$ is —C(CO$_2$H)—; $R^5$ is —CH(R$^{33}$)—C'''—S—CH$_2$CH$_2$—S—;

the quinolone moiety is a structure, wherein $A^2$ is —CF—; $A^3$ is —CH—; and $R^7$ is a heterocyclic ring; and Y is oxygen b) where the lactam-containing moiety is a carbapenem, wherein bond "a" is a single bond; bond "b" is a double bond; $R^3$ is —CH—; $R^4$ is —C(CO$_2$H)—; $R^5$ is —CH(R$^{33}$)—C'''—S—CH$_2$CH$_2$—S—;

the quinolone moiety is a 6-fluoroquinolone, wherein $A^1$ is —C(R$^{40}$)—; $A^2$ is —CF—; $A^3$ is —CH—; and $R^7$ is a heterocyclic ring; and Y is oxygen c) where the lactam-containing moiety is a carbapenem, wherein bond "a" is a single bond; bond "b" is a double bond; $R^3$ is —CH—; $R^4$ is —C(CO$_2$H)—; $R^5$ is —CH(R$^{33}$)—C'''—S—CH$_2$CH$_2$—S—;

the quinolone moiety is a naphthyridinone, wherein $A^1$ is —N—; $A^2$ is —CF—; $A^3$ is —CH—; and $R^7$ is a heterocyclic ring; and Y is oxygen d) where the lactam-containing moiety is a carbapenem, wherein bond "a" is a single bond; bond "b" is a double bond; $R^1$ is (1-hydroxyethyl); $R^2$ is —H; $R^3$ is —CH—; $R^4$ is —C(CO$_2$H)—; $R^5$ is —CH(R$^{33}$)—C'''—CH$_2$CH$_2$—S—; $R^{33}$ is —H or —Me;

the quinolone moiety is a structure, wherein $A^2$ is —CF—; $A^3$ is —CH—; $R^9$ is —H; $A^1$ is —CH—, —CF—, —CCl—, or —N—; $R^8$ is cyclopropyl, ethyl, 2,4-difluorophenyl, 4-fluorophenyl, or t-butyl; and $R^7$ is a 3-amino-1-pyrrolidinyl group, a 4-methyl-1-piperazinyl group, a 3-aminomethyl-1-pyrrolidinyl group, a 3-ethylaminomethyl-1-pyrrolidinyl group or a 1-piperazinyl group; and Y is oxygen Thioester-linked penem quinolones of the classes (b), (c) and (d) are preferred; compounds of class (d) are particularly preferred.

16) Thioester-linked oxacephem quinolones, such as compounds of the class where the lactam-containing moiety is a oxacephem, wherein bond "a" is a single bond; bond "b" is a double bond; $R^3$ is —CH—; $R^4$ is —C(CO$_2$H)—; $R^5$ is —O—CH$_2$—C'''—CH$_2$—S—;

the quinolone moiety is a structure, wherein $A^2$ is —CF—; $A^3$ is —CH—; and $R^7$ is a heterocyclic ring; and Y is oxygen 17) Thioester-linked isocephem quinolones, such as compounds of the class where the lactam-containing moiety is a isocephem, wherein bond "a" is a single bond; bond "b" is a double bond; $R^3$ is —CH—; $R^4$ is —C(CO$_2$H)—; $R^5$ is —CH$_2$—S—C'''—CH$_2$—S—;

the quinolone moiety is a structure, wherein $A^2$ is —CF—; $A^3$ is —CH—; and $R^7$ is a heterocyclic ring; and Y is oxygen 18) Thioester-linked iso-oxacephem quinolones, such as compounds of the class where the lactam-containing moiety is a iso-oxacephem, wherein bond "a" is a single bond; bond "b" is a double bond; $R^3$ is —CH—; $R^4$ is —C(CO$_2$H)—; $R^5$ is —CH$_2$—O—C'''—CH$_2$—S—;

the quinolone moiety is a structure, wherein $A^2$ is —CF—; $A^3$ is —CH—; and $R^7$ is a heterocyclic ring; and Y is oxygen 19) Thioester-linked carbacephem quinolones, such as compounds of the class where the lactam-containing moiety is a carbacephem, wherein bond "a" is a single bond; bond "b" is a double bond; $R^3$ is —CH—; $R^4$ is —C(CO$_2$H)—; $R^5$ is —CH$_2$—CH$_2$—C'''—CH$_2$—S—;

the quinolone moiety is a structure, wherein $A^2$ is —CF—; $A^3$ is —CH—; and $R^7$ is a heterocyclic ring; and Y is oxygen 20) Thioester-linked monobactam quinolones, such as compounds of the class where the lactam-containing moiety is a monobactam, wherein bond "a" is a single bond; bond "b" is nil; $R^3$ is —CH— and is bonded directly to X; $R^5$ is nil; X is —S—;

the quinolone moiety is a structure, wherein $A^2$ is —CF—; $A^3$ is —CH—; and $R^7$ is a heterocyclic ring; and Y is oxygen Quinolonyl lactams of this invention include (for example) the following compounds.

[6R-(6α,7β)]-7-[[Carboxy(4-hydroxyphenyl)acetyl]amino]- 3-[[1-ethyl-6-fluoro-1,4-dihydro-4-oxo-7-(1-piperazinyl)-3 -quinolinyl]carbonylamino]-7-methoxy-8-oxo-5-oxa-1- azabicyclo[4.2.0]oct-2-ene-carboxylic acid disodium salt

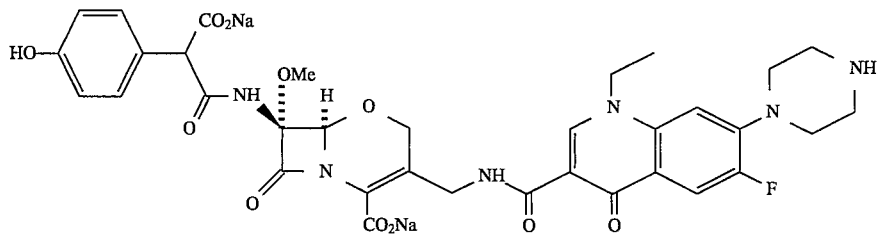

[6R-(6a,7b)]-3-[[[7-(3-Amino-1-pyrrolidinyl)-8-chloro-1 -cyclopropyl-6-fluoro-1,4-dihydro-4-oxo-3-quinolinyl]carbonylthio] methyl]-7-[[(difluoromethylthio)acetyl]amino]-7-methoxy-8 -oxo-5-oxa-1-azabicyclo[4.2.0]oct-2-ene-2-carboxylic acid sodium salt

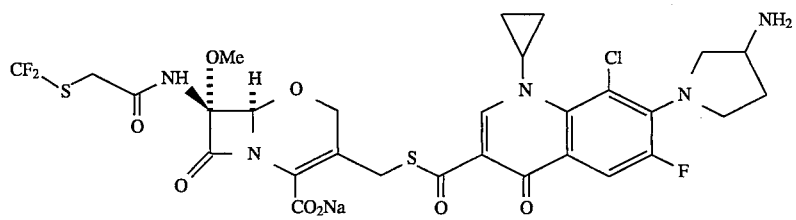

[5R-[5a,6a]]-3-[[[7-(3-amino-1-pyrrolidinyl)-1-(2,4 -difluorophenyl)-6-fluoro-1,4-dihydro-4-oxo-1,8-napthyridin-3-yl] -carbonylthio]methyl]-6-[(R)-1-hydroxyethyl]-7-oxo-4-thia-1-azabicyclo[ 3.2.0]hept-2-ene-2-carboxylic acid sodium salt

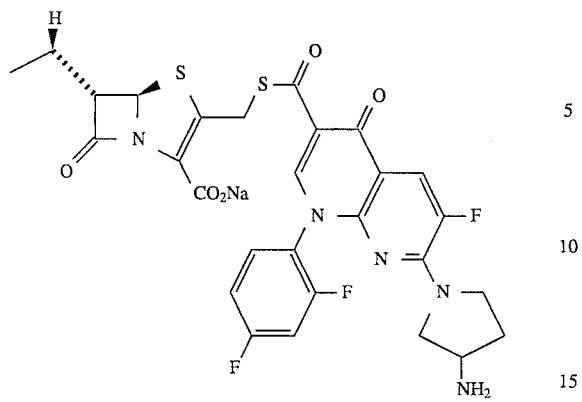

[6R-(6a,7b)]-7-[(R)-[[[(5-carboxy-1H-imidazol-4 -yl-)carbonyl]amino]hydroxyphenyl)acetyl]amino]-3-[[[5-ethyl- 5,8-dihydro-8-oxo-1,3-dioxolo[4,5-g]quinol in-7 -yl-carboxyl]amino]methyl]-8-oxo-5-thia-1-azabicyclo[4.2.0] oct-2 -ene-2-carboxylic acid disodium salt

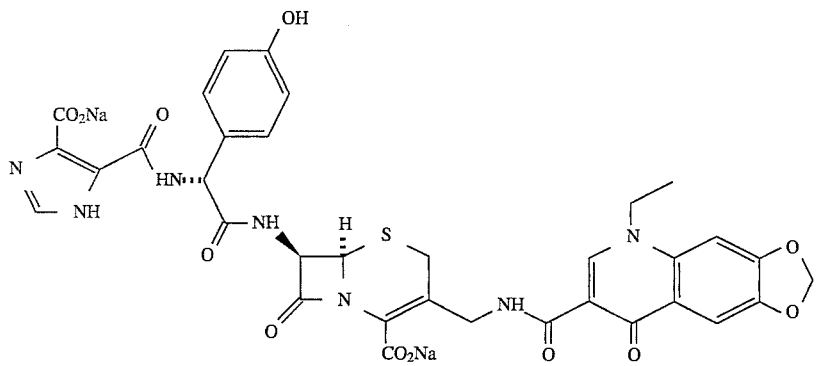

[6R-(6a,7b)]-3-[[[[1-ethyl-6-fluoro-1,4-dihydro-4-oxo-7-(1 -piperazinyl)-1,8-naphthyridin-3-yl]carbonyl]thio]methyl]-7 -[[[[(R)-(4-ethyl-2,3-dioxo-1-piperazinyl)carbonyl] amino](4 -hydroxyphenyl)acetyl]amino]-8-oxo-5-thia-1-azabicyclo[4.2.0] -oct-2-ene-2-carboxylic acid sodium salt

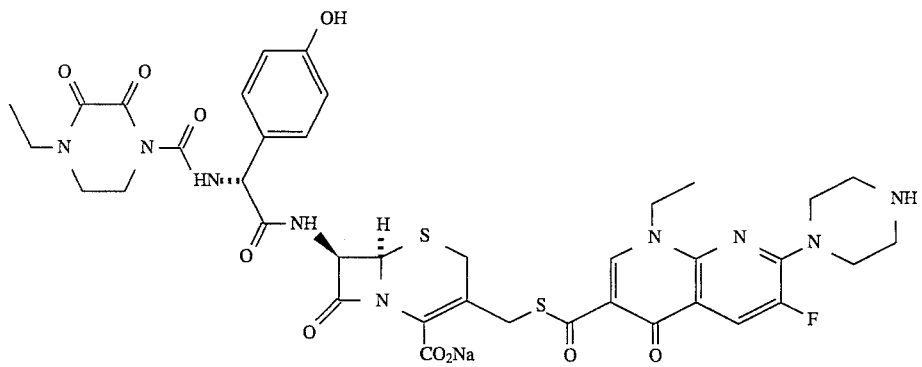

[6R-(6a,7b)]-7-[[(2-amino-4-thiazolyl)[(]-carboxy-1 -methyl)-thoxyimino]acetyl]amino]-3-[[[[]-cyclopropyl-6-fluoro-1,4 -dihydro-4-oxo-7-(]-piperazinyl)-3-quinolinyl] carbonyl]thio]methyl]- 5-thia-1-azabicyclo[4.2.0]oct-2-ene-2-carboxylic acid disodium salt

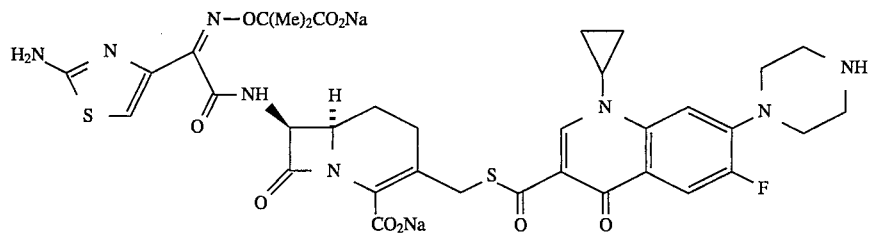

[6R-[6a,7b]]-3-[[[7-(3-amino-1-pyrrolidinyl)-8-chloro-1-cyclopropyl-6-fluoro-1,4-dihydro-4-oxo-3-quinolinyl]carbonylamino]methyl]-7-[[[[(R)-6,7-dihydroxy-4-oxo-(4H)-1-benzopyran-3-yl]carbonylamino]-4-hydroxyphenylacetyl]amino]-8-oxo-5-thia-1-azabicyclo[4.2.0]oct-2-ene-2-carboxylic acid sodium salt

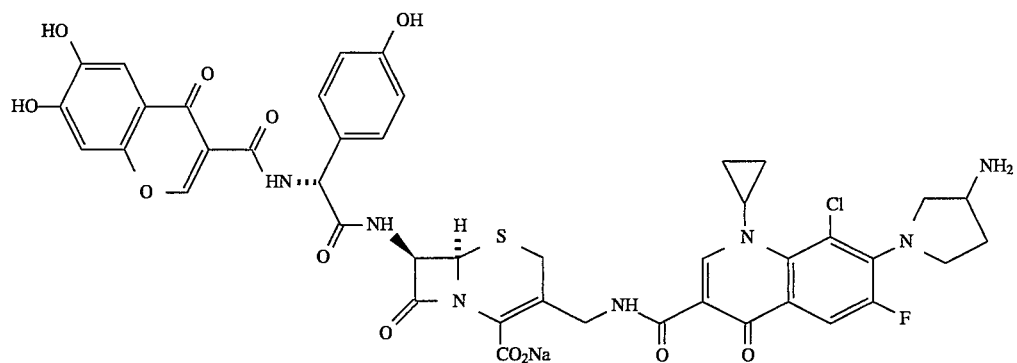

[6R-[6a,7b]]-7-[[(R)-amino(hydroxyphenyl)acetyl]amino]-3-[[[7-(3-amino-1-pyrrolidinyl)-1-difluorophenyl-6-fluoro-1,4-dihydro-4-oxo-1-8-naphthyridin-3-yl]carbonylthio]methyl)-8-oxo-5-thia-1-azabicyclo[4.2.0]oct-2-ene-2-carboxylic acid sodium salt

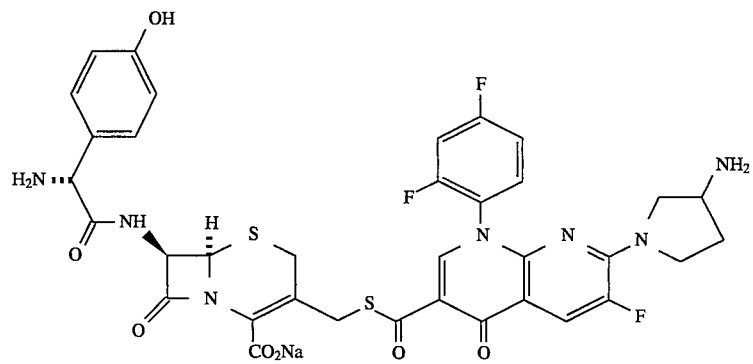

[6R-[6a,7b]]-7-[[(R)-amino(2-naphthalenyl)acetyl]amino]-3-[[[(1-ethyl-1,4-dihydro-7-methyl-4-oxo-3-quinolinyl)carbonylamino] methyl]-8-oxo-5-thia-1-azabicyclo[4.2.0]oct-2-ene-2-carboxylic acid sodium salt

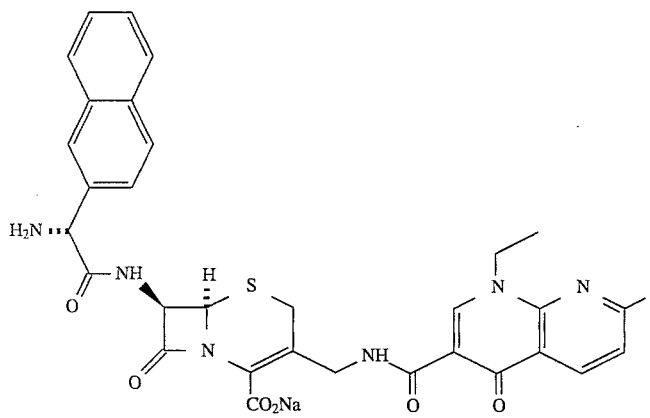

(3S)-2-[[[1-ethyl-6-fluoro-1,4-dihydro-4-oxo-7-(1-piperazinyl)- 3-quinolinyl]carbonyl]thio]-3-[[[[(R)-4-ethyl-2,3-dioxo- 1-piperazinyl]carbonyl]amino](4-hydroxyphenyl)acetyl]amino]-4-oxo-1-azetinesulfonic acid sodium salt

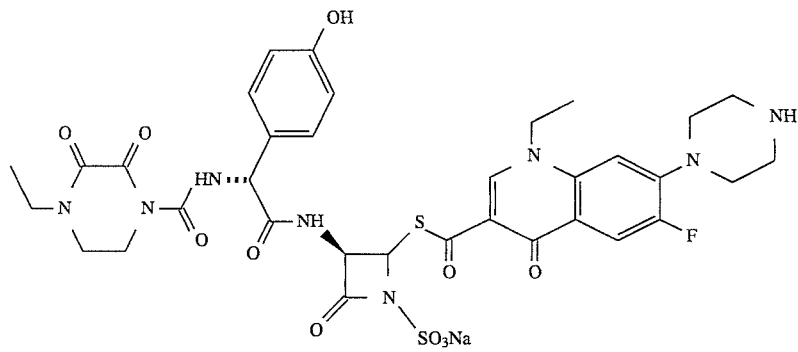

(3S)-3-[[[(2-amino-4-thiazolyl)(methoxyimino)]acetyl] amino]- 2-[[[9-fluoro-4,7-dihydro-3-methyl-10-(4-methyl- 1-piperazinyl)- 7-oxo-2H-pyrido[1,2,3-de]-1,4-benzoxazin-6-yl]carbonyl]thio]-4 -oxo-1-azetidinesulfonic acid sodium salt

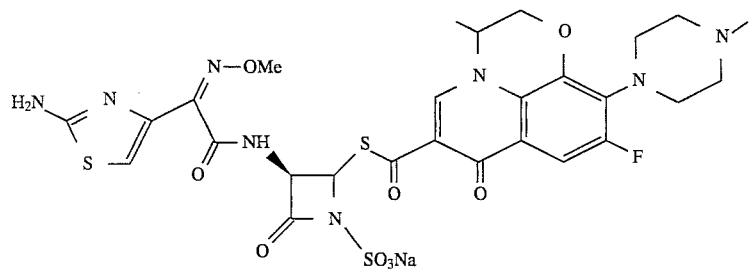

[6R-[6a,7b]-7-[[(2-amino-4-thiazolyl)(methoxyimino) [acetyl] amino]-3-[[[9-cyclopropyl-6-fluoro-4,9-dihydro-7-(4-methyl-1 -piperazinyl)-4-oxo-3-isothiazolo[5,4-b]quinolinyl]oxy]methyl]-8 -oxo-5-thia-1-azabicyclo[4.2.0]oct-2-ene-2-carboxylic acid sodium salt

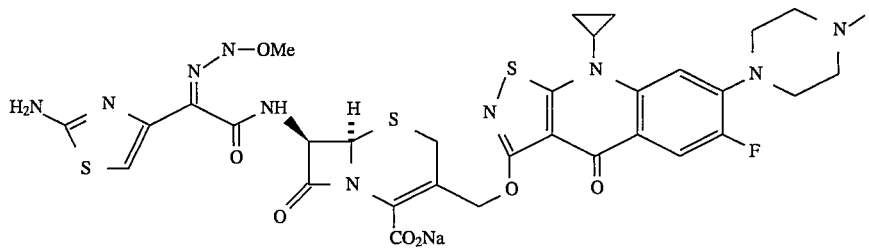

[5R-[5a,6a]]-3[[[[1-cyclopropyl-6-fluoro-1,4-dihyro-4-oxo- 7-(1-piperazinyl)-3-quinolinyl]carbonyl]amino]methyl]-6-[(R)-1 -hydroxyethyl]-7-oxo-4-thia-1-azabicyclo [3.2.0]hept-2-ene-2-carboxylic acid sodium salt

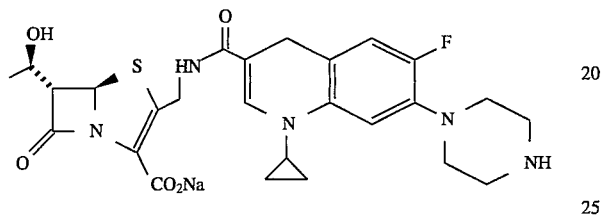

[5R-[5a,6a]]-3-[[[[7-(3-aminomethyl-1-pyrrolidinyl)-1-cyclopropyl- 6,8-difluoro-1,4-dihydro-4-oxo-3-quinolinyl] carbonyl]amino] methyl]-6-[(R)-1-hydroxyethyl]-7-oxo-1-azabicyco[3.2.0] hept-2-ene-2-carboxylic acid sodium salt

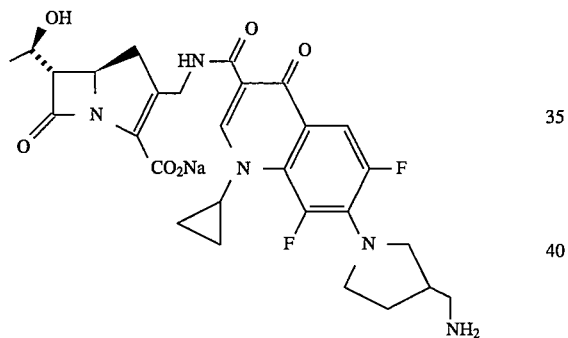

[5R-[5a,6a]-3-[[[[(3-amino-1-pyrrolidinyl)-1-(2,4-difluorophenyl)- 6-fluoro-1,4-dihydro-4-oxo-1,8-naphthyridin-3-yl]carbonyl]amino]methyl]-6-[(R)-1-hydroxyethyl]-7-oxo-1 -azabicyclo[3.2.0]hept-2-ene-2-carboxylic acid sodium salt

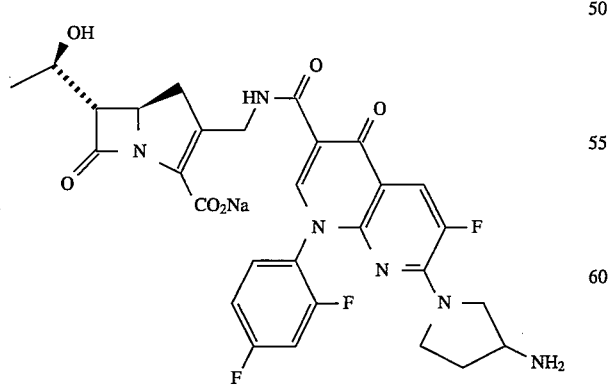

Other preferred quinolonyl lactams are exemplified by the following structures.

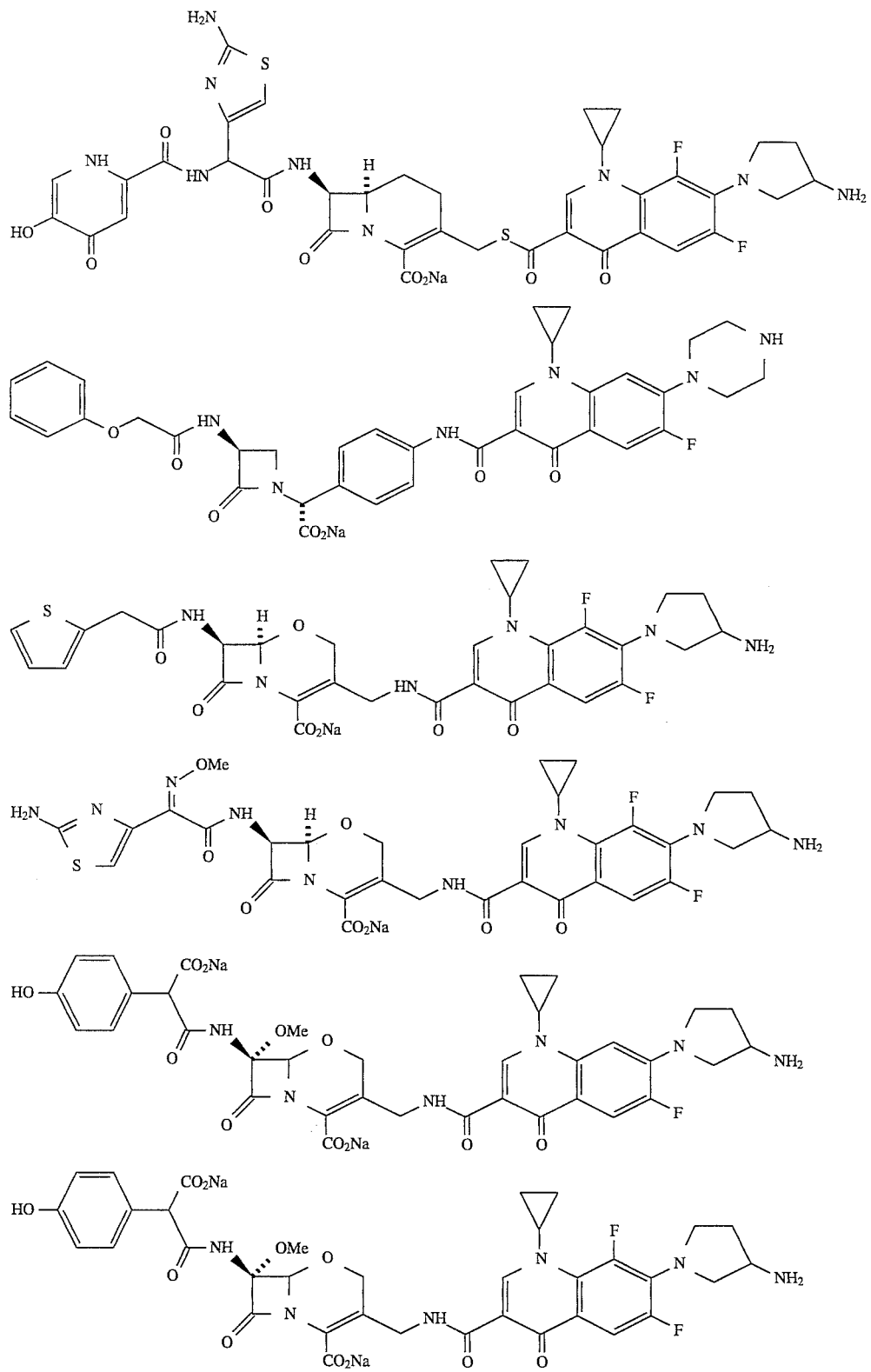

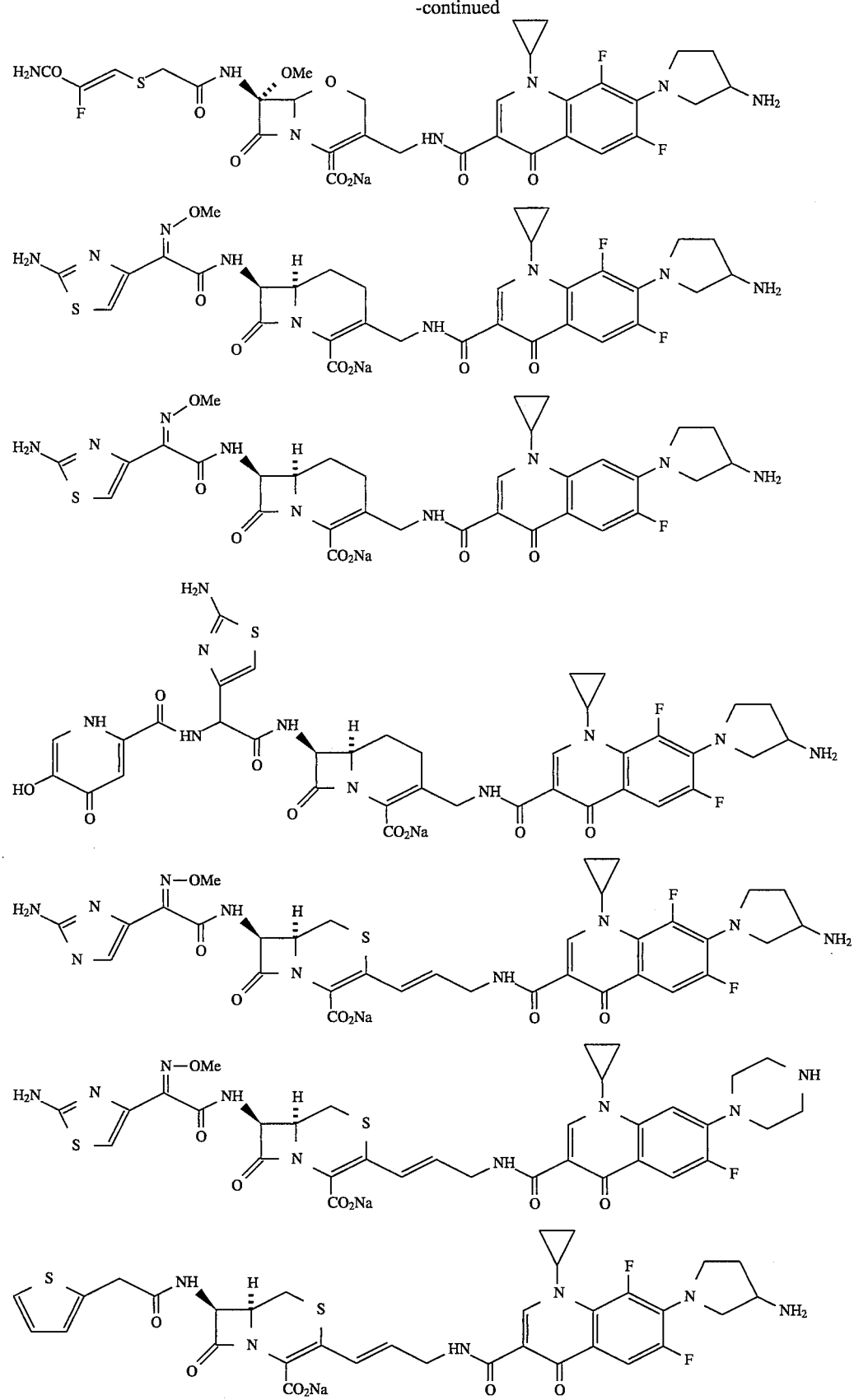

-continued
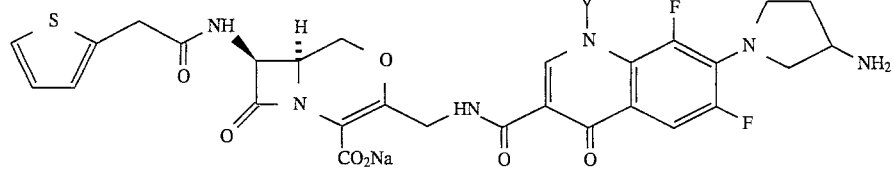
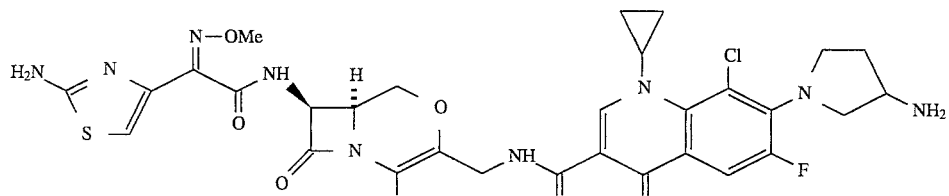
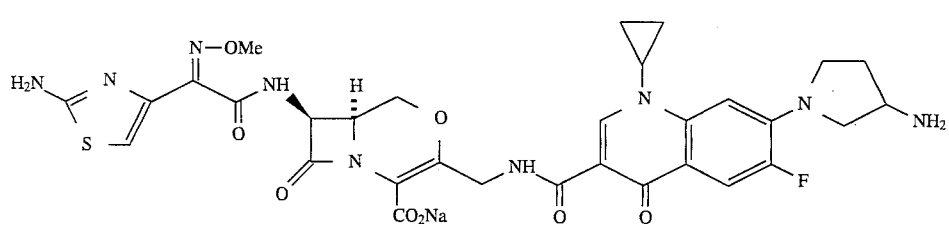
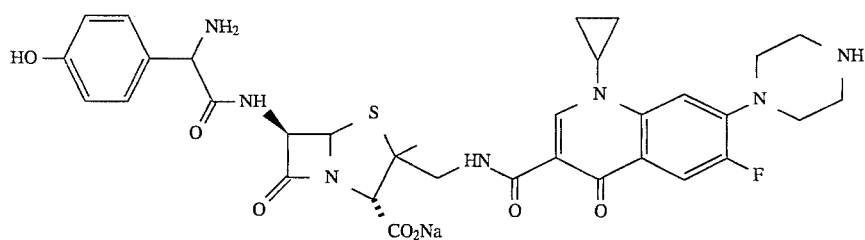
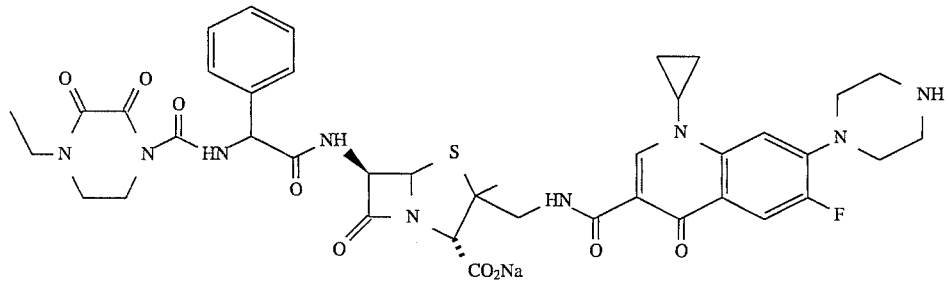
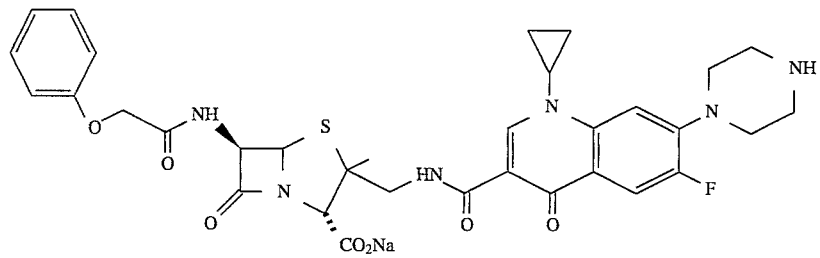
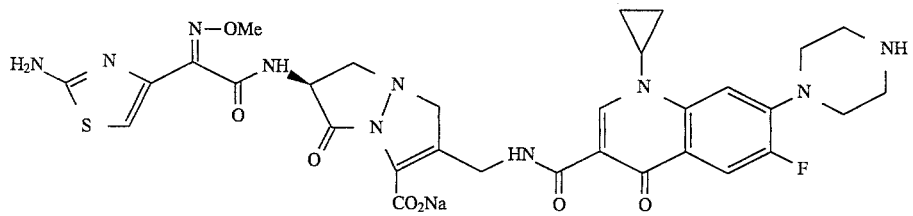

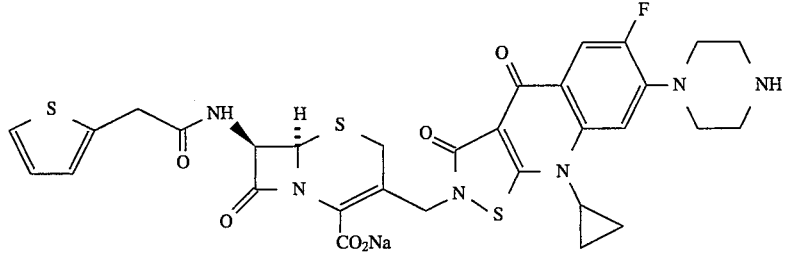
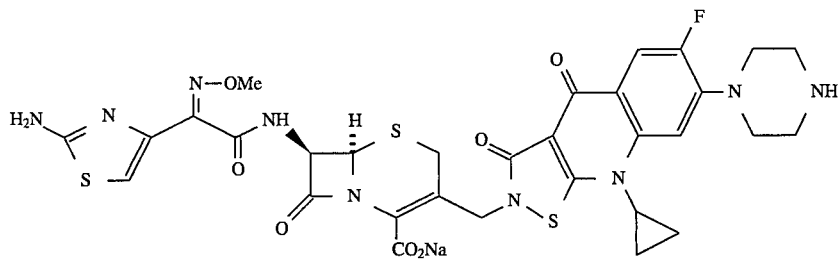
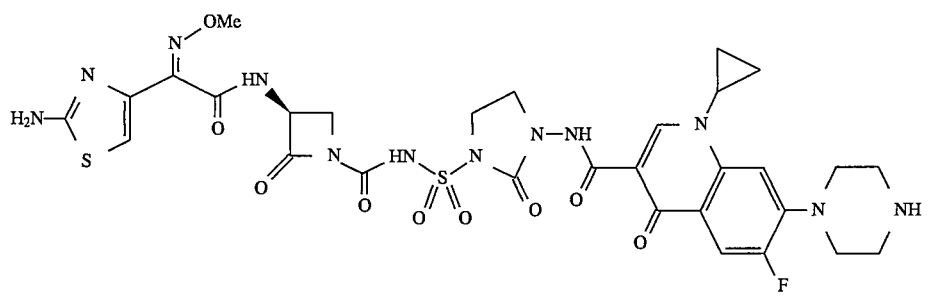
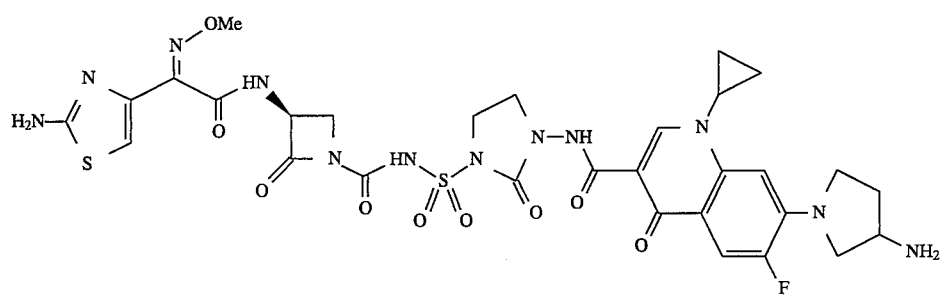
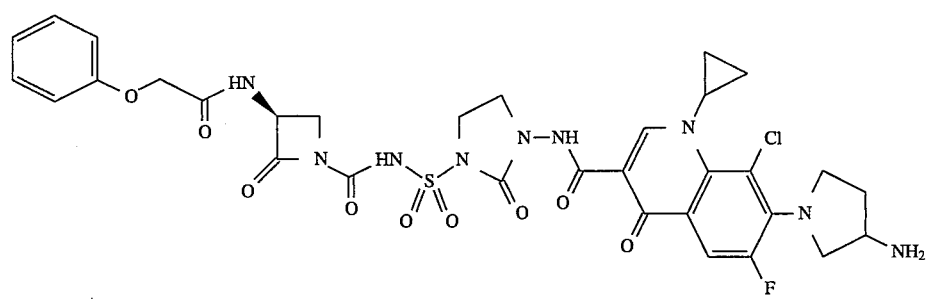
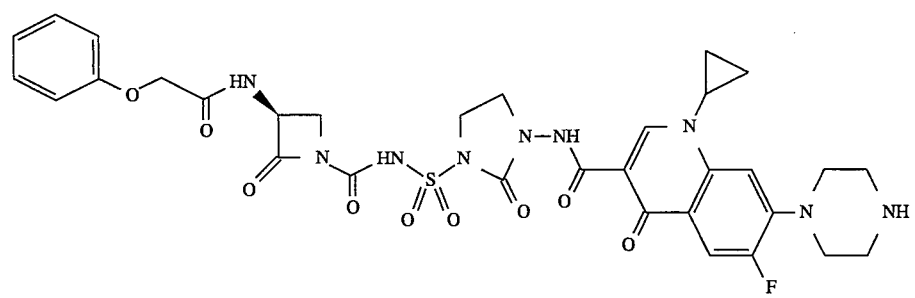

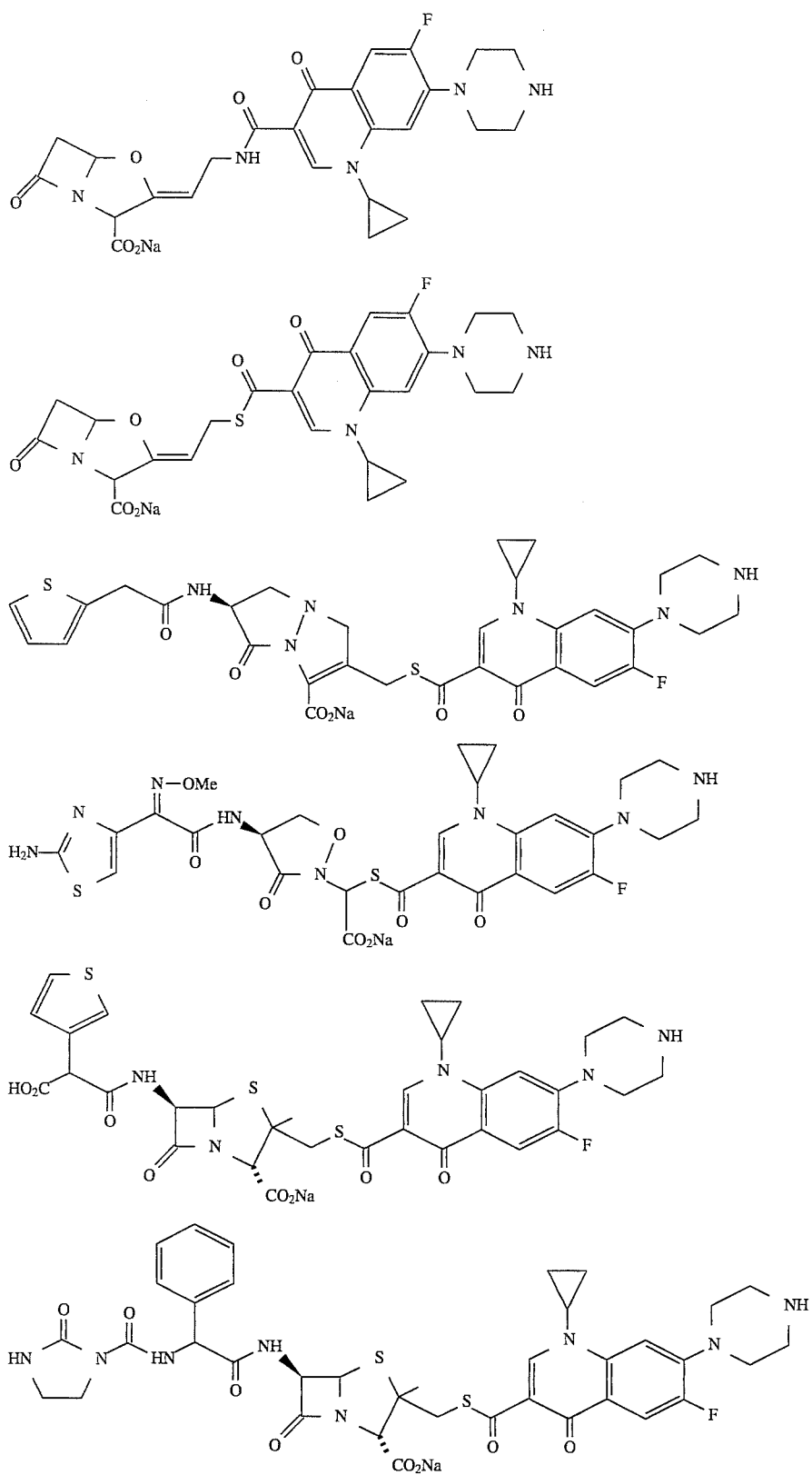

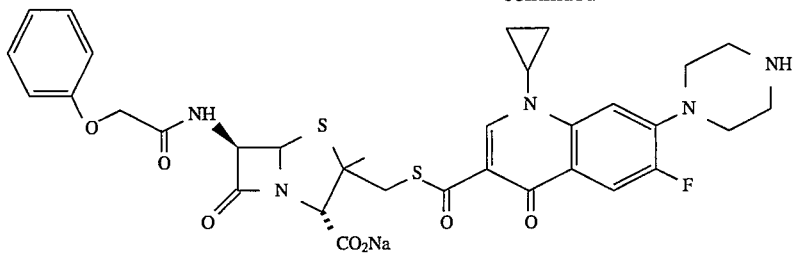
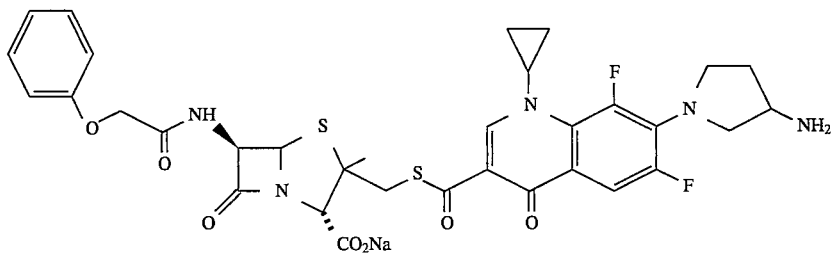
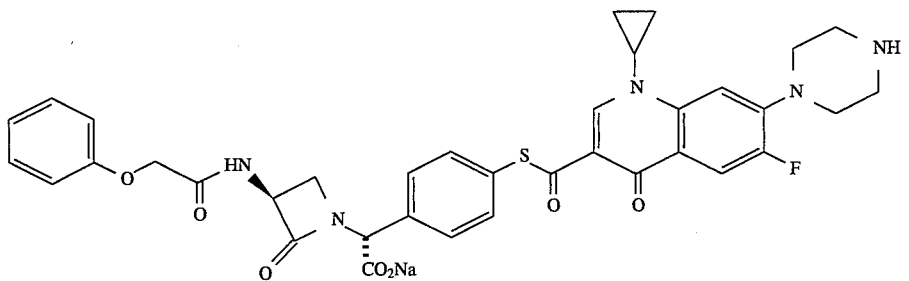
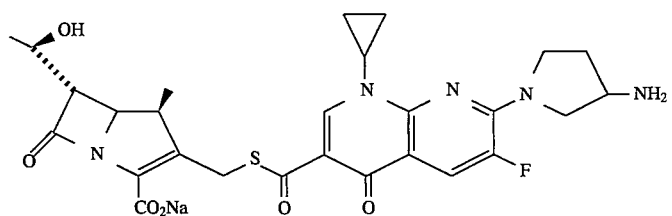
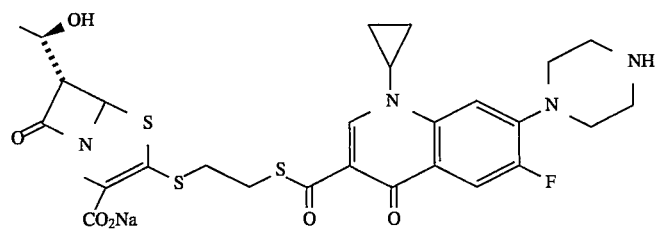
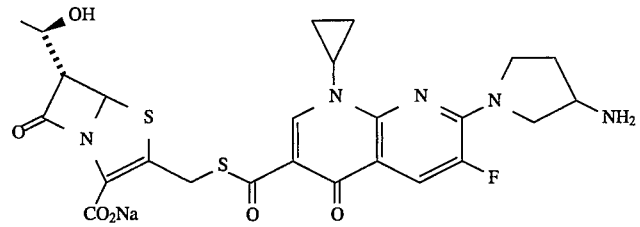
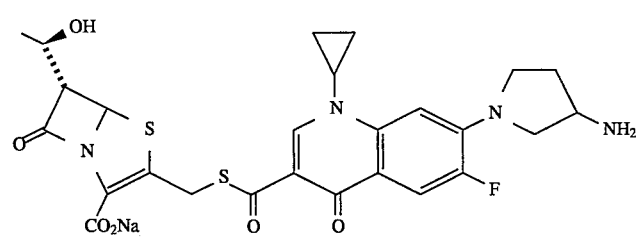

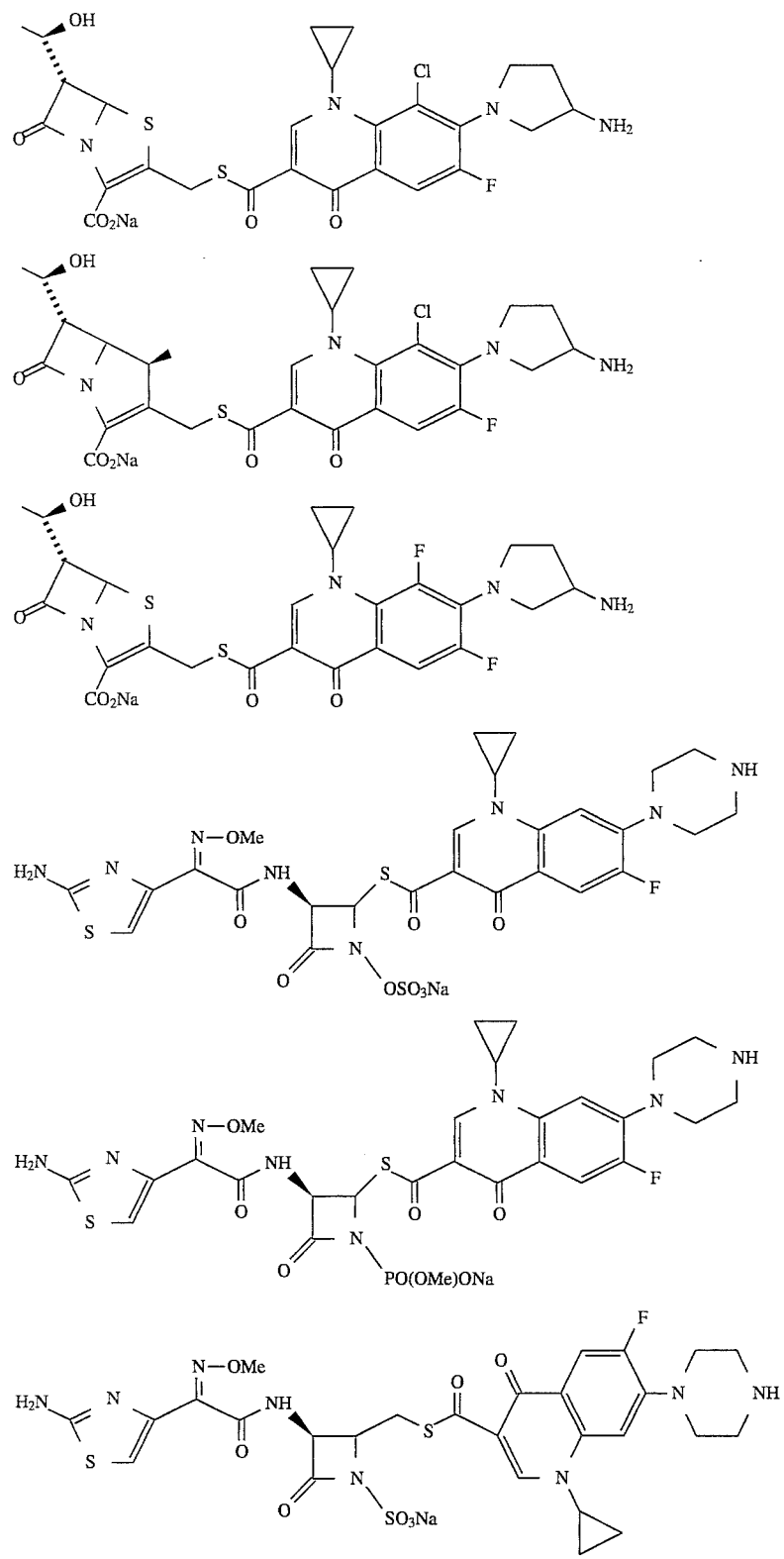

-continued
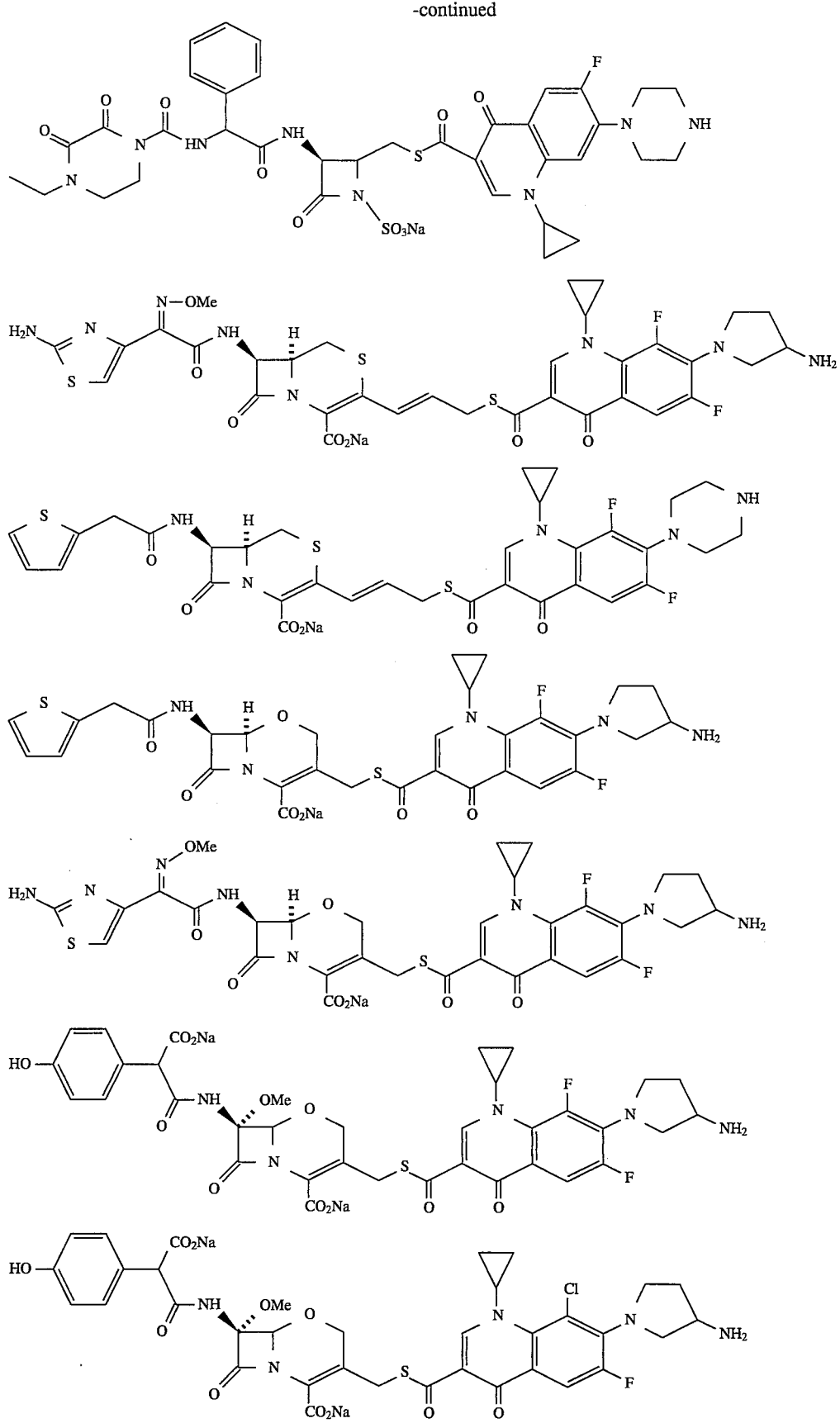

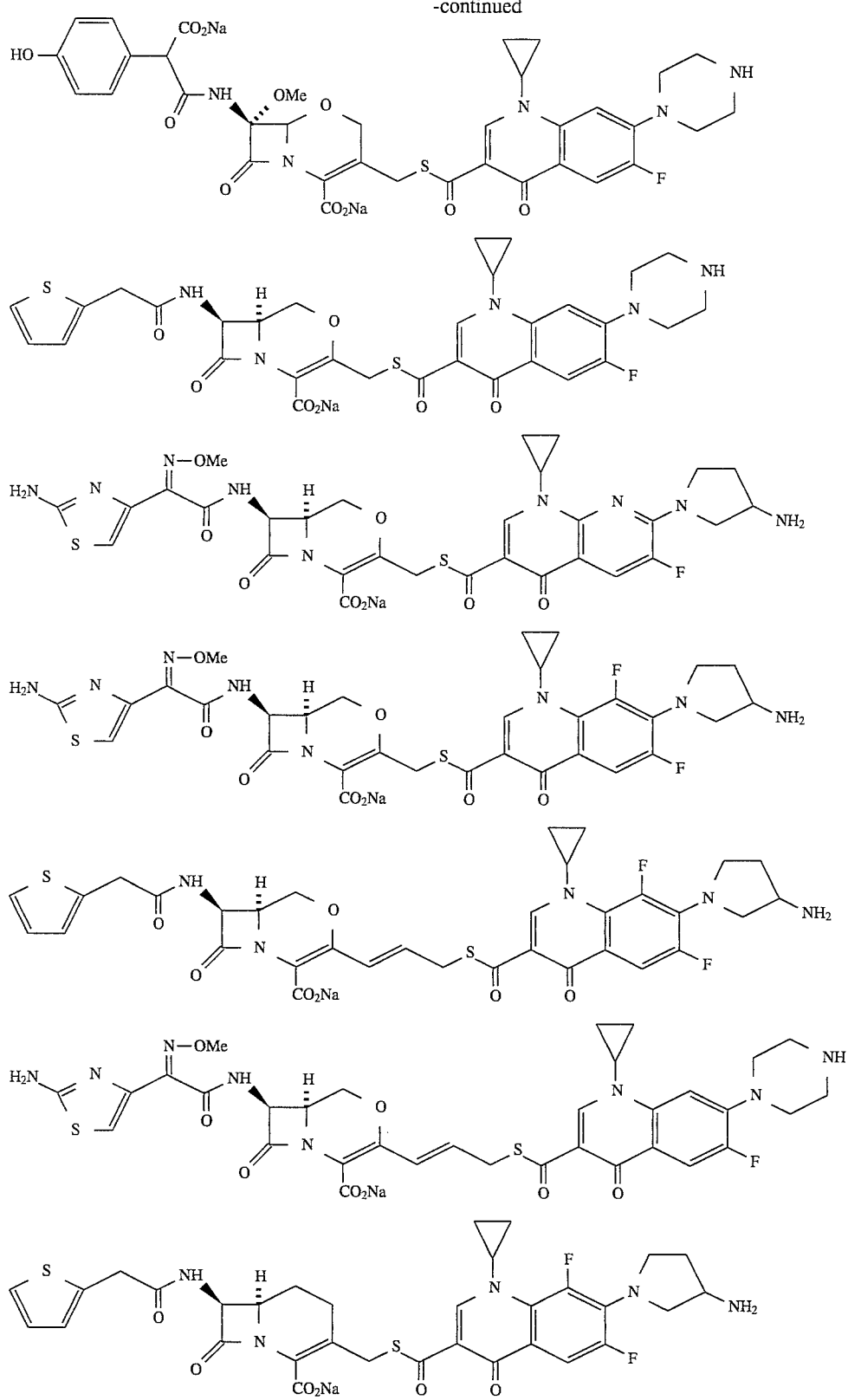

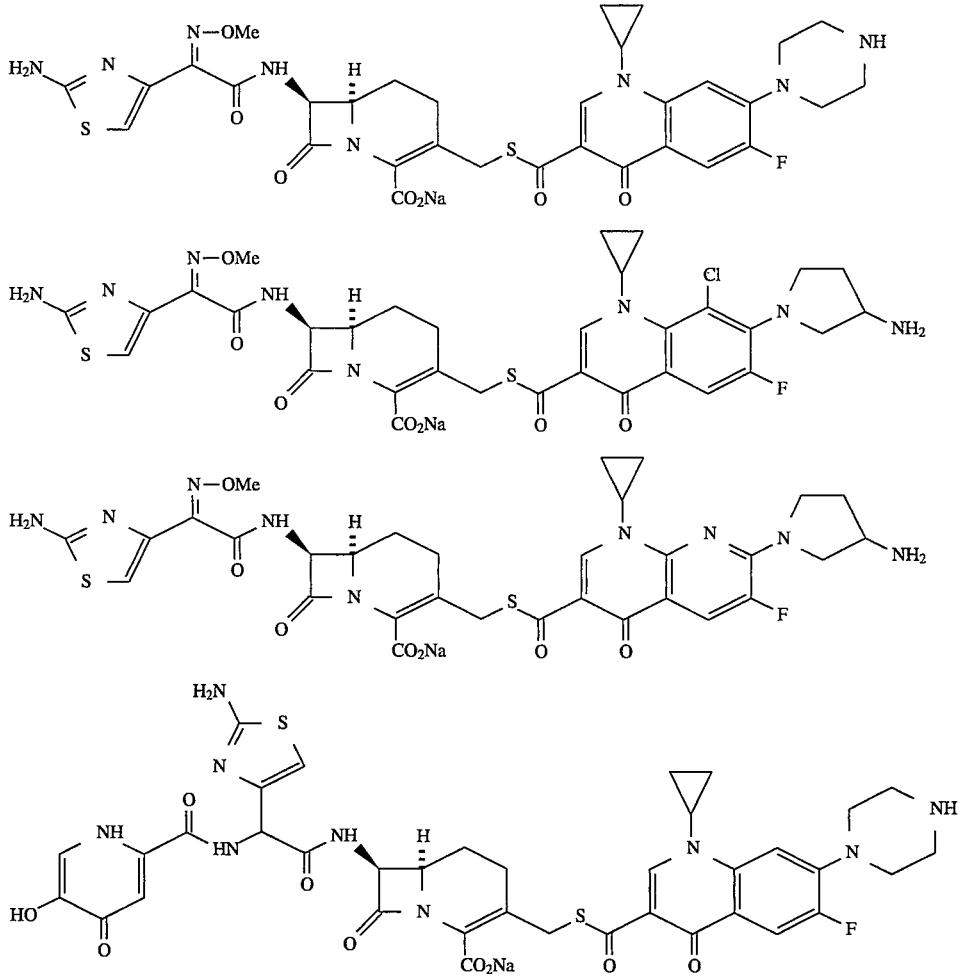

Methods of Manufacture

The quinolonyl lactams of this invention may be made using any of a variety of synthetic techniques known in the art. Manufacture of quinolonyl lactam generally involves the preparation of a lactam-containing moiety, a quinolone moiety and a procedure or set of procedures for linking the lactam-containing and quinolone moieties. Procedures for making a broad variety of lactam-containing moieties and quinolone moieties are well known in the art. For example, procedures for preparing lactam-containing moieties are described in the following references, all incorporated by reference herein (including articles cited within these references): *Cephalosporins and Penicillins: Chemistry and Biology* (E. H. Flynn, ed, 1972) Chapters 2, 3, 4, 5, 6, 7, 15 and Appendix I; *Recent Advances in the Chemistry of β-Lactam Antibiotics* (A. G. Brown and S. M. Roberts, ed., 1985); *Topics in Antibiotic Chemistry*, Vol. 3, (Part B) and Vol. 4, (P. Sommes, ed., 1980); *Recent Advances in the Chemistry of β-lactam Antibiotics* (J. Elks, ed., 1976); *Structure-Activity Relationships Among the Semisynthetic Antibiotics* (D. Perlman, ed, 1977); Chapts. 1, 2, 3, 4; *Antibiotics, Chemotherapeutics and Antibacterial Agents for Disease Control* (M. Grayson, ed, 1982); Chemistry and Biology of β-Lactam Antibiotics, Vols 1–3 (K. B. Morin and M. Gorman, eds, 1982); 4 *Medicinal Research Reviews* 1–24 (1984); 8 *Medicinal Research Review* 393–440 (1988); 24 *Angew. Chem. Int. Ed. Engl.* 180–202 (1985); 40 *J. Antibiotics* 182–189 (1987); European Patent Publication 266,060; 42 *J. Antibiotics* 993 (1989); U.S. Pat. No. 4,742,053; 35 *Chem. Pharm. Bull.* 1903–1909 (1987); 32 *J. Med. Chem.*, 601–604 (1989); U.S. Pat. No. 4,791,106; Japanese Patent Publication 62/158291; 31 *J. Med. Chem.* 1987–1993 (1988); 30 *J. Med. Chem.*, 514–522 (1987); 28 *Tet. Let.* 285–288 (1987); 28 *Tet. Let.* 289–292 (1987); 52 *J. Org. Chem.*, 4007–4013 (1987); 40 *J. Antibiotics*, 370–384 (1987); 40 *J. Antibiotics*, 1636–1639 (1987); 37 *J. Antibiotics*, 685–688 (1984); 23 *Heterocycles*, 2255–2270; 27 *Heterocycles*, 49–55; 33 *Chem. Pharm. Bull.* 4371–4381 (1985); 28 *Tet. Let*, 5103–5106 (1987); 53 *J. Org. Chem.*, 4154–4156 (1988); 39 *J. Antibiotics*, 1351–1355 (1986); 59 *Pure and Appl. Chem.*, 467–474 (1987); 1987 *J.C.S. Chem. Comm.*; 44 *Tetrahedron*, 3231–3240 (1988); 28 *Tet. Let.*, 2883–2886, (1987); 40 *J. Antibiotics*, 1563–1571 (1987); 33 *Chem. Pharm. Bull.*, 4382–4394 (1985); 37 *J. Antibiotics*, 57–62 (1984); U.S. Pat. No. 4,631,150; 34 *Chem. Pharm. Bull.*, 999–1014 (1986); 52 *J. Org. Chem.*, 4401–4403 (1987); 39 *Tetrahedron*, 2505–2513 (1983); 38 *J. Antibiotics*, 1382–1400 (1985); European Patent Application 053, 815; 40 *J. Antibiotics*, 1563–1571 (1987); 40 *J. Antibiotics*, 1716–1732 (2987); 47 *J. Org. Chem.*, 5160–5167 (1981); U.S. Pat. No. 4,777,252; U.S. Pat. No. 4,762,922; European Patent Publication 287,734; U.S. Pat. No. 4,762,827; European Patent Publication 282,895; European Patent Publication 282,365; U.S. Pat. No. 4,777,673.

Also, for example, procedures for preparing quinolones useful in the methods of this invention are described in the following references, all incorporated by reference herein (including articles listed within these references); 21 *Progress in Drug Research,* 9–104 (1977); 31 *J. Med. Chem.,* 503–506 (1988); 32 *J. Med. Chem.,* 1313–1318 (1989); 1987 *Liebigs Ann. Chem.,* 871–879 (1987); 14 *Drugs Exptl. Clin. Res.,* 379–383 (1988); 31 *J. Med. Chem.,* 983–991 (1988); 32 *J. Med. Chem.,* 537–542 (1989); 78 *J. Pharm. Sci.,* 585–588 (1989); 26 *J. Het. Chem., (1989)*; 24 *J. Het. Chem.,* 181–185 (1987); U.S. Pat. No. 4,599,334, 35 *Chem. Pharm. Bull.,* 2281–2285 (1987); 29 *J. Med. Chem.,* 2363–2369 (1986); 31 *J. Med. Chem.,* 991–1001 (1988); 25 *J. Med. Chem.,* 479–485 (1988); European Patent Publication 266,576; European Patent Publication 251,308, 36 *Chem. Pharm. Bull.,* 1223–1228 (1988); European Patent Publication 227,088; European Patent Publication 227,039; European Patent Publication 228,661; 31 *J. Med. Chem.,* 1586–1590 (1988); 31 *J. Med. Chem.,* 1598–1611 (1988); and 23 *J. Med. Chem.,* 1358–1363 (1980).

Procedures for linking the lactam-containing moiety and quinolone moieties may vary according to the type of linking group desired. For example, quinolonyl lactams having a thioester linking moiety may be made by the following general reaction sequence:

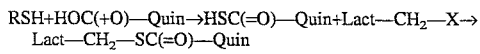
RSH+HOC(+O)—Quin→HSC(=O)—Quin+Lact—CH₂—X→ Lact—CH₂—SC(=O)—Quin where X is a reactive leaving group (such as halo, a sulfonate ester, acetate, thiobenzoate or other activated hydroxyl functionality. Lact generically represents an appropriately protected lactam-containing moiety (such as a penem, carbapenem, cephem, monocyclic beta-lactam, oxacephem, or carbacephem), and "Quin" represents an appropriately protected quinolone moiety. The sequence can be invisioned as formation of the intermediate quinolone thioacid, followed by nucleophilic displacement of the lactam X substituent to form a thioester coupled conjugate of the lactam and quinolone.

Quinolonyl lactams having a hydrazone or hydrazide linking moiety may be made by the following general reaction sequence:

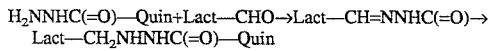
H₂NNHC(=O)—Quin+Lact—CHO→Lact—CH=NNHC(=O)→ Lact—CH₂NHNHC(=O)—Quin where "Lact" generically represents an appropriately protected lactam-containing moiety (such as a penem, carbapenem, cephem, monocyclic beta-lactam, oxacephem, or carbacephem) and Quin represents an appropriately protected quinolone moiety. The sequence can be envisioned as the condensation of the quinolone hydrazide with a lactam aldehyde or ketone to form the hydrazone coupled lactam quinolone conjugate. Subsequent reduction yields the corresponding hydrazide coupled lactam quinolone conjugate.

Quinolonyl lactams having an amide linking moiety may be made by the following general reaction sequence:

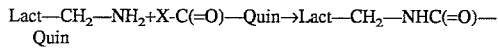
Lact—CH₂—NH₂+X-C(=O)—Quin→Lact—CH₂—NHC(=O)— Quin where X is a reactive leaving group (such as halo, an HOBt ester, mixed anhydride or other activated carboxyl functionality), "Lact" generically represents an appropriately protected lactam containing structure (such as penem, carbapenem, cephem, oxacephem, or carbacephem),, and "Quin" represents an appropriately protected quinolone. The reaction can be envisioned as an acylation of the lactam amino substituent with the activated quinolone carboxyl group, to form an amide coupled conjugate of the lactam and quinolone.

In the reaction sequences described herein, certain functional groups contained in the Lact and Quin structures (such as carboxyl, hydroxyl, and amino groups) may need to be blocked in order to prevent undesired, competing side reactions. Suitable protecting groups for carboxyl substituents include esters; protecting groups for hydroxyl substituents include ethers, esters, and carbonates; and protecting groups for amino substituents include carbamates and amides. If such protecting groups are employed, then appropriate deprotecting chemistry, that will not decompose the coupled conjugate, may be required to obtain antimicrobially active products.

Compositions

The compositions of this invention comprise:
(a) a safe and effective amount of a quinolonyl lactam; and
(b) a pharmaceutically-acceptable carrier.

A "safe and effective amount" of a quinolonyl lactam is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the quinolonyl lactam therein, and the dosage regimen desired for the composition.

The compositions of this invention are preferably provided in unit dosage form. As used herein, a "unit dosage form" is a composition of this invention containing an amount of a quinolonyl lactam that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 1500 mg, of a quinolonyl lactam.

The compositions of this invention may be in any of a variety of forms, suitable (for example) for oral, rectal, topical, or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolonyl lactam. The amount of carrier employed in conjunction with the quinolonyl lactam is sufficient to provide a practical quantity of material for administration per unit dose of the quinolonyl lactam. Techniques and compositions for making dosage forms useful in the methods of this invention are described in the following references, all incorporated by reference herein: 7 *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the quinolonyl lactam. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolonyl lactam. Suitable carriers for topical administration preferably remain in place on the skin as a continuous film, and resist being removed by perspiration or immersion in water. Generally, the carrier is organic in nature and capable of having dispersed or dissolved therein the quinolonyl lactam. The carrier may include pharmaceutically-acceptable emolients, emulsifiers, thickening agents, and solvents.

Methods of Administration

This invention also provides methods of treating or preventing an infectious disorder in a human or other animal subject, by administering a safe and effective amount of a quinolonyl lactam to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients.

The quinolonyl lactams and compositions of this invention can be administered topically or systemically. Systemic application includes any method of introducing the quinolonyl lactam into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific quinolonyl lactam used, the resistance pattern of the infecting organism to the quinolonyl lactam used, the ability of the quinolonyl lactam to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of quinolonyl lactam are administered per day. Treatment regimens preferably extend from about 3 to about 56 days, preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 1500 mg, are acceptable.

A preferred method of systemic administration is oral. Individual doses of from about 100 mg to about 2500 mg, preferably from about 250 mg to about 1000 mg are preferred.

Topical administration can be used to deliver the quinolonyl lactam systemically, or to treat a local infection. The amounts of quinolonyl lactam to be topically administered depends upon such factors as skin sensitivity, type and location of the tissue to be treated, the composition and carrier (if any) to be administered, the particular quinolonyl lactam to be administered, as well as the particular disorder to be treated and the extent to which systemic (as distinguished from local) effects are desired.

The following non-limiting examples illustrate the compounds, compositions, processes, and uses of the present invention.

EXAMPLE 1

[5R-[5a,6a] -3-[[[1-Cyclopropyl-6,8-difluoro-1,4-dihydro 4-oxo-7-(3-aminomethyl-1-pyrrolidinyl)-3-quinolinyl] carbonylamino] methyl]-6-[(R)-1-hydroxyethyl]-7-oxo-4-thia-1-azabicyclo[3.2.0] hept-2-ene-2-carboxylic acid, according to this invention, is made by the following general reaction sequence.

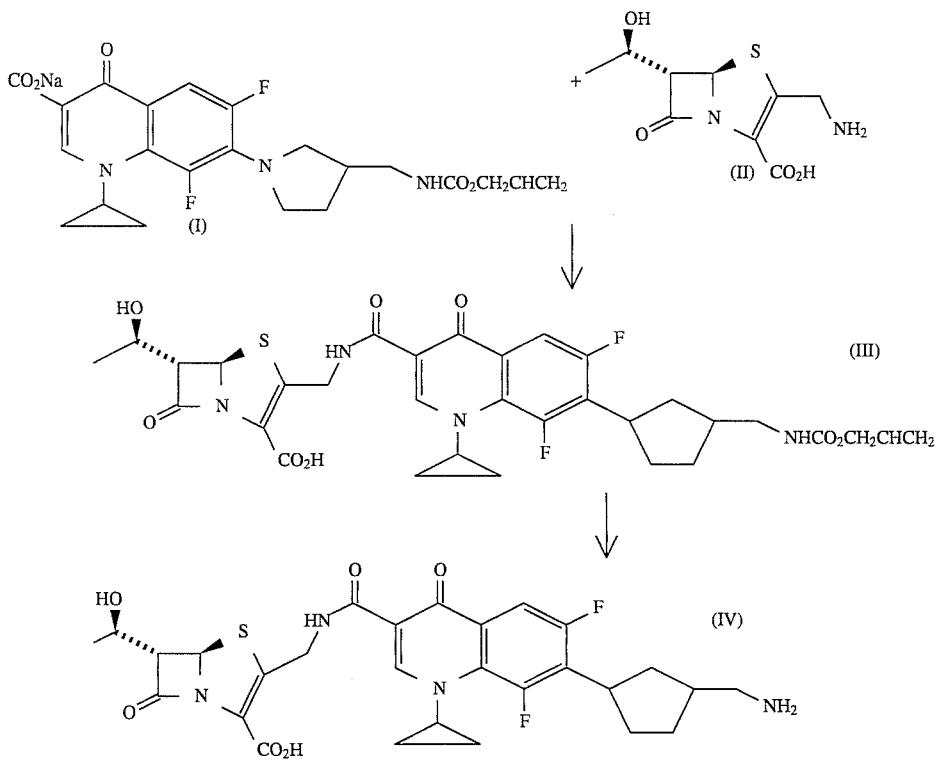

Approximately 0.73 g (1.5 millimoles) of 1-(cyclopropyl)-6,8-difluoro-1,4-dihydro-4-oxo-7-[ 3-[(2-propenyl)oxycarbonyl]-aminomethyl]-1-pyrrolidinyl]-3-quinoline carboxylic acid, sodium salt, (I) is dissolved in 30 ml anhydrous dioxane, and 1.1 equivalent of sodium bicarbonate and 6 ml of acetone are added. Compound (I) prepared from 1-cyclopropyl-6,8-difluoro-1,4-dihydro-4-oxo-7-(3-aminomethyl 1-pyrrolidinyl)-3-quinoline carboxylic acid (J. Sanchez, et al., 31 *J. Med. Chem.* 9383 (1988) by standard methods.) The reaction solution is cooled to approximately 0° C. (32° F.) and 1.1 equivalent of isobutylchloroformate is added slowly with stirring. The reaction is maintained at approximately 2° C. (36° F.) for approximately 1 hour.

Approximately 1 mmol (244 mg) of [5R[5a,6a]]-3-aminomethyl-6-[ (R)-1-hydroxyethyl]-7-oxo-4-thia-1-azabicyclo[3.2.0]hept-2-ene-2-carboxylic acid (II, made according to 69 *Helv. Chim. Acta* 1576 (1986), is dissolved in 10 ml of 30% aqueous dioxane, containing 1 additional mmol of sodium bicarbonate. This solution is added to the above reaction mixture, and the mixture stirred for an additional 60 min. at approximately 2° C. The reaction is quenched with the addition of 1.3 mmol sodium bicarbonate in 70 ml ice water. After extracting with ether, the aqueous layer is acidified to approximately pH 2 and is exhaustively extracted with methylene chloride. The solid Product (III) is then obtained.

Approximately 350 mg (0.5 mmol) of Product (III) is dissolved in 20 ml THF (tetrahydrofuran) containing 0.5 mmol sodium bicarbonate. At room temperature, under a nitrogen blanket, 14 mg of triphenylphosphine, 122 mg of sodium ethylhexanoate, and 14 mg of tetrakis(triphenylphosphine)palladium are added. The reaction mixture is stirred for approximately 1 hr during which time a precipitate forms. The solid final product (IV) is collected by filtration and purified by repeated trituration with acetone.

Similarly, the following quinolonyl lactams are prepared by the general procedure of this Example, with substantially similar results.

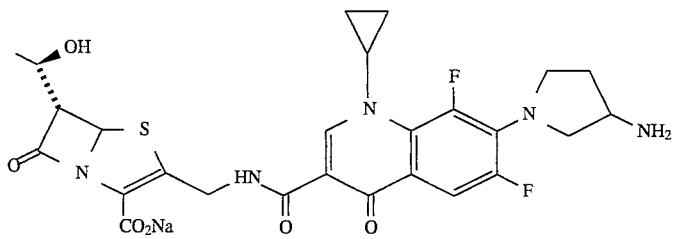

of sodium bicarbonate. This solution is added to the above reaction mixture, and the mixture stirred for an additional 60 min. at approximately 2° C. The reaction is quenched with the addition of 1.3 mmol sodium bicarbonate in 70 ml ice using the quinolone 7-(3-aminopyrrolidinyl)-1-cyclopropyl-6,8-difluoro-1,4-dihydro 4-oxo-3-quinoline carboxylic acid (prepared according to J. P. Sanchez, et. al., J. Med. Chem., 1988, 31,983)

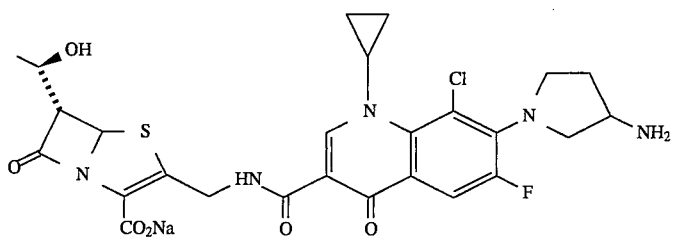

using the quinolone 7-(3-aminopyrrolidinyl)-1-chloro-1-cyclopropyl-6-fluoro-1,4-dihydro 4-oxo-3quinoline carboxylic acid (prepared according to J. P. Sanchez, et. al., J. Med. Chem., 1988, 31,983)

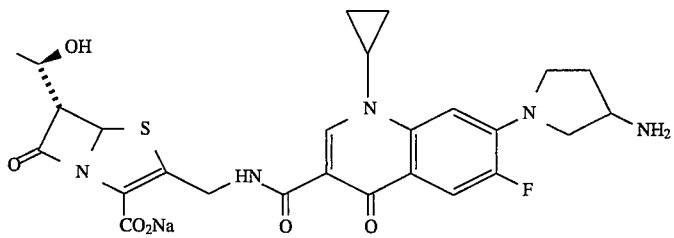

using the quinolone 7-(3-aminopyrrolidinyl-1-cyclopropyl-6-fluoro-1,4-dihydro-4-oxo-3-quinoline carboxylic acid (prepared according to J. P. Sanchez, et. al., J. Med. Chem., 1988, 31,983)

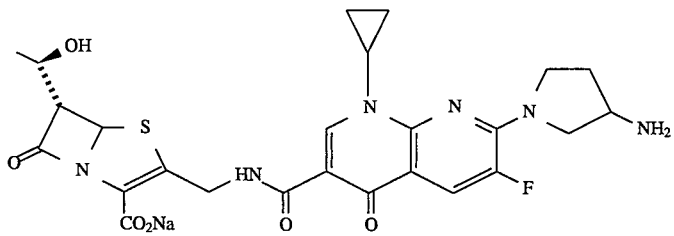

using the naphthyridinone 7-(3-aminopyrrolidinyl)-1-cyclopropyl-6-fluoro-1,4-dihydro 4-oxo-1,8-napthyridine-3-carboxylic acid (prepared according to J. P. Sanchez, et. al., J. Med. Chem., 1988, 31,983 )

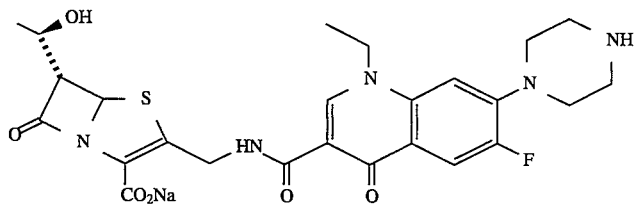

using the quinolone 1-ethyl-6-fluoro-1,4-dihydro-4-oxo-7-(1-piperazinyl) 3-quinoline carboxylic acid (prepared according to H. Koga, et. al., J. Med. Chem., 1980, 23, 1358)

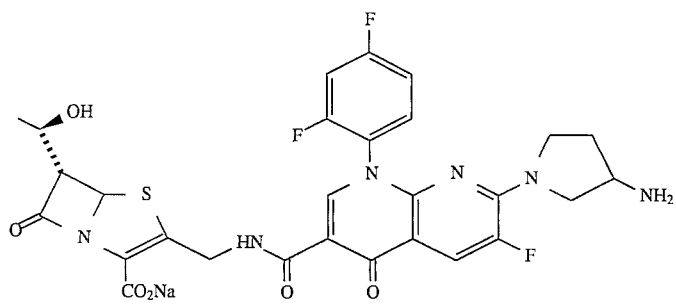

using the naphthyridinone 7-(3-aminopyrrolidinyl)-1-(2,4-difluorophenyl)-6-fluorol, 4-dihydro-4-oxo-1,8-napthyridine-3-carboxylic acid (prepared according to D. T. W. Chu, et. al., J. Med. Chem., 1986, 29, 2363 )

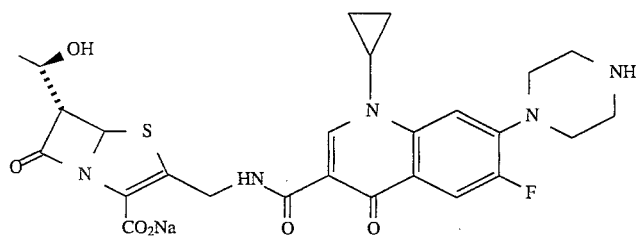

using the quinolone 1-cyclopropyl-6-fluoro-1,4-dihydro-4-oxo-7-(1-piperazinyl) 3-quinoline carboxylic acid (prepared according to K. Grohe, et al., Ger. Offen. DE 3142854)

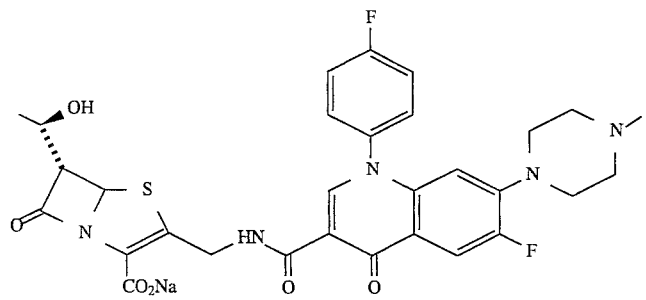

using the quinolone 6-fluoro-1-(4-fluorophenyl)-1,2-dihydro-4-oxo-7-(1-piperazinyl) 3-quinoline carboxylic acid (prepared according to D. T. W. Chu, et. al., J. Med. Chem., 1985, 28, 1558)

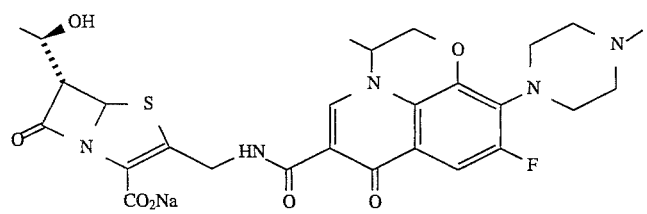

using the quinolone 9-fluoro-4,7-dihydro-3-methyl-10-(1-piperazinyl) 7-oxo-2H-pyrido[1,2,3-de]-1,4-benzoxazine-6-carboxylic acid (prepared according to I. Hayakawa, et. al., Chem. Pharm. Bull., 1984, 32, 4907)

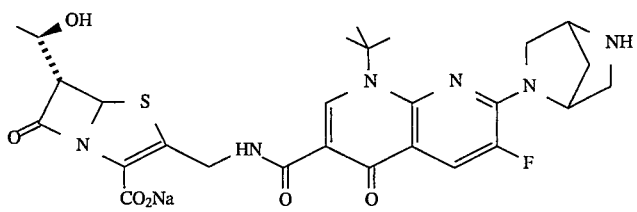

using the naphthyridinone 7-(2,5-diazabicyclo[2.2.1]heptan-2-yl) 1- (1,1-dimethyl ethyl)-6-fluoro-1,4-dihydro-4-oxo-1,8-naphthyridine-3 carboxylic acid (prepared according to A. Weber, et. al., EP 266576)

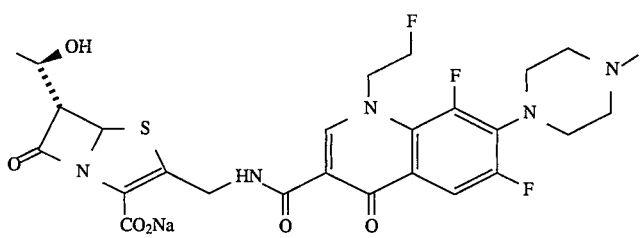

using the quinolone 1-(2-fluoroethyl)-6,8-difluoro--1,4-dihydro-4-oxo-7-(4 methyl-1-piperazinyl)-3-quinoline carboxylic acid (prepared according to T. Irikura, Aust. Pat. Specif. AU 537813).

EXAMPLE 2

According to the general procedure of Example 1, the following quinolonyl lactam is made:

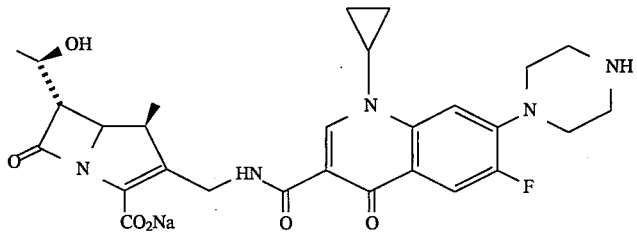

using the beta-lactam 3-(aminomethyl)-6-(1-hydroxyethyl)-4-methyl-7-oxo-1-azabicyclo [4.2.0]hept-2-ene-2-carboxylic acid (prepared according to B. G. Christesen, et al., Eur. Pat. Appl. EP 292191)

Similarly, the following quinolonyl lactam is prepared by the general procedure of this Example, with substantially similar results.

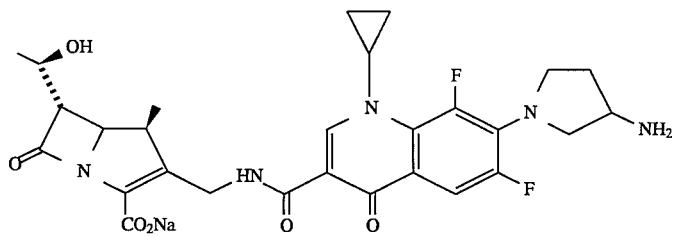

using the quinolone 1-(2-fluoroethyl)-6,8-difluoro-1,4-dihydro-4-oxo-7-(4-methyl 1-piperazinyl)-3-quinoline carboxylic acid (prepared according to T. Irikura, Aust. Pat. Specif. AU 537813).

EXAMPLE 3

According to the general procedure of Example 1, the following quinolonyl lactam is made:

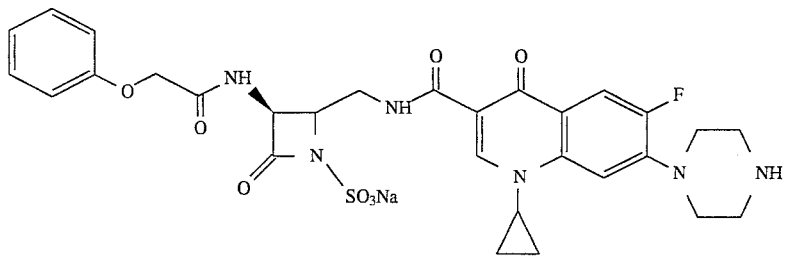

using the beta-lactam N-[2-(aminomethyl)-4-oxo-3-azetidinyl]-2-phenoxy-acetamide (prepared according to J. G. Gleason, et. al., U.S. Pat. No. 4,200,572)

Similarly, the following quinolonyl lactams are prepared by the general procedure of this Example, with substantially similar results.

using the quinolone 7-(3-aminopyrrolidinyl-1-cyclopropyl-6-fluoro-1,4-dihydro-4-oxo 3-quinoline carboxylic acid (prepared according to J. P. Sanchez, et. al., J. Med. Chem., 1988, 31, 983)

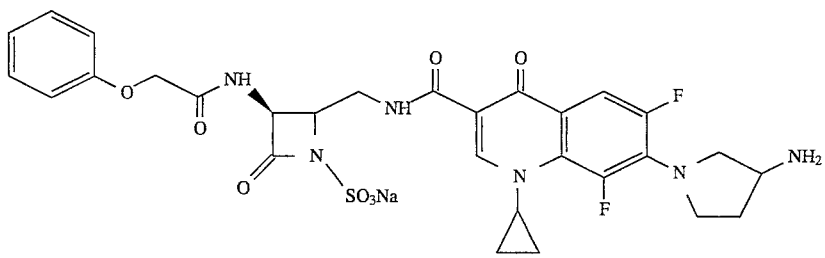

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983)

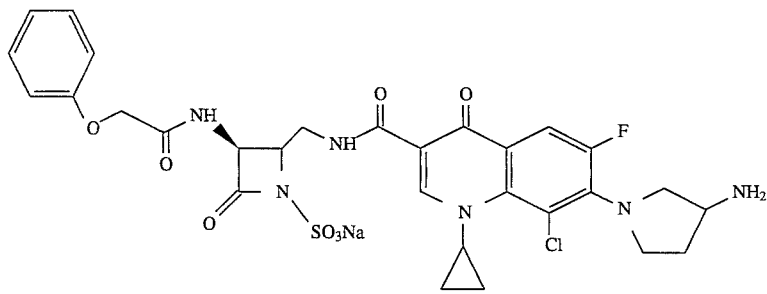

using the quinolone 7-(3-aminopyrrolidinyl)-1-chloro-1-cyclopropyl 6-fluoro-1,4-dihydro-4-oxo-3-quinoline carboxylic acid (prepared according to J. P. Sanchez, et. al., J. Med. Chem., 1988, 31, 983)

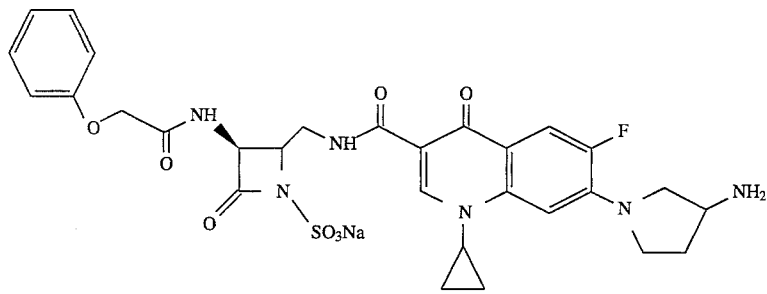

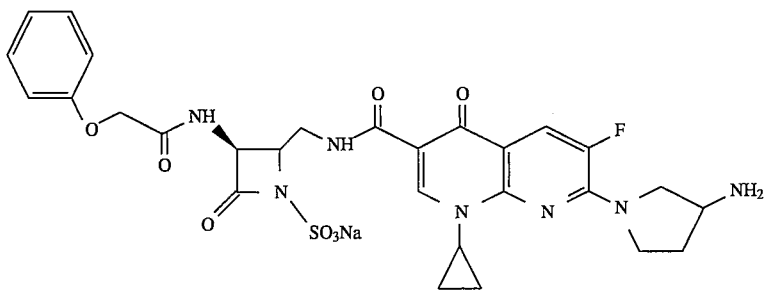

using the naphthyridinone 7-(3-aminopyrrolidinyl)-1-cyclopropyl-6-fluoro-1,4-dihydro-4-oxo 1,8-naphthyridine-3-carboxylic acid (prepared according to J. P. Sanchez, et. al., J. Med. Chem., 1988, 31, 983)

EXAMPLE 4

[6R-[8α,7β]]-3-[[(1-cyclopropyl-6-fluoro-1,4-dihydro-4-oxo-7 (1-piperazinyl)-3-quinolinyl)carbonylamino]methyl]-8-oxo-7 [(2-thienylacetyl)amino]-5-thia-1-azabicyclo[4.2.0]oct-2-ene-2-carboxylic Acid Sodium Salt

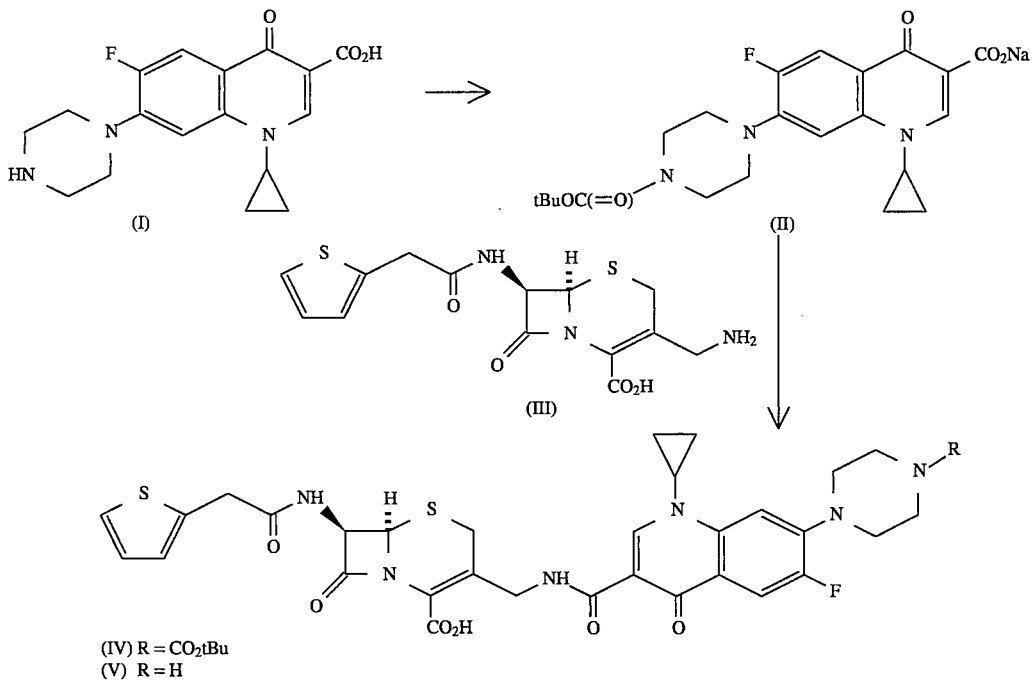

(IV) R = CO₂tBu
(V) R = H

To a solution of approximately 1.7 gm 1-cyclopropyl-6-fluoro-1,4-dihydro-4-oxo 7-(1-piperazinyl)-3-quinoline carboxylic acid (I) in 20 ml water, 5 ml 1N sodium hydroxide and 20 ml dioxane is added approximately 1.7 gm di-t-butyl carbonate. The reaction is stirred at room temperature for approximately 6 hours and is concentrated to approximately 5 ml in vacuo. The mixture is diluted with acetone and the product (II) is collected by filtration.

Separately, reactant (III) was prepared by heating a mixture of approximately 5.0 gm of commercial cephalothin sodium salt 1.06 gm sodium bicarbonate and 0.82 gm sodium azide in 75 ml water at approximately 50° C. for 18 hours. The reaction is cooled to approximately 3°–5° C., covered with ethyl acetate and slowly acidified with cold 1N HCl. The mixture is extracted 3× with ethyl acetate and the combined organic layers are dried over sodium sulfate and concentrated to dryness.

This intermediate (3.0 gm) is combined with 3.0 gm 10% Pd/C, 4.5 gm sodium bicarbonate and 100 ml 50% methanol/water, and hydrogenated at 30–40 psi and room temperature until theoretical uptake of hydrogen is observed. The catalyst is removed by filtration and the filtrate is concentrated to dryness. The residue is dissolved in water, acidified with cold 1N HCl and washed with methylene chloride. The aqueous phase is reduced in volume and added to a Dowex 50W-X4 ion exchange column. Elution with 2% pyridine/MeOH then affords reactant (III).

To 1.9 gm of product (II) in 75 ml anhydrous dioxane containing 0.41 gm sodium bicarbonate at 0°–3° C. is added 0.66 gm isobutyl chloroformate in 15 ml acetone slowly with stirring. The reaction is maintained at 0°–3° C. for approximately 2 hours. To this solution is added 1.33 gm reactant (III) dissolved in 40 ml 30% aqueous dioxane containing 0.35 gm additonal sodium bicarbonate. The mixture is allowed to come to room temperature during the addition and then stirred a further 2 hours. The reaction is then poured into 100 ml ice water containing 0.5 gm sodium bicarbonate and extracted with ethyl acetate. The aqueous layer is the acidified and is extracted 5× with an equal volume of methylene chloride. The organic phase is then dried over sodium sulfate and concentrated to dryness to obtain product (IV) after trituration with acetone/hexanes.

To a suspension of 1.2 gm of product (IV) in 30 ml methylene chloride is added 30 ml trifluoroacetic acid at room temperature. The reaction is stirred at room temperature for 4 hours and then concentrated to dryness. The residue is resuspended in methylene chloride and reconcentrated several times. The residue is then trituated with acetone to obtain product (V) after filtration.

Similarly, the following quinolonyl lactams are prepared by the general procedure of this Example, with substantially similar results.

6-fluoro-1,4-dihydro 4-oxo-3-quinoline carboxylic acid (prepared according to J. P. Sanchez, et. al., J. Med. Chem., 1988, 31, 983)

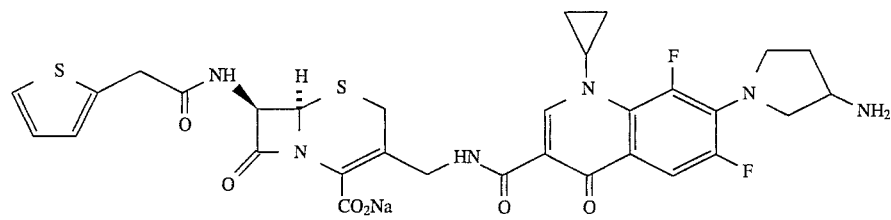

using the quinolone 7-(3-aminopyrrolidinyl)-1-cyclopropyl-6,8-difluoro-1,4-dihydro 4-oxo-3-quinoline carboxylic acid (prepared according to J. P. Sanchez, et. al., J. Med. Chem., 1988, 31, 983)

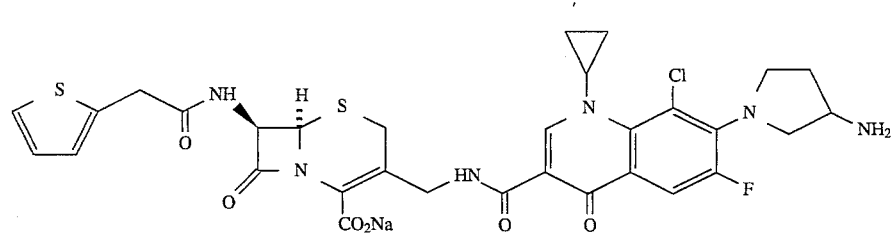

using the quinolone 7-(3-aminopyrrolidinyl)-1-chloro-1-cyclopropyl-6-fluoro-1,4-dihydro 4-oxo-3-quinoline carboxylic acid (prepared according to J. P. Sanchez, et. al., J. Med. Chem., 1988, 31, 983)

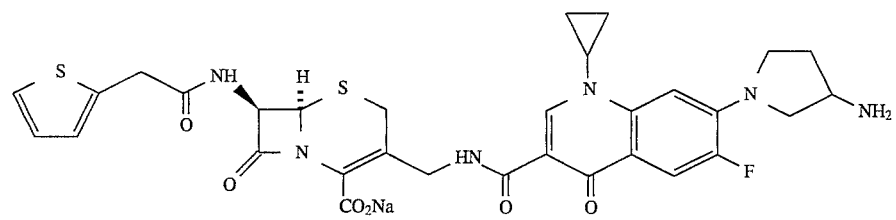

using the quinolone 7-(3-aminopyrrolidinyl-1-cyclopropyl-

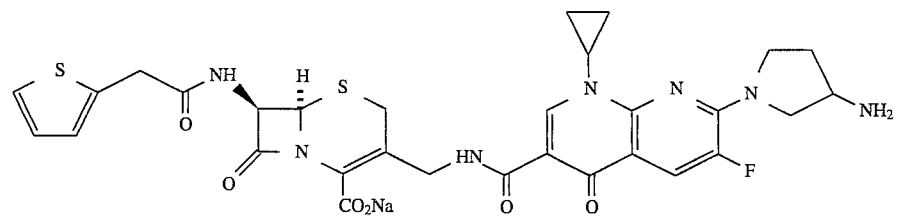

using the naphthyridinone 7-(3-aminopyrrolidinyl )-1-cyclopropyl-6-fluoro-1,4-dihydro 4-oxo-1,8-naphthyridine-3-carboxylic acid (prepared according to J. P. Sanchez, et. al., J. Med. Chem., 1988, 31, 983)

using the quinolone 9-fluoro-4,7-dihydro-3-methyl-10-(1-piperazinyl)7-oxo-2H-pyrido [1,2,3-de]-1,4-benzoxazine-6-carboxylic acid (prepared according to I. Hayakawa, et. al., Chem. Pharm. Bull., 1984, 32, 4907)

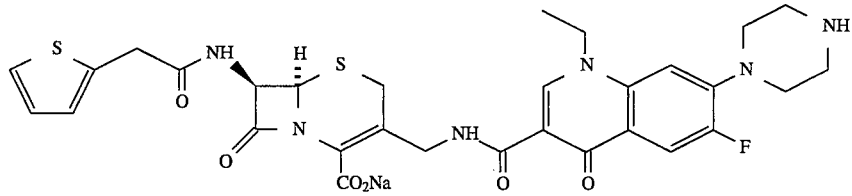

using the quinolone 1-ethyl-6-fluoro-1,4-dihydro-4-oxo-7-(1-piperazinyl)-3-quinoline carboxylic acid (prepared according to H. Koga, et. al., J. Med. Chem., 1980, 23, 1358)

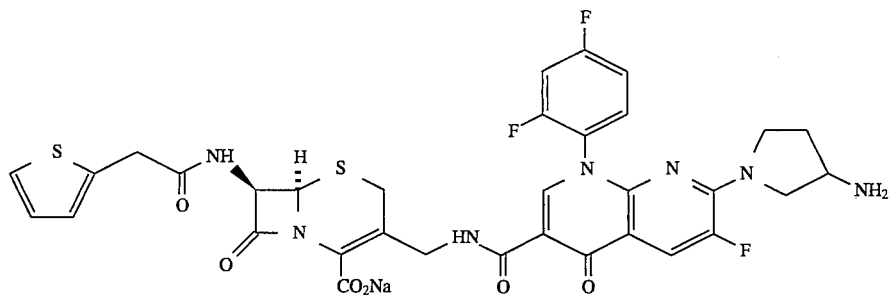

using the naphthyridinone 7-(3-aminopyrrolidinyl)-1-(2,4-difluorophenyl)-6-fluorol, 4-dihydro-4-oxo-1,8-naphthyridine-3-carboxylic acid (prepared according to D. T. W. Chu, et. al., J. Med. Chem., 1986, 29, 2363)

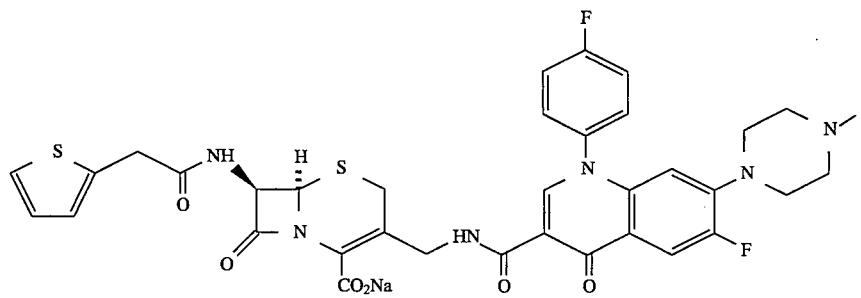

using the quinolone 6-fluoro-1-(4-fluorophenyl)-1,4-dihydro-4-oxo-7-(1-piperazinyl) 3-quinoline carboxylic acid (prepared according to D. T. W. Chu, et. al., J. Med. Chem., 1985, 28, 1558)

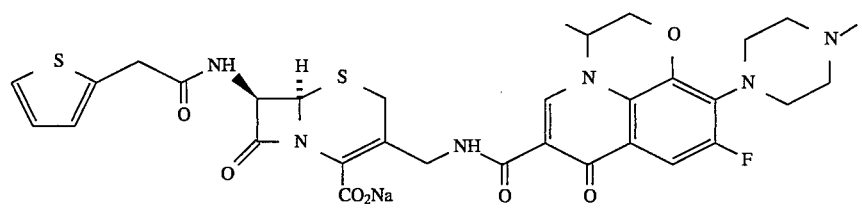

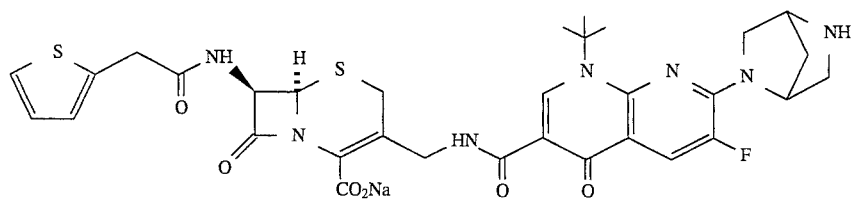

using the naphthyridinone 7-(2,5-diazabicyclo[2.2.1]heptan-2-yl)-1-(1,1-dimethylethyl) 6-fluoro-1,4-dihydro-4-oxo-1,8-naphthyridine-3-carboxylic acid (prepared according to A. Weber, et. al., EP 266576).

EXAMPLE 5

According to the general procedure of Example 4, the following quinolonyl lactam is made.

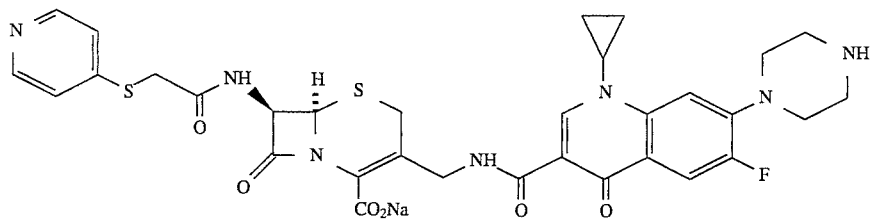

using the beta-lactam 3-(acetyloxymethyl)-8-oxo-7-[(4-pyridylthioacetyl)amino] 5-thia-1-azabicyclo[4.2.0]oct-2-ene-2-carboxylic acid (prepared according to S. Crast, et. al., J. Med. Chem., 1973, 16, 1413)

Similarly, the following quinolonyl lactam is prepared by the general procedure of this Example, with substantially similar results.

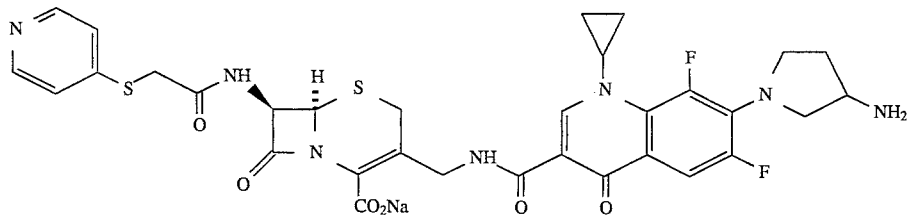

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983 ).

EXAMPLE 6

According to the general procedure of Example 4, the following quinolonyl lactam is made.

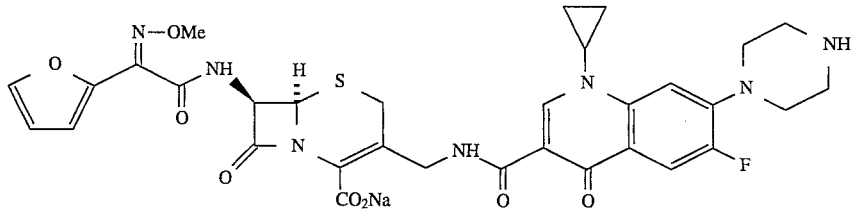

using the beta-lactam 3-[[(aminocarbonyl)oxy]methyl]-7-[[2-furanylmethoxyimino)acetyl] amino]-8-oxo-5-thia-1-azabicyclo [4.2.0]oct-2-ene-carboxylic acid (prepared according to M. C. Cook, et. al., U.S. Pat. No. 3,974,153).

Similarly, the following quinolonyl lactam is prepared by the general procedure of this Example, with substantially similar results.

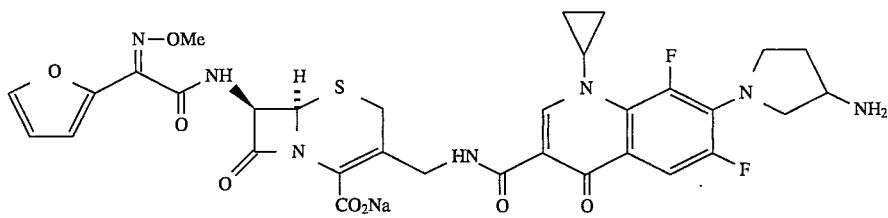

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983).

EXAMPLE 7

According to the general procedure of Example 4, the following quinolonyl lactam is made.

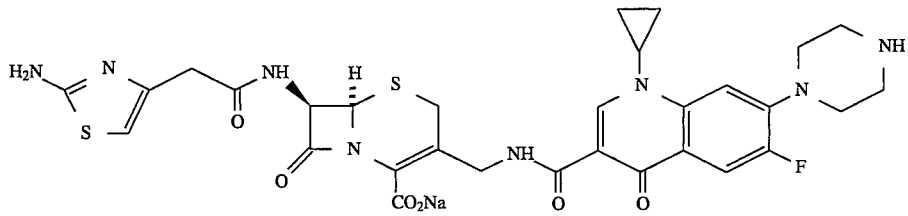

using the beta-lactam 3-(acetyloxymethyl)-7-[[(2-amino-4-thiazolyl)acetyl] amino]-8-oxo-5-thia-1-azabicyclo [4.2.0]oct-2-ene-2-carboxylic acid (prepared according to J. Org. Chem., 1970, 35, 2430).

Similarly, the following quinolonyl lactam is prepared by the general procedure of this Example, with substantially similar results.

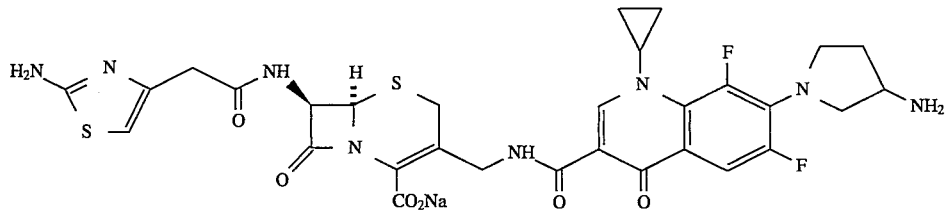

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983).

EXAMPLE 8

According to the general procedure of Example 4, the following quinolonyl lactam is made.

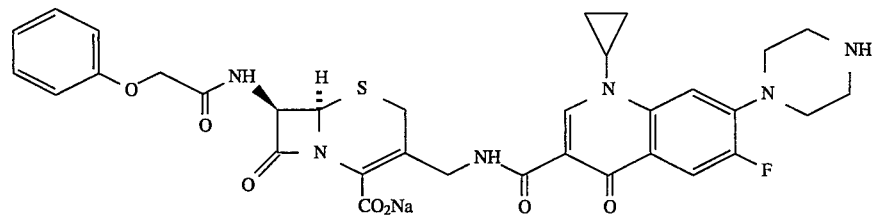

using the beta-lactam 3-(acetyloxymethyl)-8-oxo-7-[(phenoxyacetyl)amino] 5-thia-1-azabicyclo[4.2.0]oct-2-ene-2-carboxylic acid (prepared according to R. B. Morin, et. al., J. Am. Chem. Soc., 1969, 91, 1401).

Similarly, the following quinolonyl lactam is prepared by the general procedure of this Example, with substantially similar results.

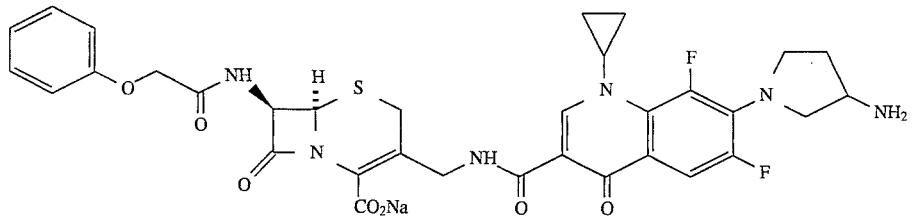

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983).

EXAMPLE 9

According to the general procedure of Example 4, the following quinolonyl lactam is made.

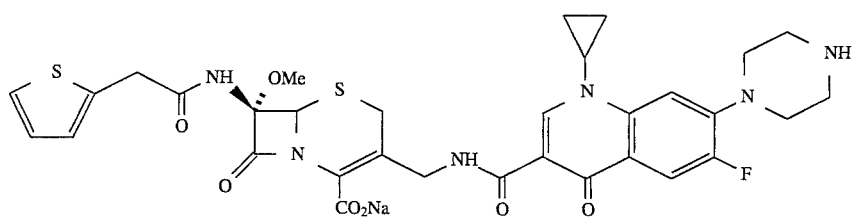

using the beta-lactam 3-(acetyloxymethyl)-7-methoxy-8-oxo-7-[(2-thienylacetyl)amino] 5-thia-1-azabicyclo[4.2.0] oct-2-ene-2-carboxylic acid (prepared according to Karady, et al., J. Am. Chem. Soc., 1972, 94, 1410).

Similarly, the following quinolonyl lactam is prepared by the general procedure of this Example, with substantially similar results.

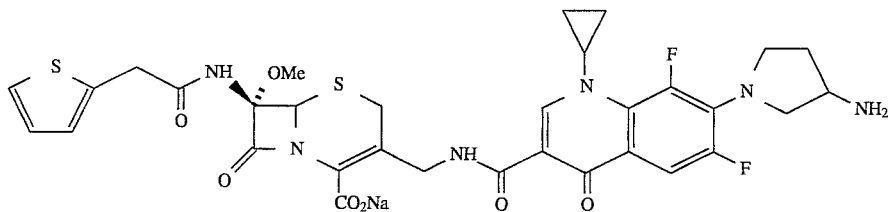

using the quinolone 7-(3-aminopyrrolidinyl)-1-cyclopropyl-6,8-difluoro-1,4-dihydro-4oxo 3-quinoline carboxylic acid (prepared according to J. P. Sanchez, et. al., J. Med. Chem., 1988, 31, 983).

EXAMPLE 10

According to the general procedure of Example 5, the following quinolonly lactam is made.

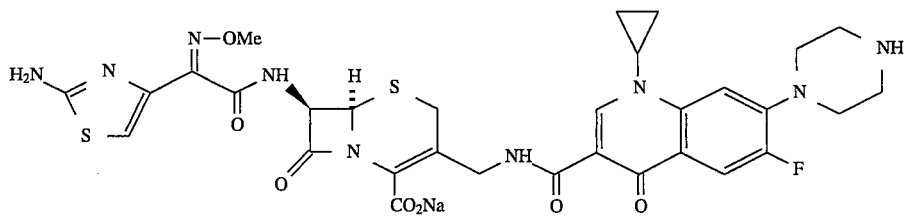

using the beta-lactam 3-[(acetyloxy)methyl]-7-[(2-amino-4-thiazolyl)methoxyimino)acetyl] amino]-8-oxo-5-thia-1-azabicyclo [4.2.0]oct-2-ene-carboxylic acid (prepared according to M. Ochiai, et al., U.S. Pat. No. 4,098,888)).

Similarly, the following quinolonyl lactams are prepared by the general procedure of this Example, with substantially similar results.

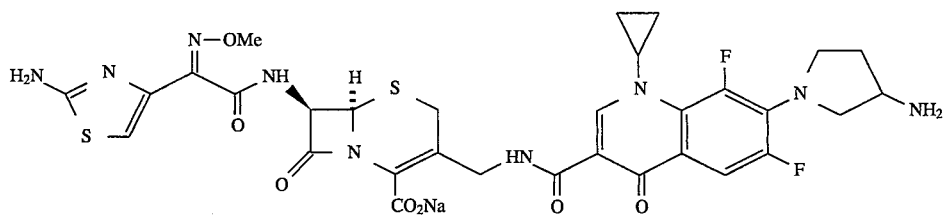

using the quinolone 7-(3-aminopyrrolidinyl)-1-cyclopropyl-6,8-difluoro-1,4-dihydro-4oxo 3-quinoline carboxylic acid (prepared according to J. P. Sanchez, et. al., J. Med. Chem., 1988, 31, 983)

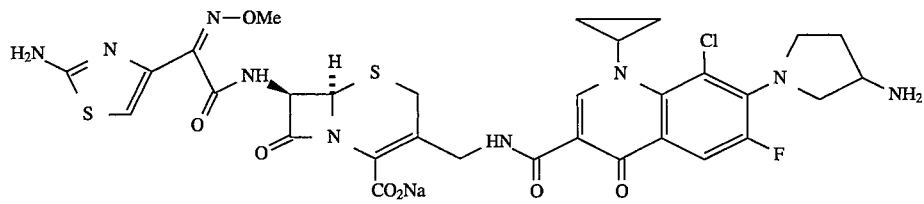

using the quinolone 7-(3-aminopyrrolidinyl)-1-chloro-1-cyclopropyl-6-fluoro-1,4-dihydro-4-oxo 3-quinoline carboxylic acid (prepared according to J. P. Sanchez, et. al., J. Med. Chem., 1988, 31, 983)

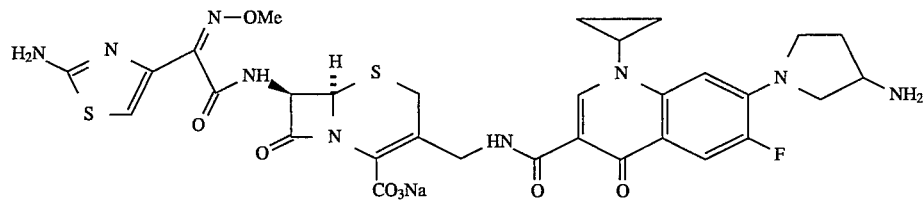

using the quinolone 7-(3-aminopyrrolidinyl-1-cyclopropyl-6-fluoro-1,4-dihydro-4-oxo 3-quinoline carboxylic acid (prepared according to J. P. Sanchez, et. al., J. Med. Chem., 1988, 31, 983)

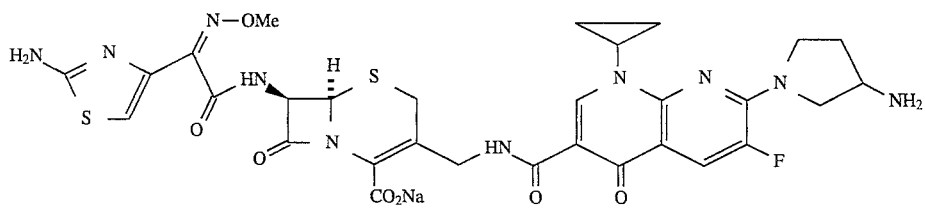

using the naphthyridinone 7-(3-aminopyrrolidinyl)-1-cyclopropyl-6-fluoro-1,4-dihydro-4-oxo 1,8-naphthyridine-3-carboxylic acid (prepared according to J. P. Sanchez, et. al., J. Med. Chem., 88, 31,983)

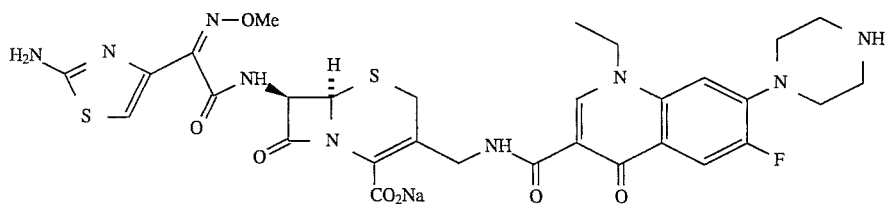

using the quinolone 1-ethyl-6-fluoro-1,4-dihydro-4-oxo-7-(1-piperazinyl)-3-quinoline carboxylic acid (prepared according to H. Koga, et. al., J. Med. Chem., 1980, 23, 1358)

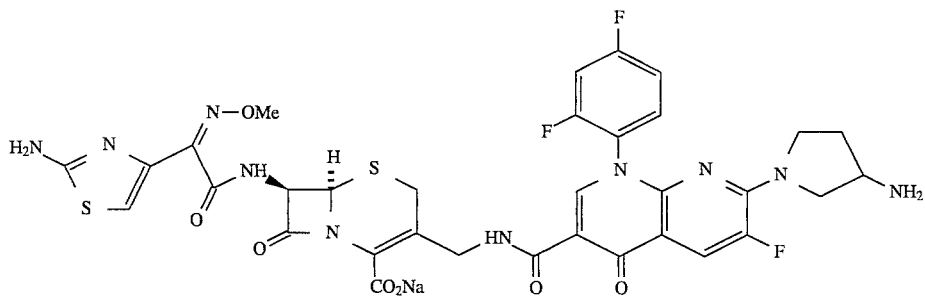

using the naphthyridinone 7-(3-aminopyrrolidinyl)-1-(2,4-difluorophenyl)-6-fluorol, 4-dihydro-4-oxo-1,8-naphthyridine-3-carboxylic acid (prepared according to D. T. W. Chu, et. al., J. Med. Chem., 1986, 29, 2363).

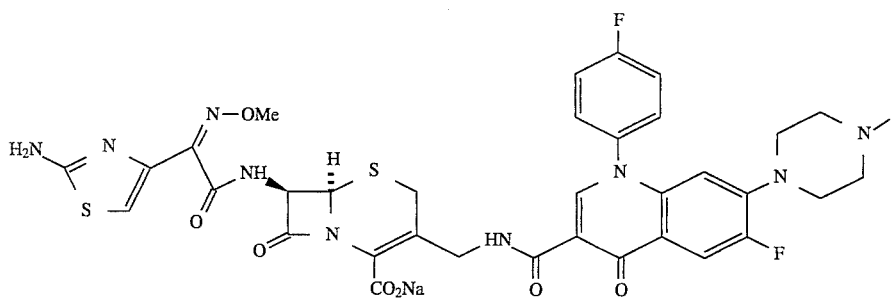

using the quinolone 6-fluoro-1-(4-fluorophenyl )-1,4-dihydro-4-oxo-7-(1-piperazinyl) 3-quinoline carboxylic acid (prepared according to D. T. W. Chu, et. al., J. Med. Chem., 1985, 28, 1558)

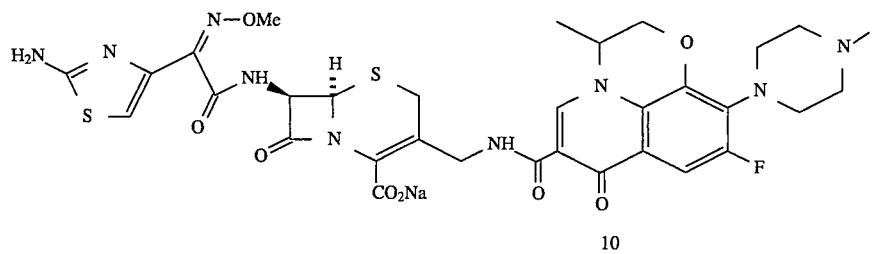

using the quinolone 9-fluoro-4,7-dihydro-3-methyl-10-(1-piperazinyl)-7-oxo-2H-pyrido [1,2,3-de]-1,4-benzoxazine-6-carboxylic acid (prepared according to I. Hayakawa, et. al., Chem. Pharm. Bull., 1984, 32, 4907)

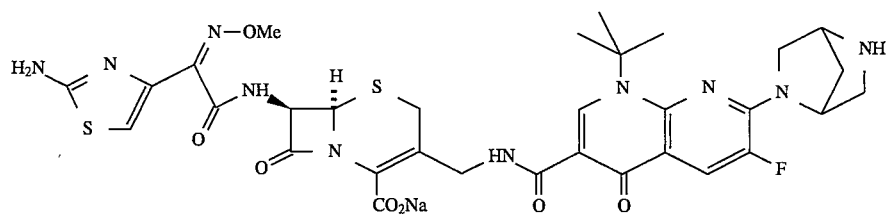

using the naphthyridinone 7-(2,5-diazabicyclo[2.2.1]heptan-2-yl)-1-(1,1-dimethylethyl) 6-fluoro-1,4-dihydro-4-oxo-1,8-naphthyridine-3-carboxylic acid (prepared according to A. Weber, et. al., EP 266576)

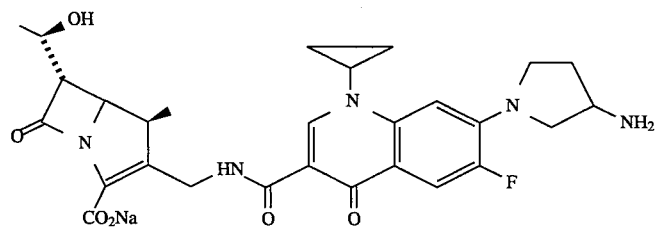

using the quinolone 7-(3-aminopyrrolidinyl-1-cyclopropyl-6-fluoro-1,4-dihydro-4-oxo 3-quinoline carboxylic acid prepared according to J. P. Sanchez, et. al., J. Med. Chem., 1988, 31, 983 ).

The following other quinolonyl lactams are also prepared by the general procedure of this Example and Examples 1–9, with substantially similar results.

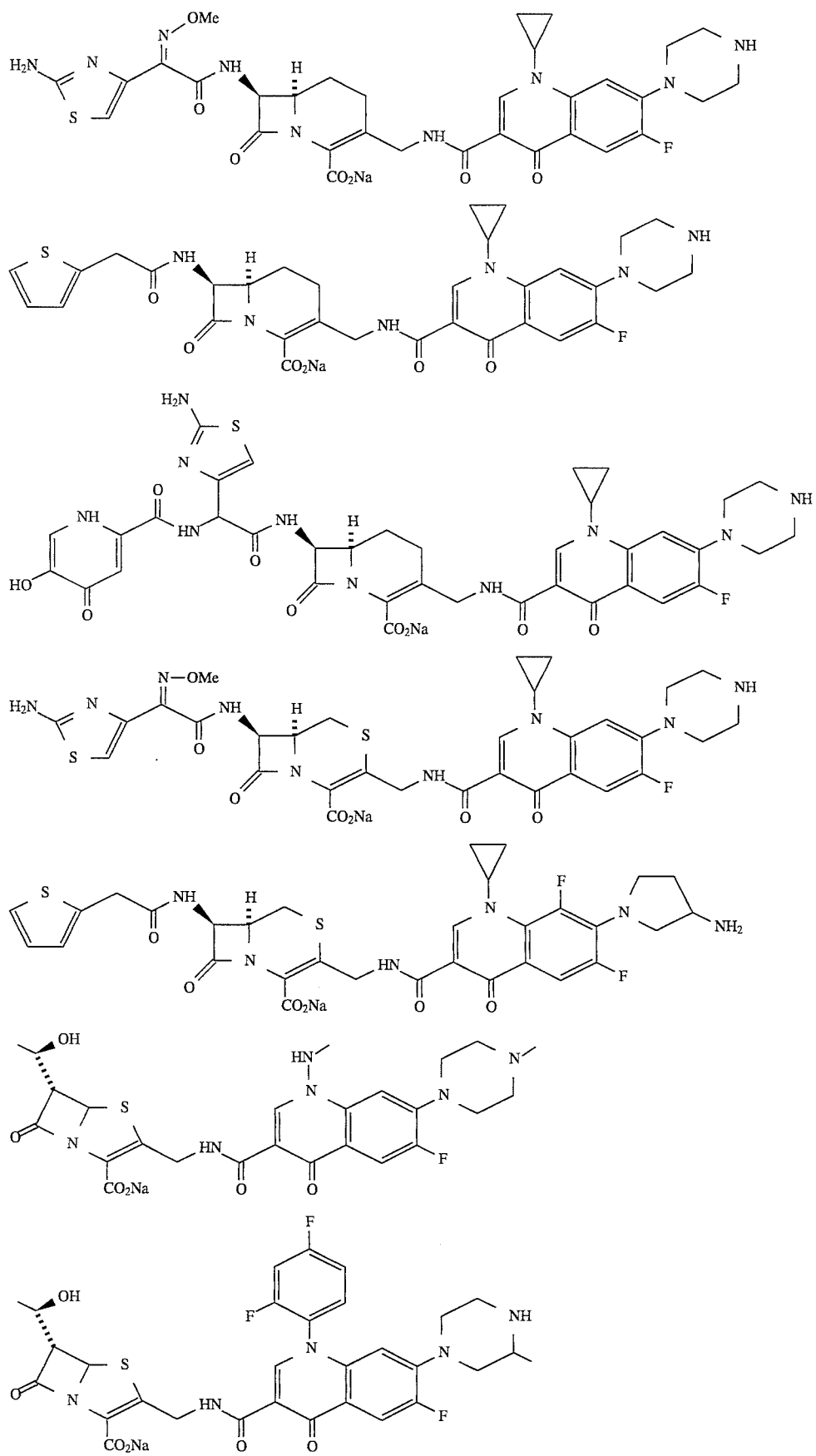

-continued
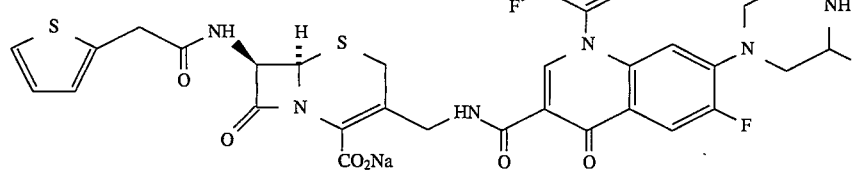
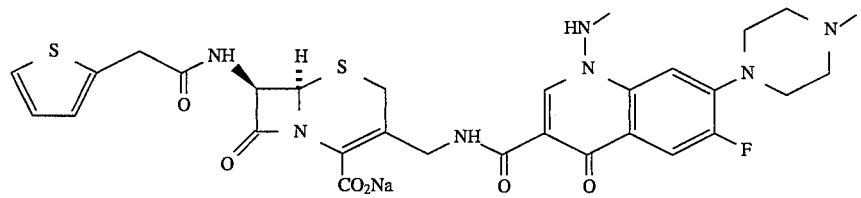
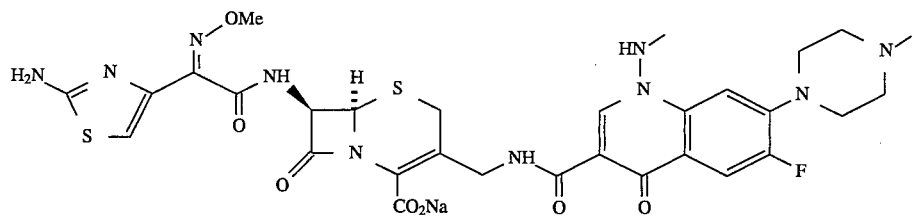
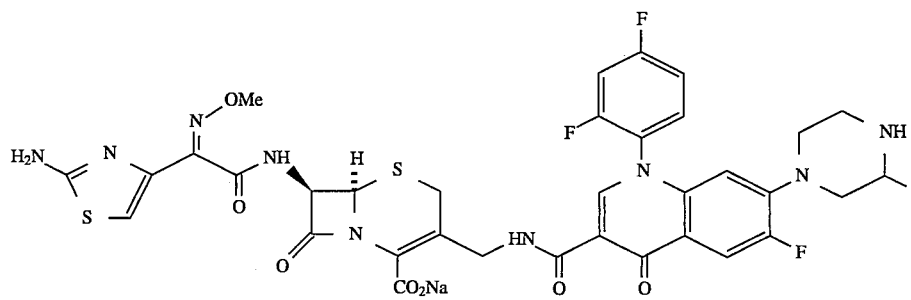
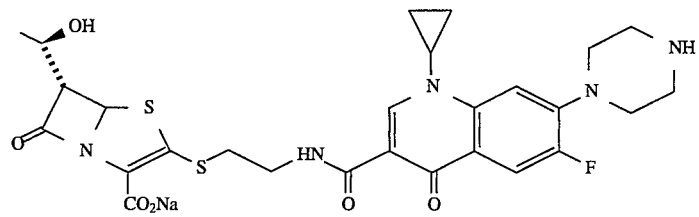
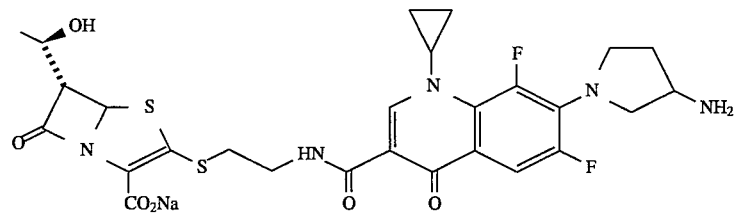
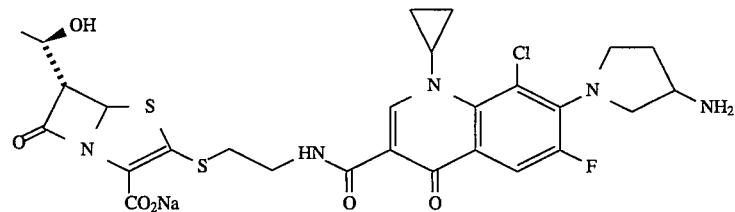

-continued
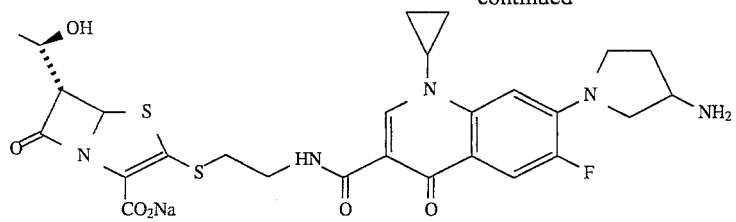
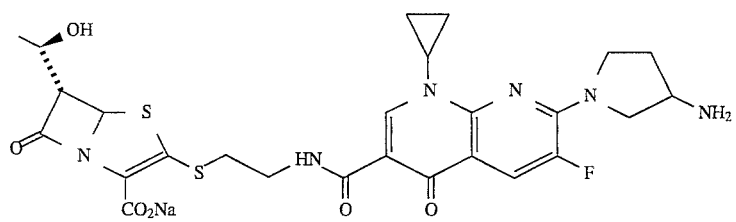
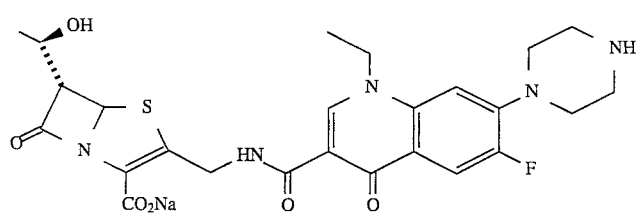
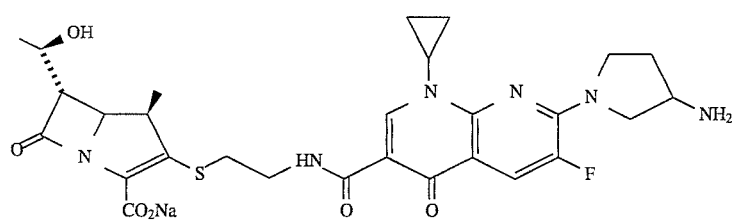
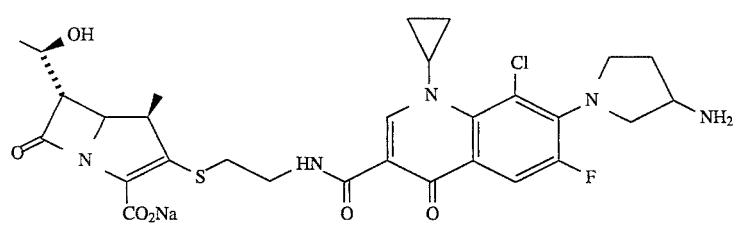
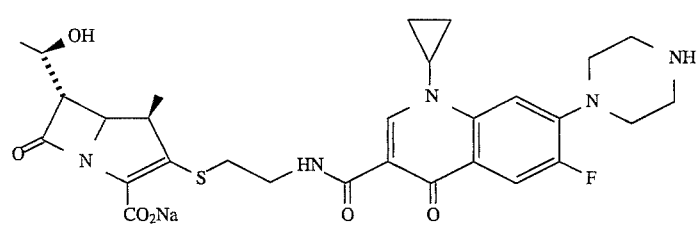
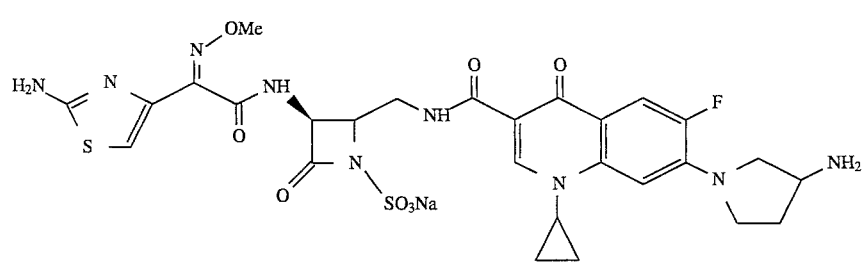

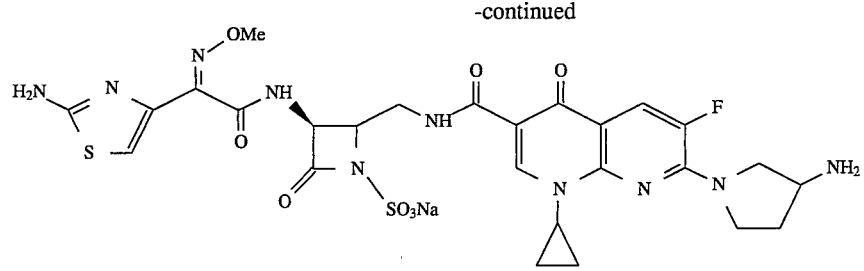
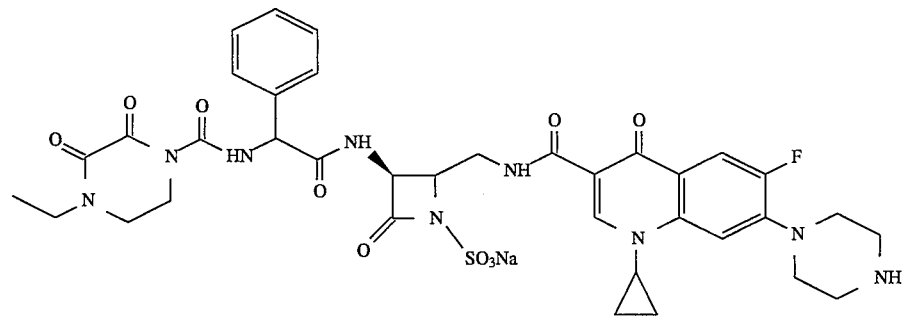
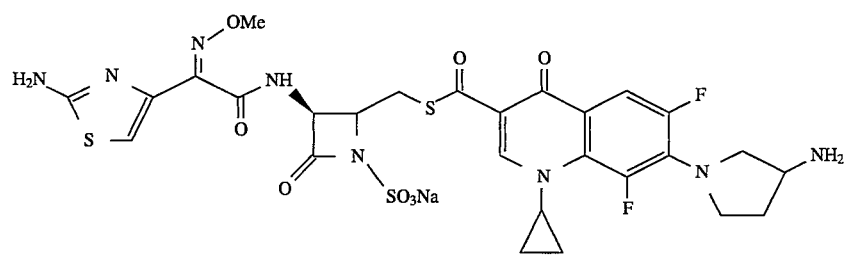
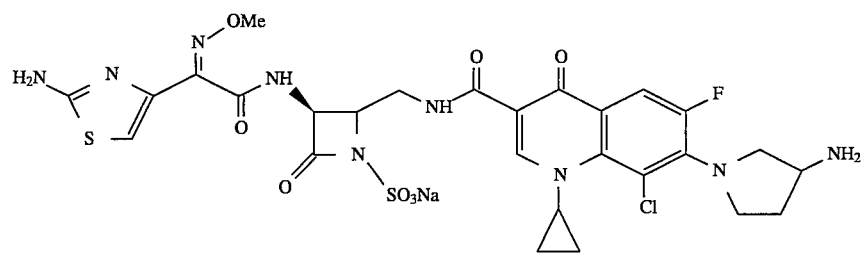
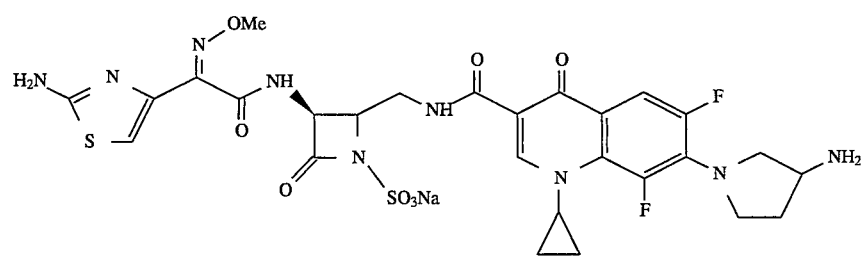
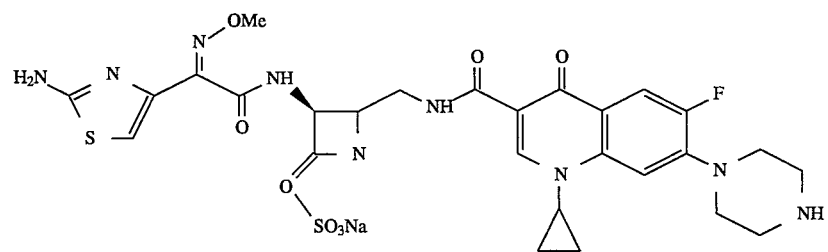

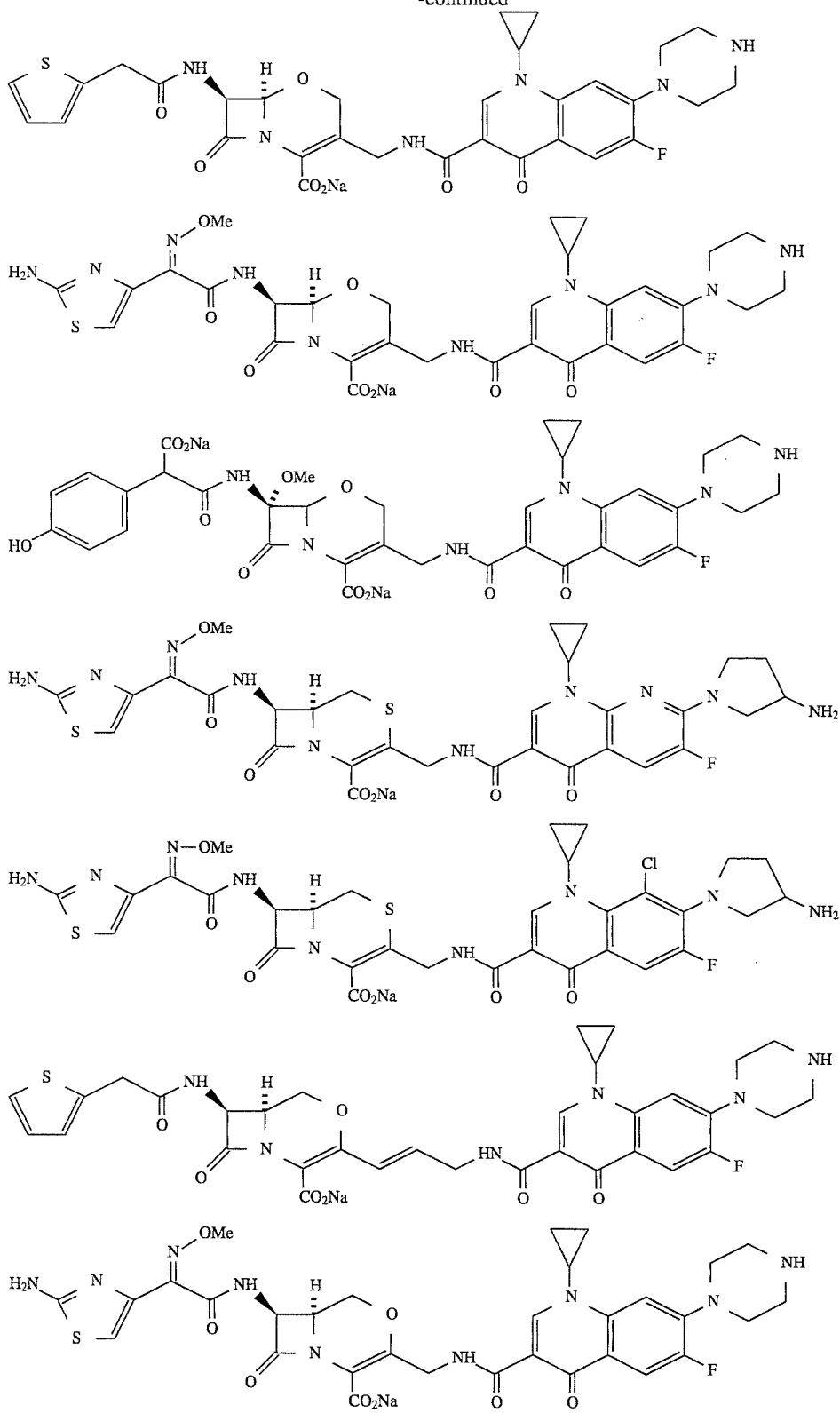
EXAMPLE 11
[6R-6a,7B]]-3-[[1-Cyclopropyl-6-fluoro-1,4-dihydro-4-oxo-7 (1-piperazinyl)-3-quinolinylcarbonyl]hydrazinomethyl]-8-oxo-7-[ (2-thienylacetyl)amino]-5-thia-1-azabicyclo[4.2.0]oct-2-ene-2-carboxylic acid sodium salt, according to this invention, is made by the following general reaction sequence.

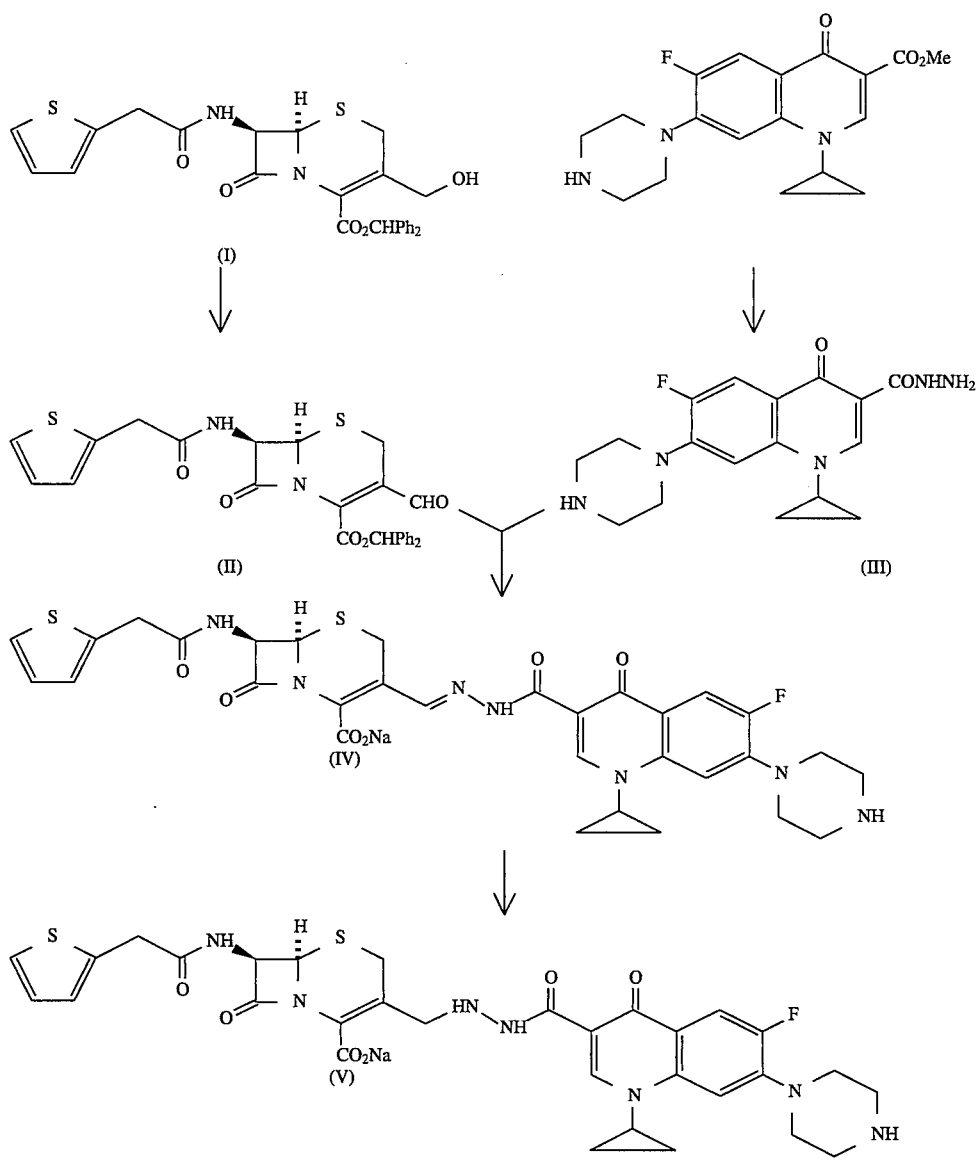

A solution of 3-(hydroxymethyl)-8-oxo-7-[(2-thienylacetyl)amino]-5-thia-1-azabicyclo [4.2.0]oct-2-ene-2-carboxylic acid diphenylmethyl ester (I) (0.65 g) in dichloromethane (20 ml) is added to a mixture of Dess-Martin periodinane (0.59 g) in dichloromethane (10 ml). The reaction is stirred for 30 minutes and poured into a mixture of ether (30 ml) and 10% aqueous sodium bicarbonate (50 ml) containing a 7-fold excess of sodium thiosulfate. The mixture is rapidly stirred for 12 minutes and the organic layer separated and washed with 10% sodium bicarbonate and water. The organic phase is dried over sodium sulfate, filtered and the filtrate is concentrated to dryness to yield product (II).

Separately, a solution of ciprofloxacin methyl ester (1.0 g), hydrazine hydrate (1.45 g) and DMF (dimethylformamide) (50 ml) is heated at 40° C. (105° F.) for 16 hours and concentrated to dryness in vacuo. The residue is triturated with acetone and recrystallized from ethanol/DMF to give the hydrazide product (III).

Approximately 0.50 g of product (II) and approximately 0.33 g of product (III) are mixed in DMF (25 ml) stirred at room temperature for 6 hours and concentrated to dryness in vacuo. The hydrazone is purified by repeated trituration in acetone, and then dissolved in anisole (5 ml). To this solution is added dropwise trifluoroacetic acid at −15° C. (5° F.) and the reaction is stirred at ambient temperature for 20 minutes. The solution is concentrated to dryness in vacuo and the residue is triturated with ether. The solid is dissolved in DMF/H$_2$O and treated with sodium bicarbonate (0.080 g); then the solution is concentrated to dryness in vacuo and the solid recrystallized from ethanol/water to give product (IV).

Approximately 0.18 g of product IV is then mixed with 10% Pd/C (0.18 g) and 70% THF/H$_2$O and subjected to hydrogenation for 16 hours, and filtered to remove the catalyst. The filtrate is concentrated to dryness and the final Product (V) is purified by recrystallization from ethanol/water.

EXAMPLE 12

(3S)-1-[[7-(3-Amino-1-pyrrolidinyl)-1-cyclopropyl-6,8-difluoro-1, 4-dihydro-4-oxo-3-quinolinyl[carbobylthio]-4-oxo-3-[(phenoxyacetyl) amino]-1-azetidinesulfonic acid sodium salt, according to this invention, is made by the following general reaction sequence.

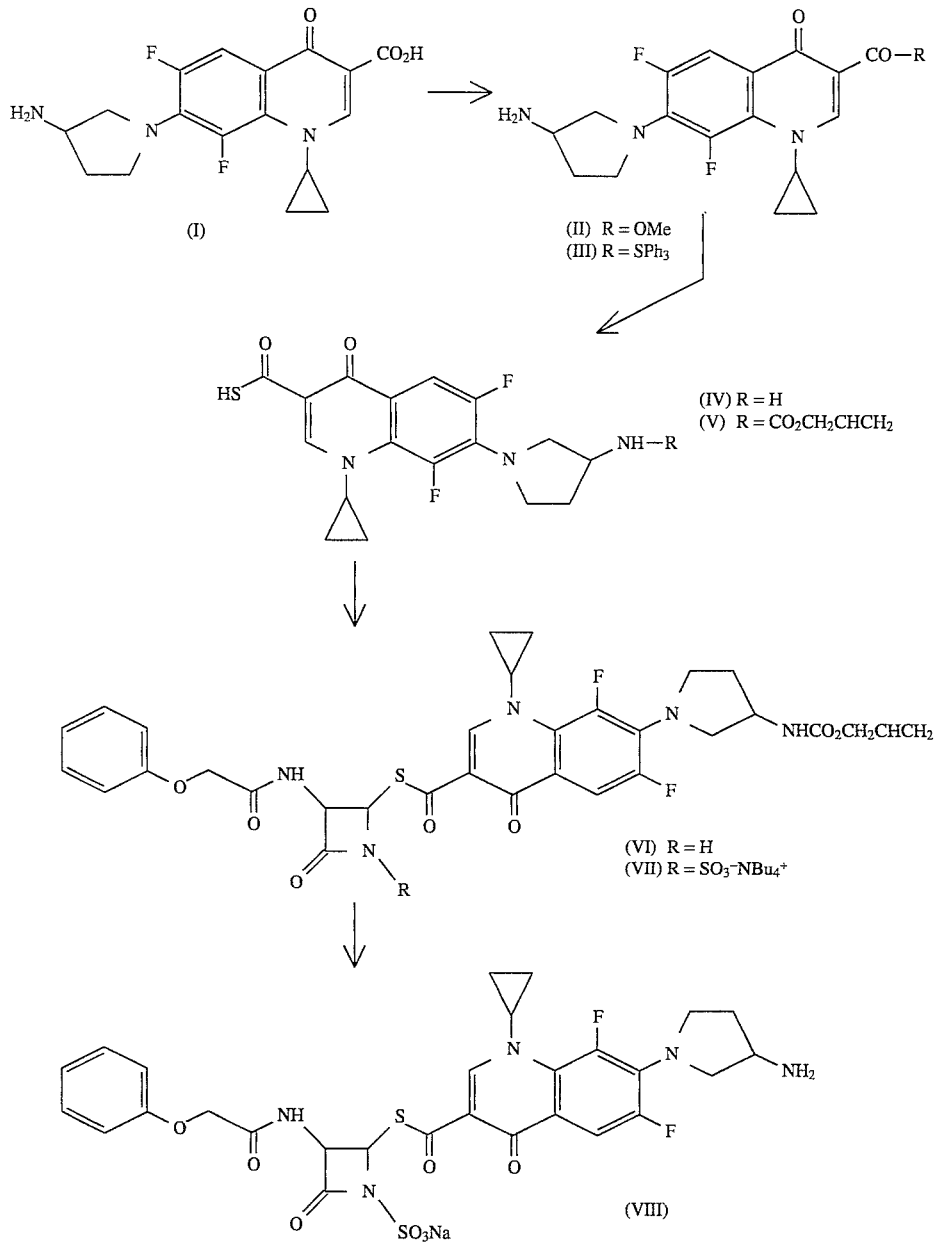

Approximately 1.9 g of 7-[3-amino-1-pyrrolidinyl]-1-cyclopropyl-6,8-difluoro-1,4-dihydro 4-oxo-3-quinoline carboxylic acid (I) is dissolved in approximately 54 ml of absolute methanol. Approximately 7.9 ml of thionyl chloride is added at approximately 6° C. (43° F.). The mixture is refluxed for approximately 15 hr and then concentrated to dryness. Cold sodium carbonate solution is added and the solution is is extracted with dichloromethane. The organic layer is dried and concentrated to yield product (II).

Approximately 0.02 g of 60% NaH (dispersion in mineral oil) is added to a solution of 0.78 g of triphenylmethyl mercaptan in approximately 20 ml of THF. Approximately 1.15 g of 4 Angstrom molecular sieves and 0.21 g of product (II) are then added. The mixture is stirred at room temperature for approximately 2.5 days, cooled, and approximately 0.1 ml of water is added, and the mixture filtered. The filtrate is concentrated to dryness and taken up in dichloromethane and washed with 1N aqueous NaOH, then with water. The organic phase was concentrated to dryness and the residue recrystallized from ethyl acetate to yield product (III).

A solution of 0.3 g of product (III) in 12 ml of glacial acetic acid is treated with 4 ml of 1 N HCl solution. The solution is heated for approximately 1.5 hr and then the acid is evaporated. The residue is triturated with acetone and the product filtered to yield product (IV).

A mixture of 0.8 g of product (IV) and approximately 23 ml of water is cooled to 0° C. (32° F.), and a 1 N NaOH solution is added dropwise to pH of 12. Approximately 6 ml of acetone is added followed by a dropwise addition of 0.35 g of allyl chloroformate in approximately 4 ml of acetone, maintaining a temperature of 0° C. and pH 12 using additional 1N sodium hydroxide. Stirring is continued for approximately 60 min or until the pH drift ceases to change from pH 12. The acetone is removed by evaporation in vacuo and the aqueous layer is extracted with ether. The aqueous layer is cooled and 10% HCl solution is added to adjust the pH to 2. This is extracted with dichloromethane, the organic layer washed with water, dried and concentrated and triturated with ether to yield product (V).

A solution of 1.2 g of product (V) in a mixture of 10 ml dioxane and 2.77 ml of 1 N sodium hydroxide solution, is stirred for approximately 20 min in an ice bath. Then 0.6 g of 4-(acetyloxy)-3-[(phenoxyacetyl)amino]-2-azetidinone, in approximately 10 ml of dioxane, is added slowly. The reaction is stirred in an ice bath then warmed to room temperature to complete the reaction. Product (VI) is isolated by filtration.

A solution of 0.25 g of product (VI) in 1 ml of DMF is made, and 0.5 g of DMF·SO₃ complex is added. The reaction mixture is stirred for approximately 2 hours after which the mixture is diluted with 10 ml of dichloromethane and 10 ml of 0.5 N potassium hydrogen phosphate solution. The pH is adjusted to 6 and 0.13 g of tetrabutylammoniumhydrogen sulfate is added. The layers are separated and the organic layer is washed with water, dried and concentrated to yield product (VII).

Approximately 0.59 g of product (VII) is taken up in approximately 10 ml of dichloromethane, 60 ml of water and 9 mg of bis(triphenylphosphine)palladium chloride. The mixture is treated with approximately 300 microliters of tributyltinhydride while maintaining a temperature of approximately 21° C. (70° F.). After rapid stirring for approximately 15 minutes, the reaction is concentrated to dryness, triturated with diethylether, and the crude product is taken up in aqueous methanol and stirred with Dowex 50W (Na) for approximately ] hour. The resin is filtered off and washed with water. The filtrate is concentrated and lyophilized to yield the product (VIII) as a powder. Final purification is achieved by trituration in dichloromethane.

Similarly, the following quinolonyl lactam is prepared by the general procedure of this Example, with substantially similar results.

EXAMPLE 13

[6R-[6α,7β]]-3-[[1-cyclopropyl-6-fluoro-1,4-dihydro-4-oxo 7-(1-piperazinyul)-3-quinolinyl]carbonylthio]methyl]-8-oxo 7-[(2-thienylacetyl)amino]-5-thia-1-azabicyclo[4.2.0] oct-2-ene-2-carboxylic Acid Sodium Salt

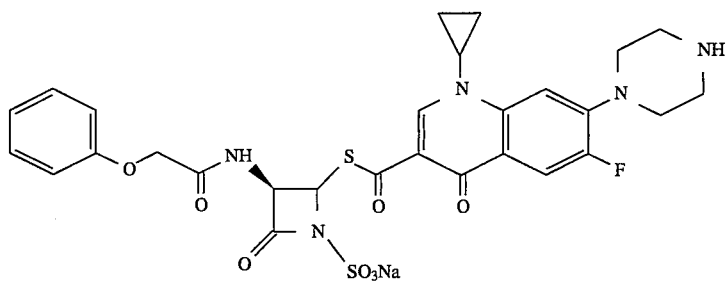

using the quinolone 1-cyclopropyl-6-fluoro-1,4-dihydro-4-oxo-7-(1-piperazinyl) 3-quinoline carboxylic acid (prepared according to K. Grohe, et al., Get. Offen. DE 3142854).

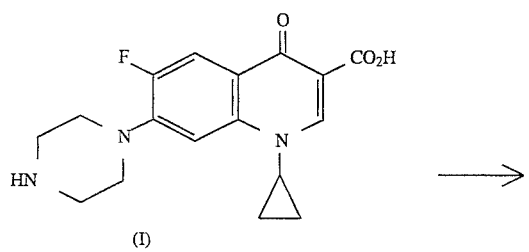
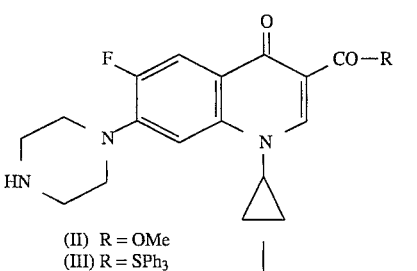

(I)   (II) R = OMe
      (III) R = SPh₃

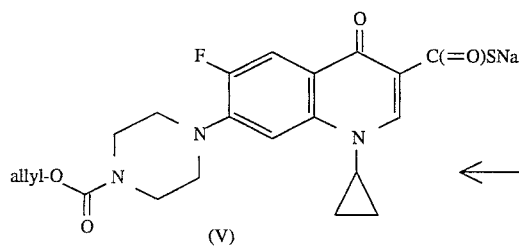
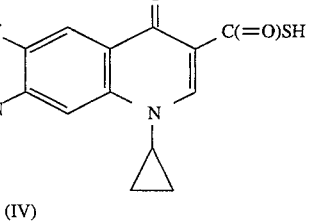

(V)   (IV)

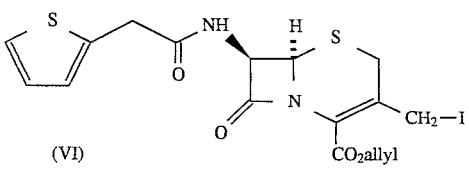

(VI)

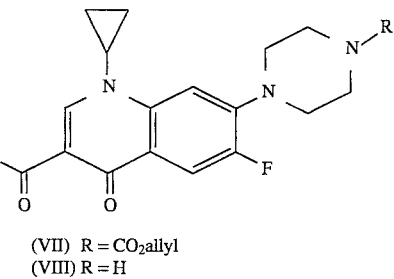

(VII) R = CO₂allyl
(VIII) R = H

To approximately 3.3 gm of 1-cyclopropyl-6-fluoro-1,4-dihydro-4-oxo-7-(1-piperazinyl) 3-quinoline-3-carboxylic acid (I, prepared according to K. Grohe, et al., Ger. Offen. DE 3142854) in 100 ml absolute methanol is added 14 ml of thionyl chloride. The reaction was refluxed for approximately 15 hours and then concentrated to dryness. The crude residue is then extracted with methylene chloride and aqueous sodium carbonate solution. The organic layer is dried over Na₂SO₄ and concentrated to yield product (II).

To approximately 2.5 gm of triphenylmethyl mercaptan in 75 ml of DMF is added 0.1 gm of NaH (60% in mineral oil). After 15 minutes, approximately 15 gm of 4 angstrom molecular sieves and 2.9 gm product (I) is added at room temperature. The mixture is then heated at 40°–45° C. for 18 hours. The reaction is cooled, 2 ml of water is added and then the mixture is filtered. The DMF is removed under vacuum and the crude residue is taken up in methylene chloride and extracted several times with 1N aqueous NaOH solution. The organic layer is washed with brine solution, dried over sodium sulfate and concentrated to dryness. The crude product (III) is used as is for the next step.

To a solution of approximately 3.7 gm of product (III) in 50 ml galcial acetic acid is added 10 ml of 3N HCl solution and the mixture is heated at 60° C. for approximately 4 hours. The solution is concentrated to dryness and the crude residue is triturated with acetone to yield product (IV) after filtration.

To a solution of 1.9 gm of product (IV) in 75 ml of water at approximately 5° C. is added 1N NaOH to adjust the pH to 12. Then approximately 12 ml of acetone is added followed by the dropwise addition of 0.9 gm allyl chloroformate in 10 ml acetone. During the addition, the pH is maintained around 12 with the periodic addition of further 1N NaOH and the reaction is maintained at approximately 5° C. After 30 minutes an additional 0.5 gm aliquot of allyl chloroformate in 5 ml acetone is added. The reaction is allowed to warm to room temperature over 3 hours and then the acetone is removed by evaporation. The remaining solution is then extracted with methylene chloride, the aqueous layer is acidified and then extracted 2× with methylene chloride. The organic layer is then dried with sodium sulfate, concentrated to dryness, and triturated with acetone/hexanes to give approximately 2 gm of solid. This product is then dissolved in methylene chloride and chilled to approximately 5° C., and a solution of 185 mg of sodium hydroxide in 0.5 ml methanol is added dropwise. After 1 hour the reaction mixture is evaporated to dryness and the residue is triturated with acetone to yield product (V).

Separately, reactant (VI) is prepared by suspending approximately 25 gm of commercial cephalothin sodium salt in 500 ml of 50% DMF/dioxane, which is cooled to 3°–5° C. Allyl iodide (12.1 gm) is added and the reaction is stirred in the dark at room temperature for approximately 46 hours. The reaction mixture is poured into brine solution and ethyl acetate and extracted. The aqueous layer was extracted with a second ethyl acetate wash, the organic layers were combined and then washed successively with brine, water, 10% sodium bicarbonate and water. The solution is then dried over sodium sulfate, filtered and evaporated to dryness. The residue is triturated with either to obtain a solid product.

To approximately 10 gm of this intermediate in methylene chloride is added 8.4 ml trimethylsilyl iodide. The reaction is stirred at room temperature in the dark for 2 hours, then cooled to approximately 5° C. and slowly quenched with cold 10% aqueous sodium thiosulfate. The resulting layers are separated and the organic phase is washed with additional thiosulfate solution, then water, dried over sodium sulfate and filtered. The solution is then evaporated to near Similarly, the following quinolonyl lactams are prepared by the general procedure of this Example, with substantially similar results.

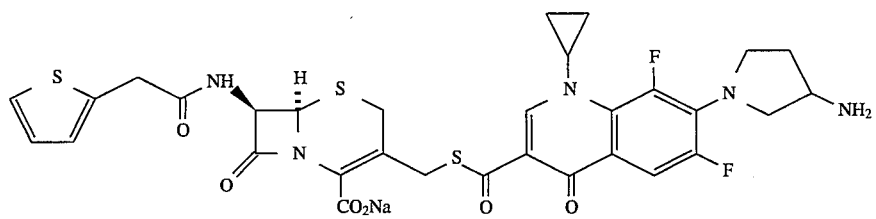

dryness and the residue is treated with hexanes to precipitate reactant (VI).

Approximately 2.0 gm of product (V) is added portionwise over 5 minutes to a solution of 2.2 gm reactant (VI) in 40 ml 50% DMF/dioxane at room temperature in the dark. The reaction is allowed to proceed for 2 hours and then evaporated to dryness. The residue is then taken up in water and ethyl acetate, the organic layer collected and washed 5× with cold 0.14N aqueous sodium hydroxide, then with water. The solution is dried over sodium sulfate, filtered and evaporated. The residue is triturated with acetone/hexanes to obtain solid product (VII).

Approximately 1.3 gm of product (VII) is dissolved in 30 ml methylene chloride containing approximately 0.15 ml water and 20 mg bis(triphenylphosphine) palladium chloride. Approximately 0.9 ml of tributyltin hydride is added dropwise over 1 minute while maintaining the reaction at approximately 20° C. The reaction is vigorously stirred for 10 minutes during which time a precipitate forms which is collected by filtration and dried. The precipitate is then suspended in water containing 1 equivalent sodium bicarusing the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983)

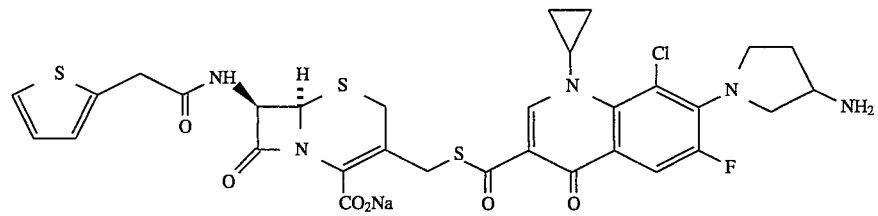

bonate. Acetone is then added slowly causing a complete solution to initially form, followed by the precipitation of the product (VIII) which is collected by filtration.

using the quinolone 7-(3-aminopyrrolidinyl)-1-chloro-1-cyclopropyl-6-fluoro-1,4-dihydro-4-oxo 3-quinoline carboxylic acid (prepared according to J. P. Sanchez, et. al., J. Med. Chem., 1988, 31, 983)

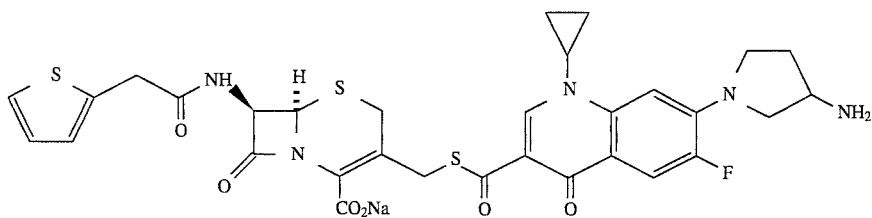

using the quinolone 7-(3-aminopyrrolidinyl-1-cyclopropyl-6-fluoro-1,4-dihydro-4-oxo 3-quinoline carboxylic acid (prepared according to J. P. Sanchez, et. al., J. Med. Chem., 1988, 31, 983)

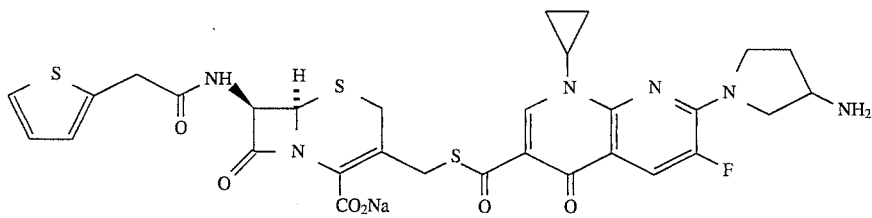

using the naphthyridinone 7-(3-aminopyrrolidinyl )-1-cyclopropyl-6-fluoro-1,4-dihydro-4oxo 1,8-naphthyridine-3-carboxylic acid (prepared according to J. P. Sanchez, et. al., J. Med. Chem., 1988, 31, 983).

EXAMPLE 14

[5R-[5α,6α]]-2-[[2-[1-cyclopropyl-6-fluoro-1,4-dihydro-4-oxo 7-(1-piperazinyl)-3-quinolinyl]carbonylthio]ethylthio]-6-(1-hydroxyethyl)-3methyl-7-oxo 1-azabicyclo[3.2.0]hept-2-ene-2-carboxylic Acid Sodium Salt

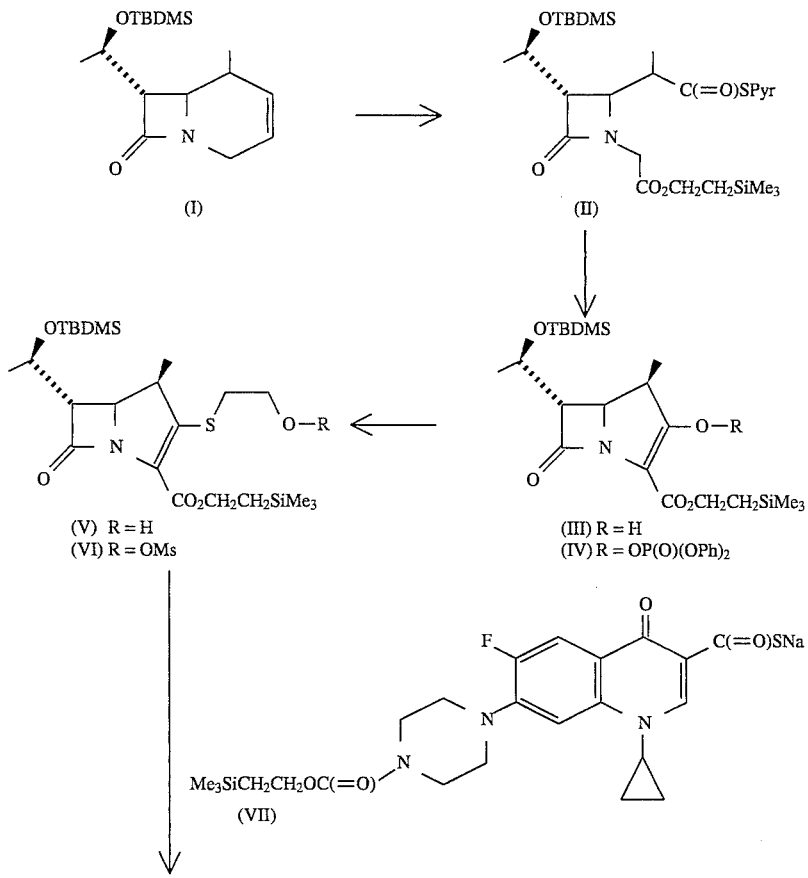

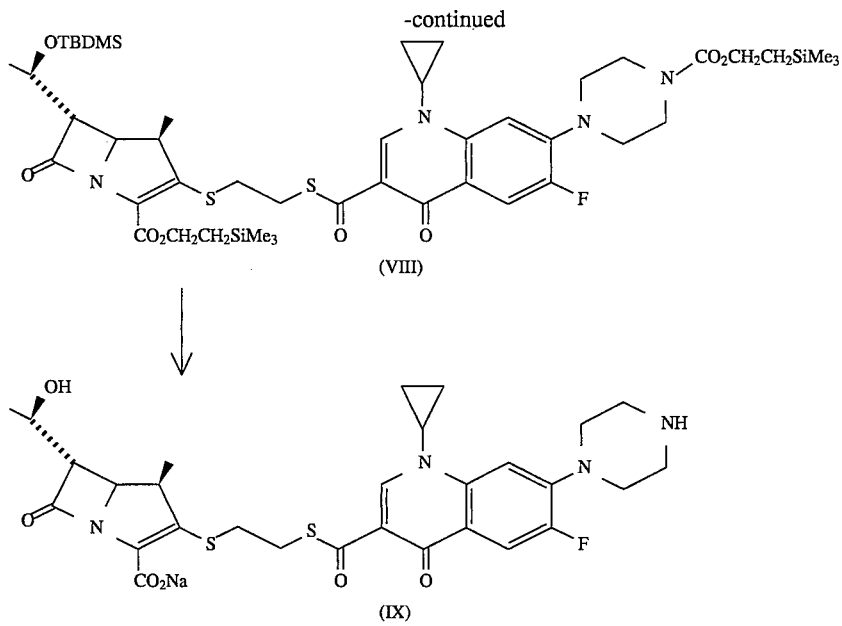

Approximately 7.2 g of 2-(t-butyldimethylsilyloxy)-1-methylcarbaceph-2-em (prepared according to 53 J. Org. Chem., 4154 (1988)), 1.6 g NaHCO₃, 36 ml of 2-(trimethylsilyl)ethanol, and 1 ml of a 0.1% solution of Sudan III in CH₂Cl₂ are combined in approximately 300 ml of CH₂Cl₂. A stream of argon is bubbled through the solution while cooling to approximately −78° C. Ozone is bubbled through the solution until the red color disappears, then argon is bubbled through the solution as it is allowed to warm to room temperature. Approximately 7.1 ml of triethylamine and 9.6 ml of acetic anhydride are added to the solution and it is allowed to stir for approximately 16 hours at room temperature. The mixture is diluted with approximately 400 ml of saturated aqueous ammonium chloride and the aqueous phase is extracted twice with approximately 400 ml of ether. The combined organic layers are washed with approximately 400 ml of saturated aqueous sodium chloride then dried over MgSO₄. After filtration and concentration most of the 2-(trimethylsilyl)ethanol is removed by short path distillation at approximately 60° C./0.1 mmHg. The resulting residue is dissolved in approximately 600 ml of CH₂Cl₂ under an argon atmosphere and approximately 8.2 g of 2,2'-dipyridyl disulfide and 9.8 g of triphenylphosphine are added. After approximately 5 hours at room temperature the solution is concentrated and purified by chromatography on silica gel to give the product II as a mixture of isomers at the position alpha to the thioester carbonyl.

A solution containing approximately 3.0 g of product II in approximately 120 ml of tetrahydrofuran is cooled to approximately −75° C. under an argon atmosphere. Approximately 10.0 ml of a 1.0 M solution of sodium bis(trimethylsilyl)amide in tetrahydrofuran is added dropwise over approximately 7 minutes while maintaining the reaction temperature below approximately −70° C. Approximately 3 minutes after completion of the addition approximately 30 ml of 1M HCl is added, the mixture is further diluted with approximately 180 ml of water, and extracted with approximately 40 ml of 1:1 ether:petroleum ether six times. The combined organic layers are washed with approximately 100 ml of water, then approximately 100 ml of saturated aqueous sodium chloride, and dried over MgSO₄. Concentration of the solution provides product III as a mixture of isomers at the 4-position.

Approximately 0.90 ml of diphenyl chlorophosphate and 0.80 ml of N,N-diisopropylethylamine are added simultaneously in a dropwise fashion to a cold solution (ice bath) of approximately 2.8 g of product III dissolved in approximately 30 ml of dry acetonitrile under an argon atmosphere. The ice bath is removed and the mixture is allowed to stir approximately 30 minutes at room temperature before concentrating and purifying by chromatography on silica gel to provide product IV as a single isomer.

A solution containing approximately 1.3 g of product IV in approximately 4.5 ml of dry acetonitrile is cooled in an ice bath under an argon atmosphere. Approximately 0.53 ml of N,N-diisopropylethylamine is added followed by the dropwise addition of approximately 0.20 ml of 2-mercaptoethanol. After stirring for approximately 10 minutes the ice bath is removed and the solution is stirred approximately 3 hours longer at room temperature. Concentration of the solution, followed by chromatography on silica gel, provides product V.

Approximately 0.80 g of the product V is dissolved in 8 ml of dichloromethane along with approximately 0.34 ml of triethylamine, and the mixture is cooled in an ice bath under an inert atmosphere. Approximately 0.14 ml of methanesulfonyl chloride is added dropwise, and the mixture is stirred approximately 15 minutes longer. The reaction mixture is transferred to a separatory funnel along with approximately 40 ml of dichloromethane used to rinse the reaction flask. The dichloromethane solution is washed sequentially with ice water, cold 1N hydrochloric acid, saturated aqueous sodium bicarbonate, and saturated aqueous sodium chloride. After drying over Na₂SO₄ and concentration of the solution product VI is obtained.

Reactant VII is prepared by adding 1N NaOH to a solution of 1.9 gm 1-cyclopropyl-6-fluoro-1,4-dihydro-8-oxo-7-(1-piperazinyl) 3-quinoline thiocarboxylic acid (prepared as described herein) in 75 ml of water at approximately 5° C. to adjust the pH to 12. Then approximately 12 ml of acetone is added followed by the dropwise addition of 1.4 gm 2-(trimethylsilyl)ethyl chloroformate (made according to Zhur. obschei. Khim. 1968, 38, 1179) in 10 ml acetone. During the addition, the pH is maintained around 12 with the periodic addition of further 1N NaOH and the reaction is maintained at approximately 5° C. After 30 minutes an additional 0.7 gm aliquot of 2-(trimethylsilyl)ethyl chloroformate in 5 ml acetone is added. The reaction is allowed to warm to room temperature over 3 hours and then the acetone is removed by evaporation. The remaining solution is then extracted with methylene chloride, the aqueous layer is acidified and then extracted 2× with methylene chloride. The organic layer is then dried with sodium sulfate, concentrated to dryness, and triturated with acetone/hexanes to give approximately 2 gm of solid. This product is then dissolved in methylene chloride and chilled to approximately 5° C., and a solution of 185 mg of sodium hydroxide in 0.5 ml methanol is added dropwise. After 1 hour the reaction mixture is evaporated to dryness and the residue is triturated with acetone to yield reactant (VII).

A mixture of approximately 0.5 gm of product VI and 0.48 gm reactant VII were combined in 10 ml DMF and allowed to react at room temperature for 2 hours. The solvent is removed in vacuo and the residue is dissolved in chilled methylene chloride and extracted with water, 3× with cold 10% sodium bicarbonate, then water and finally dried over sodium sulfate. The solution was concentrated to dryness to obtain product VIII.

To a solution of 0.25 gm product VIII in 10 ml DMF is added approximately 0.55 g of tetra-n-butylammonium fluoride and the mixture is stirred approximately 6 hours at room temperature. The reaction is chilled and approximately 2 ml of cold saturated aqueous sodium bicarbonate is added. The mixture is eluted through a DowexR 50×4 (Na cycle) column with deionized water. The appropriate fractions are concentrated in vacuo, then lyophilized to give the final product IX.

Similarly, the following quinolonyl lactams are prepared by the general procedure of this Example, with substantially similar results.

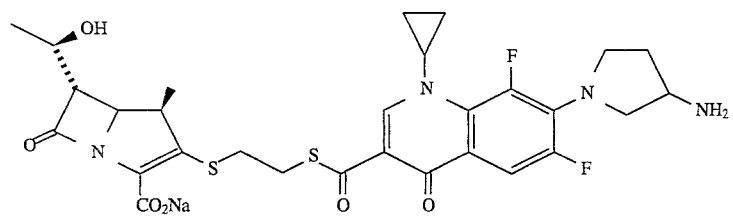

using the quinolone 7-(3-aminopyrrolidinyl)-1-cyclopropyl-6,8-difluoro-1,4-dihydro-4oxo 3-quinoline carboxylic acid (prepared according to J. P. Sanchez, et. al., J. Med. Chem., 1988, 31, 983)

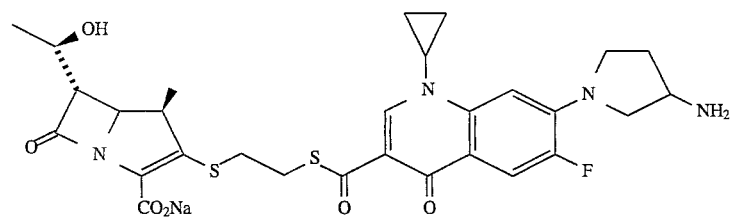

using the quinolone 7-(3-aminopyrrolidinyl-1-cyclopropyl-6-fluoro-1,4-dihydro-4oxo 3quinoline carboxylic acid (prepared according to J. P. Sanchez, et. al., J. Med. Chem., 1988, 31, 983).

EXAMPLE 15

[6R-[6a,7b]]-3-[[(1-cyclopropyl-6-fluoro-1,4-dihydro-4-oxo 7-(1-piperazinyl)-3-quinolinyl)carbonylthio]methyl]-8-oxo 7-[(phenoxyacetyl)amino]-5-thia-1-azabicyclo]4.2.0] oct-2-ene-2-carboxylic acid sodium salt

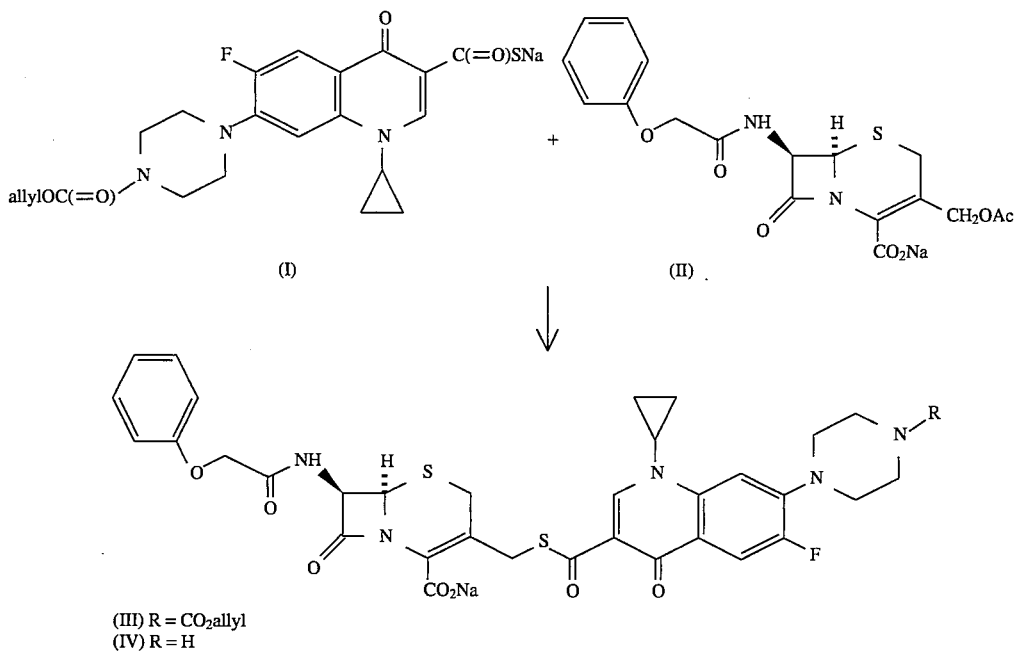

(III) R = CO₂allyl
(IV) R = H

A mixture of 1.0 gm 3-(acetyloxymethyl)-8-oxo-7[(phenoxyacetyl)amino]-5-thia1-azabicyclo ]4.2.0]oct-2-ene-carboxylic acid sodium salt (II, prepared according to R. B. Morin, et al., J. Am. Chem. Soc., 1969, 91, 1401) and 1.1 gm reactant (I, preparation described herein) in water adjusted to approximately pH 8 with sodium bicarbonate is stirred for 24 hr at approximately 40° C. The reaction mixture is cooled and the solvent removed in vacuo. The residue is triturated with acetone/hexanes to obtain purified product (III).

To a solution of 0.8 gm of product (III) in approximately 20 ml methylene chloride containing 0.0 g ml water and 12 mg bis(triphenylphosphine) palladium chloride. Then approximately 0.55 ml of tributyltin hydride is added dropwise while maintaining the reaction at approximately 20° C. The mixture is stirred vigorously for 10 min during which time a precipitate forms. The solid is collected by filtration and resuspended in water containing 1 equivalent of sodium bicarbonate. Addition of a small amount of acetone initially causes a solution to form, further addition reprecipitates the desired product (IV) which is collected and dried.

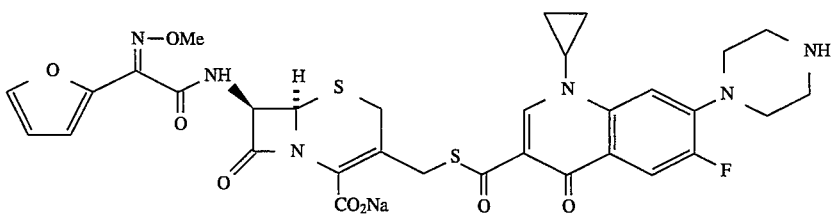

using the beta-lactam 3-[[(aminocarbonyl)oxy]methyl]-7-[[2-furanyl methoxyimino)acetyl]amino]-8-oxo-5-thia-1-azabicyclo [4.2.0]oct-2-ene-carboxylic acid (prepared according to M. C. Cook, et. al., U.S. Pat. No. 3,974,153)

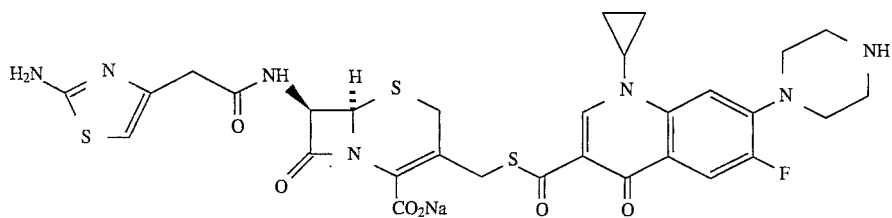

using the beta-lactam 3-(acetyloxymethyl)-7-[[(2-amino-4-thiazolyl)acetyl] amino]-8-oxo-5-thia-1-azabicyclo[4.2.0]oct-2-ene-2-carboxylic acid (prepared according to J. Org. Chem., 1970, 35, 2430).

6-fluoro-1,4-dihydro-4-oxo 3-quinoline carboxylic acid (prepared according to J. P. Sanchez, et. al., J. Med. Chem., 1988, 31, 983 )

EXAMPLE 16

According to the general procedure of Example 15, the following quinolonyl lactam is made:

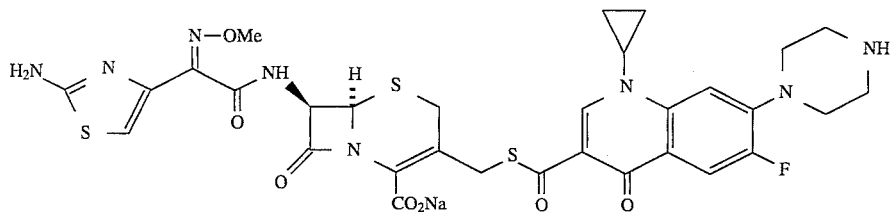

using the beta-lactam 3-[(acetyloxy)methyl]-7-[(2-amino-4-thiazolyl) methoxyimino)acetyl]amino]-8-oxo-5-thia-1-azabicyclo [4.2.0]oct-2-ene-carboxylic acid (prepared according to M. Ochiai, et al., U.S. Pat. No. 4,098,888).

Similarly, the following quinolonyl lactams are prepared by the general procedure of this Example, with substantially similar results.

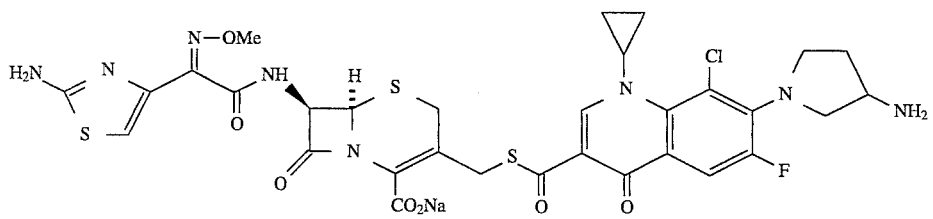

using the quinolone 7-(3-aminopyrrolidinyl)-1-chloro-1-cyclopropyl-6-fluoro-1,4-dihydro 4-oxo-3-quinoline carboxylic acid (prepared according to J. P. Sanchez, et. al., J. Med. Chem., 1988, 31, 983)

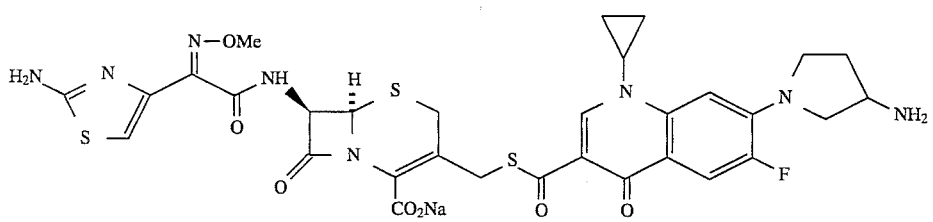

using the quinolone 7-(3-aminopyrrolidinyl-1-cyclopropyl-

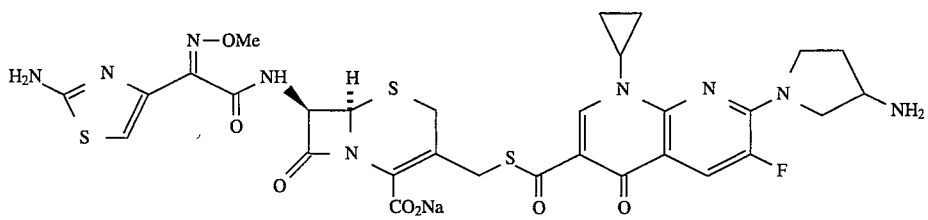

using the naphthyridinone 7-(3-aminopyrrolidinyl)-1-cyclopropyl-6-fluoro-1,4-dihydro-4-oxo 1,8-naphthyridine-3-carboxylic acid (prepared according to J. P. Sanchez, et. al., J. Med. Chem., 1988, 31, 983).

EXAMPLE 17

According to the general procedure of Example 16, the following quinolonyl lactam is made:

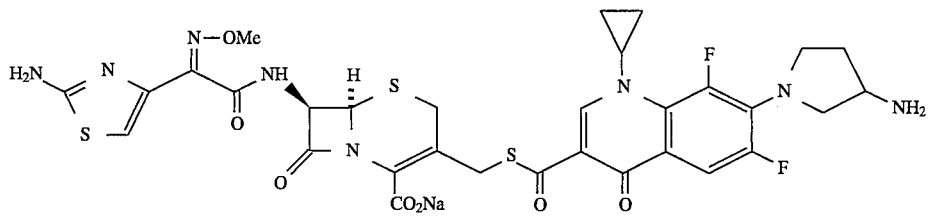

using the quinolone 7-(3-aminopyrrolidinyl)-1-cyclopropyl-6,8-difluoro-1,4-dihydro-4-oxo 3-quinoline carboxylic acid (prepared according to J. P. Sanchez, et. al., J. Med. Chem., 1988, 31, 983).

Similarly, the following quinolonyl lactams are prepared by the general procedure of this Example, with substantially similar results.

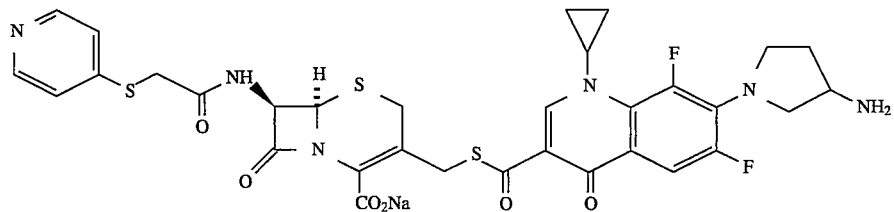

using the beta-lactam 3-(acetyloxymethyl)-8-oxo-7-[(4-pyridylthioacetyl) amino]-5-thia-1-azabicyclo[4.2.0]oct-2-ene-2-carboxylic acid (prepared according to S. Crast, et. al., J. Med. Chem., 1973, 16, 1413)

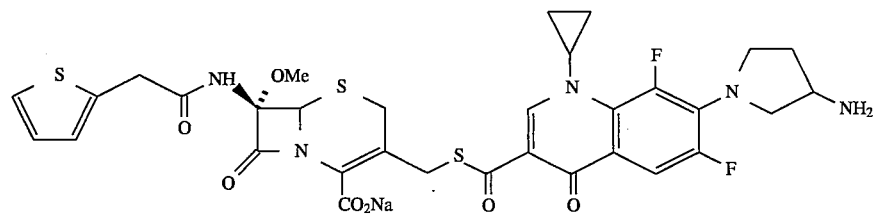

using the beta-lactam 3-(acetyloxymethyl)-7-methoxy-8-oxo-7-[(2-thienylacetyl)amino] 5-thia-1-azabicyclo[4.2.0]oct-2-ene-2-carboxylic acid (prepared according to Karady, et al., J. Am. Chem. Soc., 1972, 94, 1410).

The following other quinolonyl lactams are also prepared by the general procedure of this Example and Examples 12–16, with substantially similar results.

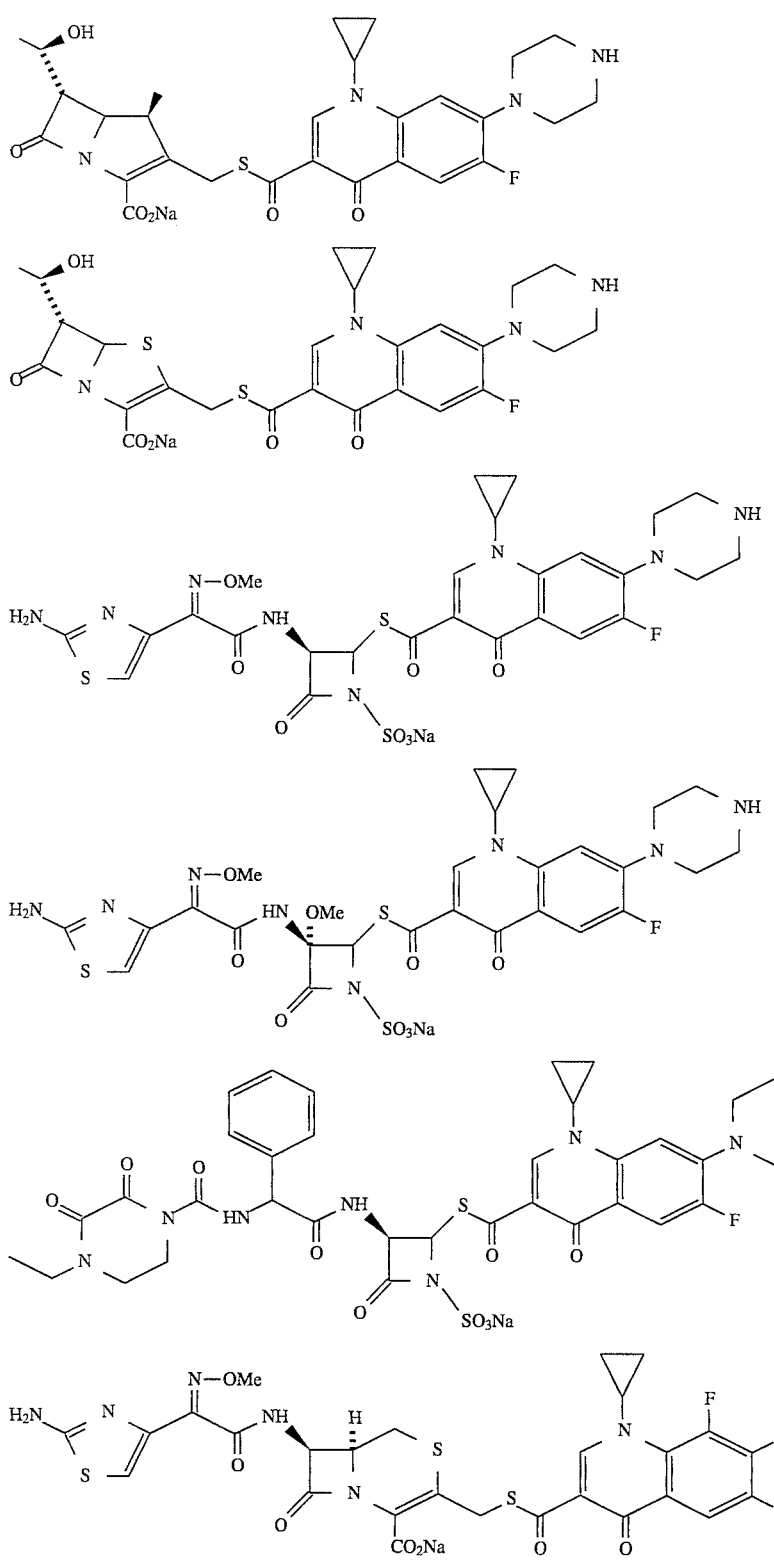

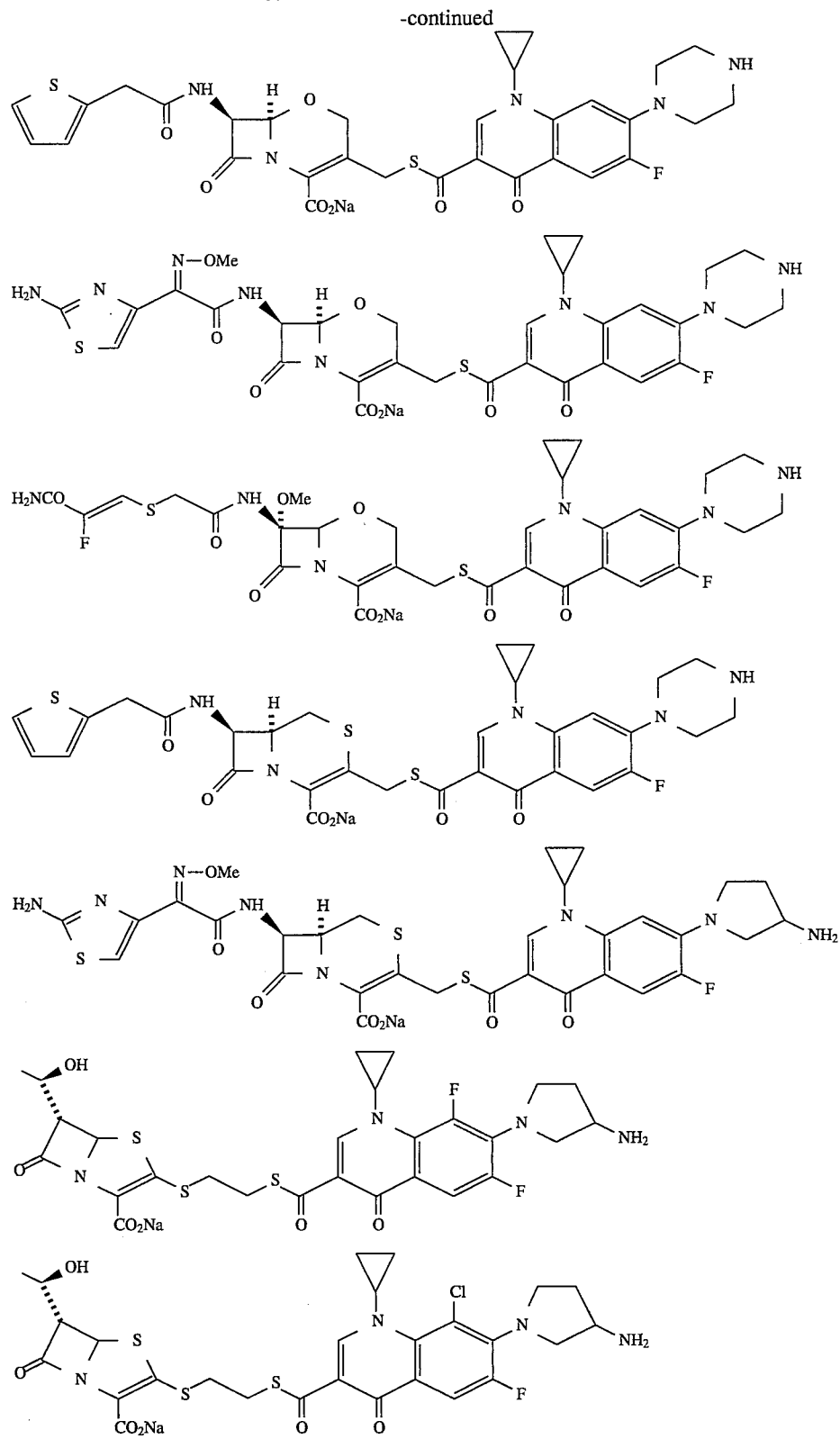

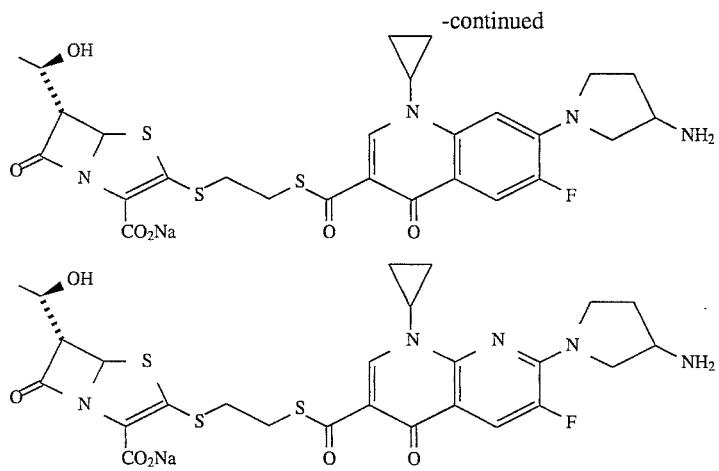

EXAMPLE 18

An antimicrobial composition for parenteral administration, according to this invention, is made comprising:

| Component | Amount |
|---|---|
| [5R-[5a,6a]]-3-[[[1-cyclopropyl-6,8-difluoro-1,4-dihydro-4-oxo-7-(3-aminomethyl-1-pyrrolidinyl)-3-quinolinyl]carbonylamino]methyl]-6-[(R)-1-hydroxyethyl]-7-oxo-4-thia-1-azabicyclo[3.2.0]hept-2-ene-2-carboxylic acid | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated.

EXAMPLE 19

An enteric coated antimicrobial composition for oral administration, according to this invention, is made comprising the following tablet:

| Component | Amount (mg) |
|---|---|
| [5R-[5a,6a]]-3-[[[1-cyclopropyl-6,8-difluoro-1,4-dihydro-4-oxo-7-(3-aminomethyl-1-pyrrolidinyl)-3-quinolinyl]carbonylamino]methyl]-6-[(R)-1-hydroxyethyl]-7-oxo-4-thia-1-azabicyclo[3.2.0]hept-2-ene-2-carboxylic acid | 350.0 |
| starch | 30.0 |
| magnesium stearate | 5.0 |
| microcrystalline cellulose | 100.0 |
| colloidal silicon dioxide | 2.5 |
| povidone | 12.5 |

The components are admixed into a bulk mixture. Compressed tablets are formed, using tabletting methods known in the art. The tablet is then coated with a suspension of methacrylic acid/methacrylate acid ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:

1. A compound of the formula

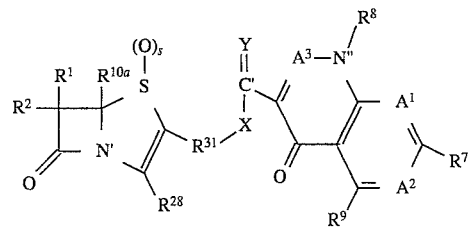

wherein (A) $R^1$ is hydrogen; halogen; $C_1$–$C_8$ alkyl; $C_2$–$C_8$ alkenyl; a 3–8 atom heteroalkyl having 1 or 2 heteroatoms selected from O, N, or S; a 3–9 atom monocyclic or 7–17 atom polycyclic carbocycle; a 3–9 atom monocyclic or 7–17 atom polycyclic heterocycle; wherein said heterocycles have one or more heteroatoms selected from O,S, or N; $R^{10a}$—O—, $R^{10a}$—O—, $R^{10a}$CH=N—, $(R^{10})(R^{11})$N—, $R^{12}$—C(=CHR$^{15}$)—C(=O)NH—, $R^{12}$—C(=NO—R$^{14}$)—C(=O)NH—, or $R^{13}$—(CH$_2$)$_m$—C(=O)NH—; where (1) m is an integer from 0 to 9;

(2) $R^{10}$ and $R^{11}$ are, independently, $R^{10a}$ where $R^{10a}$ is hydrogen; $C_1$–$C_8$ alkyl; $C_2$–$C_8$ alkenyl; a 3–9 atom monocyclic or 7–17 atom polycyclic heterocycle; or $R^{10}$ and $R^{11}$ together comprise a 3–9 atom monocyclic or 7–17 atom polycyclic heterocycle, including the nitrogen to which they are bonded; wherein said heterocycles have one or more heteroatoms selected from O, S, or N;

(3) $R^{12}$ is hydrogen; $C_1$-$C_8$ alkyl; $C_2$-$C_8$ alkenyl; a 3-8 atom heteroalkyl having 1 or 2 heteroatoms selected from O, N, or S; a 3-8 atom heteroalkenyl having 1 or 2 heteroatoms selected from O, N, or S; a 3-9 atom monocyclic or 7-17 atom polycyclic carbocycle; or a 3-9 atom monocyclic or 7-17 atom polycyclic heterocycle; wherein said heterocycles have one or more heteroatoms selected from O, S, or N;
wherein said arylalkyl is a $C_1$-$C_8$ alkyl substituted with an aryl group; and wherein said heteroarylalkyl is a $C_1$-$C_8$ alkyl substituted with an aryl group having one or more heteroatoms selected from O, N, or S;

(4) $R^{13}$ is $R^{12}$, —$Z^1$, or —CH($Z^2$)($R^{12}$);

(5) $R^{14}$ is $R^{12}$, arylalkyl, heteroarylalkyl, —C($R^{17}$)($R^{18}$)COOH, —(=O)O—$R^{12}$, or —C(=O)NH—$R^{12}$, where $R^{17}$ and $R^{18}$ are, independently, $R^{12}$ or together comprise a 3-9 atom monocyclic or 7-17 atom polycyclic carbocycle or a 3-9 atom monocyclic or 7-17 atom polycyclic heterocycle, including the carbon atom to which $R^{17}$ and $R^{18}$ are bonded; wherein said heterocycles have one or more heteroatoms selected from O, S, or N; and
wherein said arylalkyl is a $C_1$-$C_8$ alkyl substituted with an aryl group; and wherein said heteroarylalkyl is a $C_1$-$C_8$ alkyl substituted with an aryl group having one or more heteroatoms selected from O, N, or S;

(6) $R^{15}$ is $R^{14}$, halogen, —$Z^1$, or —CH($Z^2$)($R^{12}$);

(7) $Z^1$ is —C(=O)O$R^{16}$, —C(=O)$R^{16}$, —N($R^{19}$)$R^{16}$, —S(O)$_p$$R^{24}$, or —O$R^{24}$; and $Z^2$ is $Z^1$ or —OH, —SH, or —SO$_3$H;

(a) p is an integer from 0 to 2;

(b) $R^{19}$ is hydrogen; $C_1$-$C_8$ alkyl; $C_2$-$C_8$ alkenyl; a 3-8 atom heteroalkyl having 1 or 2 heteroatoms selected from O, N, or S; a 3-8 atom heteroalkenyl having 1 or 2 heteroatoms selected from O, N, or S; a 3-9 atom monocyclic or 7-17 atom polycyclic carbocycle; a 3-9 atom monocyclic or 7-17 atom polycyclic heterocycle; —SO$_3$H; —C(=O)$R^{20}$; or, when $R^{13}$ is —CH($Z^2$)($R^{12}$) and $Z^2$ is —N($R^{19}$)$R^{16}$, $R^{19}$ and $R^{16}$ may together comprise a 3-9 atom monocyclic or 7-17 atom polycyclic heterocycle; wherein said heterocycles have one or more heteroatoms selected from O, S, or N; and (c) $R^{20}$ is $R^{12}$, NH($R^{12}$), N($R^{12}$)($R^{21}$), O($R^{21}$), or S($R^{21}$); where $R^{21}$ is $C_1$-$C_8$ alkyl; $C_2$-$C_8$ alkenyl; a 3-9 atom monocyclic or 7-17 atom polycyclic carbocycle; a 3-9 atom monocyclic or 7-17 atom polycyclic heterocycle; or when $R^{20}$ is N($R^{12}$)($R^{21}$), $R^{21}$ and $R^{12}$ may together comprise a 3-9 atom monocyclic or 7-17 atom polycyclic heterocycle; wherein said heterocycles have one or more heteroatoms selected from O, S, or N; and (8) $R^{16}$ is $R^{24}$ or hydrogen; where $R^{24}$ is $C_1$-$C_8$ alkyl; $C_2$-$C_8$ alkenyl; arylalkyl; a 3-8 atom heteroalkyl having of 1 or 2 heteroatoms selected from O, N, or S; a 3-8 atom heteroalkenyl having of 1 or 2 heteroatoms selected from O, N, or S; heteroarylalkyl; a 3-9 atom monocyclic or 7-17 atom polycyclic carbocycle; a 3-9 atom monocyclic or 7-17 atom polycyclic heterocycle; wherein said heterocycles have one or more heteroatoms selected from O, S, or N; and wherein said arylalkyl is a $C_1$-$C_8$ alkyl substituted with an aryl group and wherein said heteroarylalkyl is a $C_1$-$C_8$ alkyl substituted with an aryl group having one or more heteroatoms selected from O, N, or S; or, when $Z^1$ is N($R^{19}$)$R^{16}$ and $R^{16}$ is $R^{24}$, $R^{16}$ and $R^{19}$ may together comprise a 3-9 atom monocyclic or 7-17 atom polycyclic heterocycle including the nitrogen atom to which $R^{19}$ is bonded;

(B) $R^2$ is hydrogen, halogen, alkoxy, or $R^{22}$C(=O)NH—, where $R^{22}$ is hydrogen or $C_1$-$C_8$ alkyl;

(C) S is an integer from 0 to 2;

(D) $R^{31}$ is nil; $C_1$-$C_8$ alkyl; $C_2$-$C_8$ alkenyl; a 3-9 atom monocyclic or 7-17 atom polycyclic carbocycle; or a 3-9 atom monocyclic or 7-17 atom polycyclic heterocycle; wherein said heterocycles have one or more heteroatoms selected from O, S, or N;

(E) X is X' or $Z^4$—$R^{34}$—X', where (a) $Z^4$ is —O—; —S(O)t—, where t is an integer of 0 to 2; or —N$R^{36}$—;

(b) X' is oxygen, sulfur, or $R^{35}$—N$R^{36}$;

(c) $R^{34}$ is $C_1$-$C_8$ alkyl; $C_2$-$C_8$ alkenyl; a 3-8 atom heteroalkyl having 1 or 2 heteroatoms selected from O, N, or S; a 3-8 atom heteroalkenyl having 1 or 2 heteroatoms selected from O, N, or S; a 3-9 atom monocyclic or 7-17 atom polycyclic carbocycle; or a 3-9 atom monocyclic or 7-17 atom polycyclic heterocycle; wherein said heterocycles have one or more heteroatoms selected from O, S, or N;

(d) $R^{35}$ is nil, N($R^{36}$), or oxygen;

(e) $R^{36}$ is hydrogen; $C_1$-$C_8$ alkyl; $C_2$-$C_8$ alkenyl; a 3-9 atom monocyclic or 7-17 atom polycyclic carbocycle; or a 3-9 atom monocyclic or 7-17 atom polycyclic heterocycle; wherein said heterocycles have one or more heteroatoms selected from O, S, or N;

(F) (1) if X' is sulfur or $R^{35}$—N$R^{36}$, Y is oxygen or Y'; or (2) if X' is oxygen, Y is Y'; where Y' is sulfur or —N$R^{39}$; where $R^{39}$ is hydrogen; $C_1$-$C_8$ alkyl; oxygen; sulfur; or N($R^{10a}$); or if $A^3$ is C($R^{41}$), then $R^{39}$ and $R^{41}$ may together comprise a 3-9 atom monocyclic or 7-17 atom polycyclic heterocycle; wherein said heterocycles have one or more heteroatoms selected from O, S, or N;

(G) (1) $A^1$ is N or C($R^{40}$); where $R^{40}$ is hydrogen, hydroxy, alkoxy, nitro, cyano, halogen, $C_1$-$C_8$ alkyl, or N($R^{10}$)($R^{11}$);

(2) $A^2$ is N or C($R^6$); where $R^6$ is hydrogen or halogen;

(3) $A^3$ is N or C($R^{41}$); where $R^{41}$ is hydrogen;

(4) $R^8$ is hydrogen; $C_1$-$C_8$ alkyl; a 3-9 atom monocyclic or 7-17 atom polycyclic carbocycle; a 3-9 atom monocyclic or 7-17 atom polycyclic heterocycle; alkoxy; hydroxy; $C_2$-$C_8$ alkenyl; arylalkyl; or N($R^{10}$)($R^{11}$); wherein said arylalkyl is a $C_1$-$C_8$ alkyl substituted with an aryl group;

(5) $R^7$ is hydrogen; halogen; alkyl; a 3-9 atom monocyclic or 7-17 atom polycyclic carbocycle; or a 3-9 atom monocycle or 7-17 atom polycyclic heterocycle; wherein said heterocycles have one or more heteroatoms selected from O, S, or N; and (7) $R^9$ is hydrogen, halogen, nitro, or N($R^{10}$)($R^{11}$);

(H) except that (1) when $A^1$ is C($R^{40}$), $R^8$ and $R^{40}$ may together comprise a 3-9 atom monocyclic or 7-17 atom polycyclic heterocycle; including N" and $A^1$; wherein said heterocycles have one or more heteroatoms selected from O, S, or N;

(2) when $A^2$ is C($R^6$), $R^6$ and $R^7$ may together comprise —O—(CH$_2$)$_n$—O—, where n is an integer from 1 to 4; and (3) when $A^3$ is C($R^{41}$), $R^8$ and $R^{41}$ may together comprise a 3-9 atom monocyclic or 7-17 atom polycyclic heterocycle including N'' and the adjacent carbon to which $R^{41}$ is bonded; wherein said heterocycles have one or more heteroatoms selected from O, S, or N;

and pharmaceutically-acceptable salts and biohydrolyzable esters thereof, and hydrates thereof.

2. A compound of the formula

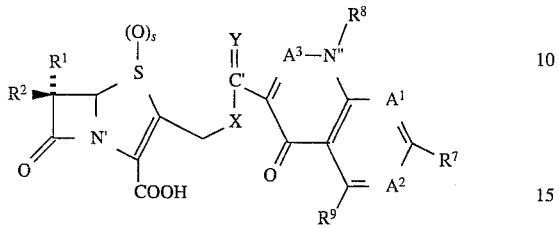

wherein (A) $R^1$ is hydrogen; halogen; $C_1$–$C_8$ alkyl; $C_2$–$C_8$ alkenyl; a 3-8 atom heteroalkyl having 1 or 2 heteroatoms selected from O, N, or S; a 3-9 atom monocyclic or 7-17 atom polycyclic carbocycle; a 3-9 atom monocyclic or 7-17 atom polycyclic heterocycle; $R^{10a}$—O—; $R^{10a}$CH=N—; $(R^{10})(R^{11})$N—; $R^{12}$—C(=CHR$^{15}$)—C(=O)NH—; $R^{12}$—C(=NO—R$^{14}$)—C(=O)NH—; or $R^{13}$—(CH$_2$)$_m$—C(=O)NH—; wherein said heterocycles have one or two heteroatoms selected from O, S, or N; and where (1) m is an integer from 0 to 9;

(2) $R^{10}$ and $R^{11}$ are, independently, $R^{10a}$ where $R^{10a}$ is hydrogen; $C_1$–$C_8$ alkyl; $C_2$–$C_8$ alkenyl; a 3-9 atom monocyclic or 7-17 atom polycyclic carbocycle; or a 3-9 atom monocyclic or 7-17 atom polycyclic heterocycle; or $R^{10}$ and $R^{11}$ together comprise a 3-9 atom monocyclic or 7-17 atom polycyclic heterocycle; including the nitrogen to which they are bonded; wherein said heterocycles have one or two heteroatoms selected from O, S, or N;

(3) $R^{12}$ is hydrogen; $C_1$–$C_8$ alkyl; $C_2$–$C_8$ alkenyl; a 3-8 atom heteroalkyl having 1 or 2 heteroatoms selected from O, N, or S; a 3-8 atom heteroalkenyl having 1 or 2 heteratoms selected from O, N, or S; a 3-9 atom monocyclic or 7-17 atom polycyclic carbocycle; or a 3-9 atom monocyclic or 7-17 atom polycyclic heterocycle; wherein said heterocycles have one or two heteroatoms selected from O, S, or N;

(4) $R^{13}$ is $R^{12}$, —$Z^1$, or —CH($Z^2$)($R^{12}$);

(5) $R^{14}$ is $R^{12}$; arylalkyl; heteroarylalkyl; —C($R^{17}$)($R^{18}$)COOH; —C(=O)O—$R^{12}$; wherein said arylalkyl is a $C_1$–$C_8$ alkyl substituted with an aryl group and wherein said heteroarylalkyl is a $C_1$–$C_8$ alkyl substituted with an aryl group substituted with one or more heteroatoms selected from O, N, or S; or —C(=O)NH—$R^{12}$; where $R^{17}$ and $R^{18}$ are, independently, $R^{12}$ or together comprise a 3-9 atom monocyclic or 7-17 atom polycyclic carbocycle; or a 3-9 atom monocyclic or 7-17 atom polycyclic heterocycle; including the carbon atom to which $R^{17}$ and $R^{18}$ are bonded; wherein said heterocycles have one or two heteroatoms selected from O, S, or N;

(6) $R^{15}$ is $R^{14}$, halogen, —$Z^1$, or —CH($Z^2$)($R^{12}$);

(7) $Z^1$ is —C(=O)O$R^{16}$, —C(=O)$R^{16}$, —N($R^{19}$)$R^{16}$, —S(O)$_p$$R^{24}$, or —O$R^{24}$; and $Z^2$ is $Z^1$ or —OH, —SH, or —SO$_3$H;

(a) p is an integer from 0 to 2;

(b) $R^{19}$ is hydrogen; $C_1$–$C_8$ alkyl; $C_2$–$C_8$ alkenyl; a 3-8 atom heteroalkyl having 1 or 2 heteroatoms selected from O, N, or S; a 3-8 atom heteroalkenyl having 1 or 2 heteratoms selected from O, N, or S; a 3-9 atom monocyclic or 7-17 atom polycyclic carbocycle; a 3-9 atom monocyclic or 7-17 atom polycyclic heterocycle; —SO$_3$H; —C(=O)R$^{20}$; or, when $R^{13}$ is —CH($Z^2$)($R^{12}$) and $Z^2$ is —N($R^{19}$)$R^{16}$, $R^{19}$ and $R^{16}$ may together comprise a 3-9 atom monocyclic or 7-17 atom polycyclic heterocycle; wherein said heterocycles have one or two heteroatoms selected from O, S, or N; and (c) $R^{20}$ is $R^{12}$, NH($R^{12}$), N($R^{12}$)($R^{21}$), O($R^{21}$), or S($R^{21}$); where $R^{21}$ is $C_1$–$C_8$ alkyl; $C_2$–$C_8$ alkenyl; a 3-9 atom monocyclic or 7-17 atom polycyclic carbocycle; a 3-9 atom monocyclic or 7-17 atom polycyclic heterocycle; or when $R^{20}$ is N($R^{12}$)($R^{21}$), $R^{21}$ and $R^{12}$ may together comprise a 3-9 atom monocyclic or 7-17 atom polycyclic heterocycle; wherein said heterocycles have one or two heteroatoms selected from O, S, or N; and (8) $R^{16}$ is $R^{24}$ or hydrogen; where $R^{24}$ is $C_1$–$C_8$ alkyl; $C_2$–$C_8$ alkenyl; arylalkyl; a 3-8 atom heteroalkyl having 1 or 2 heteroatoms selected from O, N, or S; a 3-8 atom heteroalkenyl having 1 or 2 heteroatoms selected from O, N, or S; heteroarylalkyl; a 3-9 atom monocyclic or 7-17 atom polycyclic carbocycle; a 3-9 atom monocyclic or 7-17 atom polycyclic heterocycle; wherein said arylalkyl is a $C_1$–$C_8$ alkyl substituted with an aryl group and wherein said heteroarylalkyl is a $C_1$–$C_8$ alkyl substituted with an aryl group substituted with one or more heteroatoms selected from O, N, or S; amid wherein said heterocycles have one or two heteroatoms selected from O, S, or N; or, when $Z^1$ is N($R^{19}$)$R^{16}$ and $R^{16}$ is $R^{24}$, $R^{16}$ and $R^{19}$ may together comprise a 3-9 atom monocyclic or 7-17 atom polycyclic heterocycle including the nitrogen atom to which $R^{19}$ is bonded; and wherein said heterocycles have one or two heteroatoms selected from O, S, or N;

(B) $R^2$ is hydrogen, halogen, alkoxy, or $R^{22}$C(=O)NH—, where $R^{22}$ is hydrogen or $C_1$–$C_8$ alkyl;

(C) s is an integer from 0 to 2;

(D) X is X' or $Z^4$—$R^{34}$—X', where (1) $Z^4$ is —O—; —S(O)t—, where t is an integer of 0 to 2; or —NR$^{36}$—;

(2) X' is oxygen, sulfur, or $R^{35}$—NR$^{36}$;

(3) $R^{34}$ is $C_1$–$C_8$ alkyl; $C_2$–$C_8$ alkenyl; a 3-8 atom heteroalkyl having 1 or 2 heteroatoms selected from O, N, or S; a 3-8 atom heteroalkenyl having 1 or 2 heteratoms selected from O, N, or S; a 3-9 atom monocyclic or 7-17 atom polycyclic carbocycle; or a 3-9 atom monocyclic or 7-17 atom polycyclic heterocycle; wherein said heterocycles have one or two heteroatoms selected from O, S, or N;

(4) $R^{35}$ is nil, N($R^{36}$), or oxygen;

(5) $R^{36}$ is hydrogen; $C_1$–$C_8$ alkyl; $C_2$–$C_8$ alkenyl; a 3-9 atom monocyclic or 7-17 atom polycyclic carbocycle; or a 3-9 atom monocyclic or 7-17 atom polycyclic heterocycle; wherein said heterocycles have one or two heteroatoms selected from O, S, or N;

(E) (1) if X' is sulfur or $R^{35}$—NR$^{36}$, Y is oxygen or Y'; or (2) if X' is oxygen, Y is Y'; where Y' is sulfur or —NR$^{39}$; where $R^{39}$ is hydrogen, $C_1$–$C_8$ alkyl, oxygen, sulfur, or N($R^{10a}$), or if $A^3$ is C($R^{41}$), then $R^{39}$ and $R^{41}$ may together comprise a 3-9 atom monocyclic or 7-17 atom polycyclic heterocycle; wherein said heterocycles have one or two heteroatoms selected from O, S, or N;

(F) (1) $A^1$ is N or $C(R^{40})$; where $R^{40}$ is hydrogen, hydroxy, alkoxy, nitro, cyano, halogen, $C_1-C_8$ alkyl, or $N(R^{10})(R^{11})$;

(2) $A^2$ is N or $C(R^6)$; where $R^6$ is hydrogen or halogen;

(3) $A^3$ is N or $C(R^{41})$; where $R^{41}$ is hydrogen;

(4) $R^8$ is hydrogen; $C_1-C_8$ alkyl; a 3–9 atom monocyclic or 7–17 atom polycyclic carbocycle; a 3–9 atom monocyclic or 7–17 atom polycyclic heterocycle; alkoxy; hydroxy; $C_2-C_8$ alkenyl; aryl alkyl; or $N(R^{10})(R^{11})$; wherein said aryl alkyl is a $C_1-C_8$ alkyl substituted with an aryl group; and wherein said heterocycles have one or more heteroatoms selected from O, S, or N;

(5) $R^7$ is hydrogen; halogen; $C_1-C_8$ alkyl; a 3–9 atom monocyclic or 7–17 atom polycyclic carbocycle; or a 3–9 atom monocyclic or 7–17 atom polycyclic heterocycle; and wherein said heterocycles have one or two heteroatoms selected from O, S, or N;

(7) $R^9$ is hydrogen, halogen, nitro, or $N(R^{10})(R^{11})$;

(G) except that (1) when $A^1$ is $C(R^{40})$, $R^8$ and $R^{40}$ may together comprise a 3–9 atom monocyclic or 7–17 atom polycyclic heterocycle including N" and $A^1$; wherein said heterocycles have one or two heteroatoms selected from O, S, or N;

(2) when $A^2$ is $C(R^6)$, $R^6$ and $R^7$ may together comprise $—O—(CH_2)_n—O—$, where n is an integer from 1 to 4; and (3) when $A^3$ is $C(R^{41})$, $R^8$ and $R^{41}$ may together comprise a 3–9 atom monocyclic or 7–17 atom polycyclic heterocycle including N" and the adjacent carbon to which $R^{41}$ is bonded; wherein said heterocycles have one or two heteroatoms selected from O, S, or N; and pharmaceutically-acceptable salts and biohydrolyzable esters thereof, and hydrates thereof.

3. A compound of the formula

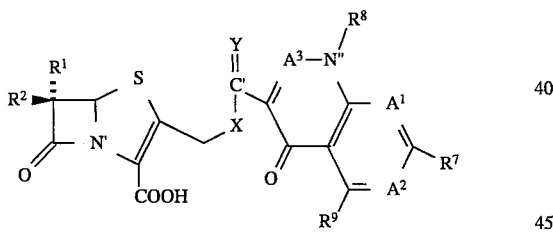

wherein (A) $R^1$ is $C_1-C_8$ alkyl, $C_2-C_8$ alkenyl, $R^{12}—C(=NO—R^{14})—C(=O)NH—$, or $R^{13}—(Cl_2)_m—C(=O)NH—$; where (1) m is an integer from 0 to 3;

(2) $R^{10}$ and $R^{11}$ are, independently, $R^{10a}$ where $R^{10a}$ is hydrogen; $C_1-C_8$ alkyl; $C_2-C_8$ alkenyl; 3–9 atom monocyclic or 7–17 atom polycyclic carbocycle; or a 3–9 atom monocyclic or 7–17 atom polycyclic heterocycle; or $R^{10}$ and $R^{11}$ together comprise a 3–9 atom monocyclic or 7–17 atom polycyclic heterocycle, including the nitrogen to which they are bonded; wherein said .heterocycles have one or two heteroatoms selected from O, S, or N;

(3) $R^{12}$ is $C_1-C_8$ alkyl, a 3–9 atom monocyclic or 7–17 atom polycyclic carbocycle; or a 3–9 atom monocyclic or 7–17 atom polycyclic heterocycle; wherein said heterocycles have one or two heteroatoms selected from O, S, or N;

(4) $R^{13}$ is $R^{12}$, $—Z^1$, or $—CH(Z^2)(R^{12})$;

(5) $R^{14}$ is $R^{12}$ or $—C(R^{17})(R^{18})COOH$;

(6) $R^{15}$ is $R^{14}$ or halogen;

(7) $Z^1$ is $—C(=O)OR^{16}$, $—C(=O)R^{16}$, $—N(R^{19})R^{16}$, $—S(O)_pR^{24}$, or $—OR^{24}$; and $Z^2$ is $Z^1$ or $—OH$, $—SH$, or $—SO_3H$;

(a) p is 0;

(b) $R^{19}$ is hydrogen; $C_1-C_8$ alkyl; $C_2-C_8$ alkenyl; a 3–8 atom heteroalkyl having 1 or 2 heteroatoms selected from O, N, S; a 3–8 atom heteroalkenyl having 1 to 2 heteroatoms selected from O, N, or S; a 3∝9 atom monocyclic or 7–17 atom polycyclic carbocycle; a 3–9 atom monocyclic or 7–17 atom polycyclic heterocycle; $—SO_3H$; $—C(=O)R^{20}$; or, when $R^{13}$ is $—CH(Z^2)(R^{12})$ and $Z^2$ is $—N(R^{19})R^{16}$, $R^{19}$ and $R^{16}$ together may comprise a 3–9 atom monocyclic or 7–17 atom polycyclic heterocycle; wherein said heterocycles have one or two heteroatoms selected from O, S, or N;

(c) $R^{20}$ is $R^{12}$, $NH(R^{12})$, $N(R^{12})(R^{21})$; where $R^{21}$ is $C_1-C_8$ alkyl; $C_2-C_8$ alkenyl; a 3–9 atom monocyclic or 7–17 atom polycyclic carbocycle; a 3–9 atom monocyclic or 7–17 atom polycyclic heterocycle; or when $R^{20}$ is $N(R^{12})(R^{21})$, $R^{21}$ and $R^{12}$ together may comprise a 3–9 atom monocyclic or 7–17 atom polycyclic heterocycle; wherein said heterocycles have one or two heteroatoms selected from O, S, or N;

(8) $R^{16}$ is hydrogen; $C_1-C_8$ alkyl; a 3–9 atom monocyclic or 7–17 atom polycyclic carbocycle; or a 3–9 atom monocyclic or 7–17 atom polycyclic heterocycle; wherein said heterocycles have one or two heteroatoms selected from O, S, or N;

(B) $R^2$ is hydrogen or alkoxy;

(C) X is X' or $Z^4—R^{34}—X'$, where (1) $Z^4$ is $—O—$; $—S(O)t—$, where t is O; or $—NR^{36}—$;

(2) X' is oxygen, sulfur, or $R^{35}—NR^{36}$;

(3) $R^{34}$ is $C_1-C_8$ alkyl or $C_2-C_8$ alkenyl;

(4) $R^{35}$ is nil, $N(R^{36})$, or oxygen;

(5) $R^{36}$ is hydrogen; $C_1-C_8$ alkyl; $C_2-C_8$ alkenyl; a 3–9 atom monocyclic or 7–17 atom polycyclic carbocycle; or a 3–9 atom monocyclic or 7–17 atom polycyclic heterocycle; wherein said heterocycles have one or two heteroatoms selected from O, S, or N;

(D) (1) if X' is sulfur or $R^{35}—NR^{36}$, Y is oxygen; or (2) if X' is oxygen, Y is Y'; where Y' is $—NR^{39}$; where $R^{39}$ is hydrogen, $C_1-C_8$ alkyl, oxygen, sulfur, or $N(R^{10a})$, or if $A^3$ is $C(R^{41})$, then $R^{39}$ and $R^{41}$ may together comprise a 3–9 atom monocyclic or 7–17 atom polycyclic heterocycle; wherein said heterocycles have one or two heteroatoms selected from O, S, or N;

(E) (1) $A^1$ is N or $C(R^{40})$; where $R^{40}$ is hydrogen or halogen;

(2) $A^2$ is $C(R^6)$; where $R^6$ is hydrogen or halogen;

(3) $A^3$ is $C(R^{41})$; where $R^{41}$ is hydrogen;

(4) $R^8$ is $C_1-C_8$ alkyl or a 3–9 atom monocyclic or 7–17 atom polycyclic carbocycle;

(5) $R^7$ is a 3–9 atom monocyclic or 7–17 atom polycyclic heterocycle; and wherein said heterocycles have one or two heteroatoms selected from O, S, or N;

(7) $R^9$ is hydrogen;

(F) except that (1) when $A^1$ is $C(R^{40})$, $R^8$ and $R^{39}$ may together comprise a 3–9 atom monocyclic or 7–17 atom polycyclic heterocycle including N" and $A^1$; wherein said heterocycles have one or two heteroatoms selected from O, S, or N;

(2) when $A^2$ is $C(R^6)$, $R^6$ and $R^7$ may together comprise —O—$(CH_2)_n$—O—, where n is an integer from 1 to 4; and (3) when $A^3$ is $C(R^{41})$, $R^8$ and $R^{41}$ may together comprise a 3–9 atom monocyclic or 7–17 atom polycyclic heterocycle including N" and the adjacent carbon to which $R^{41}$ is bonded; wherein said heterocycles have one or two heteroatoms selected from O, S, or N; and pharmaceutically-acceptable salts and biohydrolyzable esters thereof, and hydrates thereof.

4. A compound, according to claim 1, wherein $R^1$ is $C_1$–$C_8$ alkyl or $C_2$–$C_8$ alkenyl.

5. A compound, according to claim 1, wherein $R^2$ is hydrogen or alkoxy.

6. A compound according to claim 1, wherein: $A^1$ is $C(R^{40})$, $A^2$ is $C(R^6)$, and $A^3(R^{41})$; or $A^1$ is nitrogen, $A^2$ is $C(R^6)$, and $A^3$ is $C(R^{41})$.

7. A compound according to claim 6, wherein $A^1$ is $C(R^{40})$, $A^2$ is $C(R^6)$, and $A^3(R^{41})$.

8. A compound according to claim 7, wherein Q is a 6-fluoroquinolone moiety, a 8-halo-6-fluoroquinolone moiety, a pyridobenzoxazine moiety, a pyridobenthiazine moiety, a isothiazoloquinol inedione moiety, or a isoxazoloquinol inedione moiety.

9. A compound, according to claim 7, wherein $R^8$ is $C_1$–$C_8$ alkyl, aryl, $C_1$–$C_8$ cycloalkyl or alkylamino.

10. A compound, according to claim 9, wherein $R^8$ is ethyl, 2-fluoroethyl, 2-hydroxyethyl, t-butyl, 4-fluorophenyl, 2,4-difluorophenyl, methyl amino or cylcopropyl.

11. A compound, according to claim 9, wherein $R^{40}$ is hydrogen or halo.

12. A compound, according to claim 11, wherein $R^{40}$ is chlorine or fluorine.

13. A compound, according to claim 11, wherein $R^7$ is a nitrogen-containing 3–9 atom monocyclic or 7–17 atom polycyclic heterocycle.

14. A compound, according to claim 13, wherein $R^7$ is piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, or 3,5-dimethylpiperazine.

15. A compound, according to claim 14, wherein $R^8$ is cyclopropyl, and $R^2$ is fluorine.

16. A compound, according to claim 14, wherein $R^7$ is piperazine.

17. A compound according to claim 1, wherein $R^{31}$—X, Y, and C— comprise a linking moiety selected from the group consisting of thioester, amide, imidate, and hydrazide groups.

18. A compound, according to claim 1, wherein said linking moiety is a thioester group, wherein X is S.

19. A compound, according to claim 1, wherein said linking moiety is a thioester group, wherein X is $Z^4$—$R^{39}$—$X^1$, and $X^1$ is S.

20. A compound, according to claim 1, wherein said linking moiety is an amide group.

21. A composition for treating or preventing an infectious disorder in a human or other animal subject, comprising:

(1) a safe and effective amount of a compound of claim 1; and (2) a pharmaceutically-acceptable carrier.

22. A composition for treating or preventing an infectious disorder in a human or other animal subject, comprising:

(1) a safe and effective amount of a compound of claim 2; and (2) a pharmaceutically-acceptable carrier.

23. A composition for treating or preventing an infectious disorder in a human or other animal subject, comprising:

(1) a safe and effective amount of a compound of claim 7; and (2) a pharmaceutically-acceptable carrier.

24. A composition for treating or preventing an infectious disorder in a human or other animal subject, comprising:

(1) a safe and effective amount of a compound of claim 13; and (2) a pharmaceutically-acceptable carrier.

25. A composition for treating or preventing an infectious disorder in a human or other animal subject, comprising:

(1) a safe and effective amount of a compound of claim 16; and (2) a pharmaceutically-acceptable carrier.

26. A composition for treating or preventing an infectious disorder in a human or other animal subject, comprising:

(1) a safe and effective amount of a compound of claim 17; and (2) a pharmaceutically-acceptable carrier.

27. A composition for treating or preventing an infectious disorder in a human or other animal subject, comprising:

(1) a safe and effective amount of a compound of claim 3; and (2) a pharmaceutically-acceptable carrier.

28. A composition for treating or preventing an infectious disorder in a human or other animal subject, according to claim 21, wherein said composition is suitable for parenteral administration.

29. A composition for treating or preventing an infectious disorder in a human or other animal subject, according to claim 21, wherein said composition is suitable for oral administration.

30. A method for preventing or treating an infectious disorder in a human or other animal subject, by administering to said subject a safe and effective amount of a compound of claim 1.

31. A method for preventing or treating an infectious disorder in a human or other animal subject, by administering to said subject a safe and effective amount of a compound of claim 2.

32. A method for preventing or treating an infectious disorder in a human or other animal subject, by administering to said subject a safe and effective amount of a compound of claim 13.

33. A method for preventing or treating an infectious disorder in a human or other animal subject, by administering to said subject a safe and effective amount of a compound of claim 16.

34. A method for preventing or treating an infectious disorder in a human or other animal subject, by administering to said subject a safe and effective amount of a compound of claim 17.

35. A method for preventing or treating an infectious disorder in a human or other animal subject, by administering to said subject a safe and effective amount of a compound of claim 3.

\* \* \* \* \*